United States Patent
Zhang et al.

(10) Patent No.: US 10,316,025 B2
(45) Date of Patent: Jun. 11, 2019

(54) SUBSTITUTED PIPERAZINE COMPOUNDS AND METHODS OF USE AND USE THEREOF

(71) Applicant: SUNSHINE LAKE PHARMA CO., LTD., Dongguan, Guangdong (CN)

(72) Inventors: Yingjun Zhang, Dongguan (CN); Chuanfei Jin, Dongguan (CN); Haiping Liang, Dongguan (CN); Chao Yi, Dongguan (CN); Ji Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 63 days.

(21) Appl. No.: 15/577,771

(22) PCT Filed: Jun. 2, 2016

(86) PCT No.: PCT/CN2016/084564
§ 371 (c)(1),
(2) Date: Nov. 29, 2017

(87) PCT Pub. No.: WO2016/192657
PCT Pub. Date: Dec. 8, 2016

(65) Prior Publication Data
US 2018/0179188 A1 Jun. 28, 2018

(30) Foreign Application Priority Data
Jun. 3, 2015 (CN) .......................... 2015 1 0299158

(51) Int. Cl.
| | |
|---|---|
| *C07D 401/12* | (2006.01) |
| *C07D 403/12* | (2006.01) |
| *C07D 413/12* | (2006.01) |
| *C07D 417/12* | (2006.01) |
| *A61K 45/06* | (2006.01) |
| *A61P 25/28* | (2006.01) |
| *A61K 31/496* | (2006.01) |
| *A61K 31/506* | (2006.01) |

(52) U.S. Cl.
CPC .......... *C07D 403/12* (2013.01); *A61K 31/496* (2013.01); *A61K 31/506* (2013.01); *A61K 45/06* (2013.01); *A61P 25/28* (2018.01); *C07D 401/12* (2013.01); *C07D 413/12* (2013.01); *C07D 417/12* (2013.01)

(58) Field of Classification Search
CPC .. C07D 401/12; C07D 403/12; C07D 413/12; C07D 417/12
See application file for complete search history.

(56) References Cited

U.S. PATENT DOCUMENTS

| | | |
|---|---|---|
| 3,188,313 A | 6/1965 | Archer |
| 3,381,009 A | 4/1968 | Palazzo et al. |
| 3,562,278 A | 2/1971 | Archer |
| 4,711,893 A | 12/1987 | Hausberg et al. |
| 4,954,502 A | 9/1990 | Smith et al. |
| 5,002,948 A | 3/1991 | Perregaard et al. |
| 5,010,079 A | 4/1991 | Manoury et al. |
| 5,077,293 A | 12/1991 | Smith et al. |
| 5,106,850 A | 4/1992 | Butcher et al. |
| 5,242,925 A | 9/1993 | Boettcher et al. |
| 5,270,312 A | 12/1993 | Glase et al. |
| 5,273,977 A | 12/1993 | Glase et al. |

(Continued)

FOREIGN PATENT DOCUMENTS

| | | |
|---|---|---|
| CN | 1844120 A | 10/2006 |
| CN | 102372703 A | 3/2012 |

(Continued)

OTHER PUBLICATIONS

Pessoa-Mahana et al., Synthesis, 5-hydroxytryptamine1A receptor affinity and docking studies of 3-[3-(4-aryl-1-piperazinyl)-propyl]-1H-indole derivatives, Chemical and Pharmaceutical Bulletin, 2012, 60(5): 632-638.

(Continued)

*Primary Examiner* — Brian E McDowell
(74) *Attorney, Agent, or Firm* — Kam Wah Law

(57) ABSTRACT

The invention relates to substituted piperazine compounds and methods of use and uses thereof, and further to the pharmaceutical compositions comprising the compounds and uses thereof, wherein the compound has Formula (I) or a stereoisomer, a tautomer, an N-oxide, a solvate, a metabolite, a pharmaceutically acceptable salt or a prodrug thereof. The substituted piperazine compounds and pharmaceutical compositions comprising the compounds disclosed herein can be used for inhibiting 5-hydroxytryptamine reuptake and/or stimulating 5-$HT_{1A}$ receptors. The invention also relates to processes for preparing these compounds and pharmaceutical compositions, and their uses in the treatment of a central nervous system dysfunction.

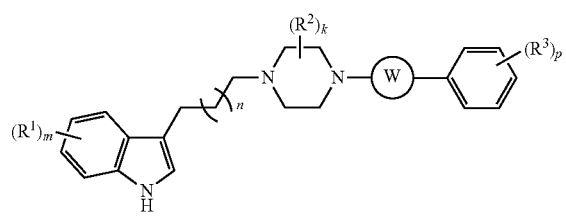

12 Claims, No Drawings

(56) References Cited

U.S. PATENT DOCUMENTS

| | | |
|---|---|---|
| 5,418,237 A | 5/1995 | Bottcher et al. |
| 5,434,154 A | 7/1995 | Smith et al. |
| 5,521,188 A | 5/1996 | Gylys et al. |
| 5,532,241 A | 7/1996 | Bottcher et al. |
| 5,614,524 A | 3/1997 | Matassa et al. |
| 5,618,816 A | 4/1997 | Crenshaw et al. |
| 5,629,323 A | 5/1997 | Cliffe et al. |
| 5,693,655 A | 12/1997 | Bottcher et al. |
| 5,725,838 A | 3/1998 | Pollak et al. |
| 5,763,444 A | 6/1998 | Smith et al. |
| 6,127,388 A | 10/2000 | Bourrain et al. |
| 6,251,908 B1 | 6/2001 | Bottcher et al. |
| 6,310,068 B1 | 10/2001 | Bottcher et al. |
| 6,391,882 B1 | 5/2002 | Moltzen et al. |
| 6,395,742 B1 | 5/2002 | Bosmans et al. |
| 6,399,616 B1 | 6/2002 | Peglion et al. |
| 6,476,035 B1 | 11/2002 | Moltzen et al. |
| 6,486,153 B1 | 11/2002 | Castro Pineiro et al. |
| 6,518,273 B1 | 2/2003 | Chapman et al. |
| 6,596,722 B2 | 7/2003 | Moltzen et al. |
| 6,699,864 B2 | 3/2004 | Ruhland et al. |
| 6,720,320 B2 | 4/2004 | Nishiyama |
| 6,727,264 B1 | 4/2004 | Marzabadi et al. |
| 7,067,513 B1 | 6/2006 | Van Hes et al. |
| 7,074,796 B2 | 7/2006 | Bang-Andersen et al. |
| 7,227,023 B2 | 6/2007 | Hatzenbuhler |
| 7,244,846 B2 | 7/2007 | Dorsch |
| 7,253,202 B2 | 8/2007 | Heinrich et al. |
| 7,262,216 B2 | 8/2007 | Holzemann et al. |
| 7,276,603 B2 | 10/2007 | Venkatesan |
| 7,425,574 B2 | 9/2008 | Holzemann et al. |
| 7,432,282 B2 | 10/2008 | Holzemann et al. |
| 7,495,111 B2 | 2/2009 | Ramamoorthy et al. |
| 7,829,565 B2 | 11/2010 | Heinrich et al. |
| 7,910,591 B2 | 3/2011 | Volk et al. |
| 7,968,551 B2 | 6/2011 | Schiemann et al. |
| 8,101,619 B2 | 1/2012 | Feenstra et al. |
| 8,138,174 B2 | 3/2012 | Lange et al. |
| 8,680,097 B2 | 3/2014 | Li et al. |
| 9,238,632 B2 | 1/2016 | Li et al. |
| 9,339,503 B2 | 5/2016 | Buchstaller et al. |
| 9,598,401 B2 | 3/2017 | Zhang et al. |
| 2004/0034219 A1 | 2/2004 | Mourelle Mancini |
| 2004/0044007 A1 | 3/2004 | Kehler et al. |
| 2006/0122175 A1 | 6/2006 | Hes et al. |
| 2006/0122191 A1 | 6/2006 | Heinrich |
| 2006/0160824 A1 | 7/2006 | Heinrich |
| 2007/0219209 A1 | 9/2007 | Volk et al. |
| 2007/0265300 A1 | 11/2007 | Volk et al. |
| 2009/0054454 A1 | 2/2009 | Venkatesan |
| 2009/0238761 A1 | 9/2009 | Campiani et al. |
| 2009/0318690 A1 | 12/2009 | Sasaki et al. |
| 2011/0059982 A1 | 3/2011 | Heinrich et al. |
| 2011/0306638 A1 | 12/2011 | Li |
| 2013/0064770 A1 | 3/2013 | Newington |
| 2015/0044293 A1 | 2/2015 | Rosen et al. |

FOREIGN PATENT DOCUMENTS

| | | |
|---|---|---|
| CN | 102850318 A | 1/2013 |
| CN | 102993186 A | 3/2013 |
| CN | 104163813 A | 11/2014 |
| CN | 104418842 A | 3/2015 |
| EP | 0387603 A1 | 9/1990 |
| WO | 9535293 A1 | 12/1995 |
| WO | 2004020437 A1 | 3/2004 |
| WO | 2004041815 A1 | 5/2004 |
| WO | 2007019867 A1 | 2/2007 |
| WO | 2012170209 A2 | 12/2012 |
| WO | 2013066831 A1 | 5/2013 |
| WO | 2013170741 A1 | 11/2013 |

OTHER PUBLICATIONS

Heinrich et al., Indolebutylamines as Selective 5-HT1A Agonists, Journal of Medicinal Chemistry, 2004, 47(19): 4677-4683.
Golubev et al., Synthesis and pharmacological properties of some 1-(2-quinolyl)-4-(indoly-3-alkyl)piperazines, Khimiko-Farmatsevtiches kii Zhurnal, 1981, 15(2): 88-90.
International Search Report of PCT/CN2016/084564.
Written Opinion of PCT/CN2016/084564.

SUBSTITUTED PIPERAZINE COMPOUNDS AND METHODS OF USE AND USE THEREOF

CROSS-REFERENCE TO RELATED APPLICATIONS

This is a U.S. national stage application of the International Patent Application No. PCT/CN2016/084564, filed Jun. 2, 2016, which claims priorities to Chinese Patent Application No. 201510299158.8, filed Jun. 3, 2015, both of which are incorporated herein by reference in their entirety.

FIELD OF THE INVENTION

The present invention belongs to the field of pharmaceutical technology, and more specifically relates to compounds, compositions for treating a central nervous system dysfunction and methods of use and uses thereof. Particularly, provided herein are substituted piperazine compounds acting as a 5-hydroxytryptamine reuptake inhibitor and/or a $5\text{-HT}_{1A}$ receptor agonist.

BACKGROUND OF THE INVENTION 5-hydroxytryptamine, a neurotransmitter that carries signal in the brain and nerves, plays a very important role in central nervous system (CNS) dysfunction, especially in anxiety disorder, depression, aggression and impulsivity. Regulation of the central nervous system dysfunction is possible either by antagonistic or agonistic action on a certain type of 5-hydroxytryptamine receptors. By now, at least 14 different 5-hydroxytryptamine receptors have been identified. These receptors can be divided into distinct families, independently recorded as $5\text{-HT}_1$, $5\text{-HT}_2$, $5\text{-HT}_3$, $5\text{-HT}_4$, $5\text{-HT}_5$, $5\text{-HT}_6$ and $5\text{-HT}_7$ with the subtypes in each family denoted by letters such as a, b and c. The $5\text{-HT}_{1A}$ receptor is a G-protein-coupled receptor widely distributed in regions that receives serotonergic input from the raphe nuclei: the frontal cortex, septum, amygdala, hippocampus, and hypothalamus. In these cortico-limbic regions, 5-HT1A is distributed post-synaptically. At the same time, the $5\text{-HT}_{1A}$ receptor also serves as the autoreceptor of presynaptic membrane on the raphe nuclei, reducing the discharge rate of neurons (i.e., the amount of 5-hydroxytryptamine released per action potential), and the synthesis of the neurotransmitter, and reducing the serotonergic activity of its projection areas. Activation of the presynaptic $5\text{-HT}_{1A}$ receptor may also indirectly reduce serotonergic transmission through the inhibition of tyrosine hydroxylase synthesis, as well as the activity of glutamatergic pathway that originates in the medial prefrontal cortex and projects to the raphe nuclei (Jonathan Savitz, Irwin Lucki, Wayne C. Drevets. $5\text{-HT}_{1A}$ receptor function in major depressive disorder. *Prog Neurobiol.* 2009, 88(1): 17-31).

Depression is the most important of all therapeutic indications related to 5-hydroxytryptamine disorder since it is the fourth leading burdensome disease in the world according to the World Health Organization. By 2020, depression is projected to rank second in all disability-adjusted life years. (Bromet E, Andrade L H, Hwang I, et al., Cross-national epidemiology of DSM-IV major depressive episode. *BMC Med.* 2011, 9: 90).

Historically, tricyclic antidepressants (TCAs) and monoamine oxidase inhibitors (MAOIs) revolutionized the pharmacologic treatment of a mood disorder in the 1950s, mostly by blocking neurotransmitter (dopamine, norepinephrine, and 5-hydroxytryptamine). However, the non-selective and undesired side effects limited their use. In 1980s, the discovery of selective 5-hydroxytryptamine reuptake inhibitors (SSRIs) changed the landscape. As a class, the SSRIs boast similar efficacy compared to the TCAs, and an improved AE profile with less tendency for toxicity in overdose (Sarko J. Andidepressant, old and new. A review of their adverse effects and toxicity in overdose. *Emerg Med Clin North Am,* 2000; 18 (4): 637-54, incorporated herein by reference).

Conventional SSRIs therapeutically increase available 5-hydroxytryptamine by inhibiting its reuptake and modulating its transmission. However, after using of SSRIs, administration of SSRIs also stimulates pre-synaptic $5\text{-HT}_{1A}$ autoreceptors, which decreases the release of 5-hydroxytryptamine and subsequently reduces 5-hydroxytryptamine concentrations in the synapse. However, after chronic administration, the stimulation of the $5\text{-HT}_{1A}$ autoreceptors is overcome via desensitization and the SSRIs are able to exert normal regulating effect. It is postulated that this stimulation of the autoreceptor is the causative factor in the delayed therapeutic effect of the SSRIs (Celada P, Puig M, Amargos-Bosch M, et al. The therapeutic role of $5\text{-HT}_{1A}$ and $5\text{-HT}_{2A}$ receptors in depression. *J Psychiatry Neurosci,* 2004, 29(4): 252-65). Thus, overcoming the negative feedback effect of $5\text{-HT}_{1A}$ autoreceptors antagonists held the promise of increasing and accelerating clinical antidepressant effects.

Compared to SSRIs, $5\text{-HT}_{1A}$ receptor agonists or partial agonists act directly on postsynaptic 5-hydroxytryptamine receptors to increase 5-hydroxytryptamine neurotransmission during the SSRI latency effect period. Feiger and Wilcox demonstrated that the buspirone and gepirone were clinically effective $5\text{-HT}_{1A}$ partial agonists (Feiger, A. Psychopharmacol. Bull. 1996, 32: 659-65, incorporated herein by reference). The addition of buspirone to standard SSRI treatment produced a marked improvement in patients previously unresponsive to standard treatment for depression (Dimitriou, E. J. *Clin. Psychopharmacol.,* 1998, 18: 465-9).

SUMMARY OF THE INVENTION

Provided herein are novel compounds believed to have clinical use in treating a CNS disorder through inhibiting selective 5-hydroxytryptamine reuptake and/or acting as $5\text{-HT}_{1A}$ receptor agonists. Preferred compounds disclosed herein are also believed to provide an improvement in potency, pharmacokinetic properties, and/or toxicity profile over certain other counterparts found in the art.

The invention relates to novel substituted piperazine compounds, the compounds have strong binding affinity to 5-HT transporters (SERT), and which can selectively inhibit the reuptake of 5-HT. In addition, the compounds also have strong binding affinity to $5\text{-HT}_{1A}$ receptors and can stimulate it effectively, thus which can be used in the manufacture of a medicament for treating a central nervous system (CNS) dysfunction. The compounds disclosed herein have stable properties and good salty, and advantages of pharmacodynamics and pharmacokinetics, such as a good brain plasma ratio, bioavailability or metabolic stability etc. Therefore, they hold the promise of clinical application.

The following just summarizes some aspects of the invention, but is not a limitation of the invention. These aspects and other parts are described more fully below. All references cited in this specification are incorporated herein by reference in their entirety. Where there are differences between the disclosure of the present specification and the cited references, the disclosure of the present specification shall controls.

Provided herein are novel compounds having a selective inhibition of 5-hydroxytryptamine reuptake and/or an agonistic effect on 5-$HT_{1A}$ receptors, which can be used in the preparation of medicaments for treating central nervous system (CNS) dysfunction, such as a depression disorder, an anxiety disorder and a bipolar disorder.

Provided herein also are methods for preparing the compounds and pharmaceutical compositions containing the compounds disclosed herein.

In one aspect, provided herein is a compound of Formula (I) or a stereoisomer, a tautomer, an N-oxide, a solvate, a metabolite, a pharmaceutically acceptable salt or a prodrug thereof,

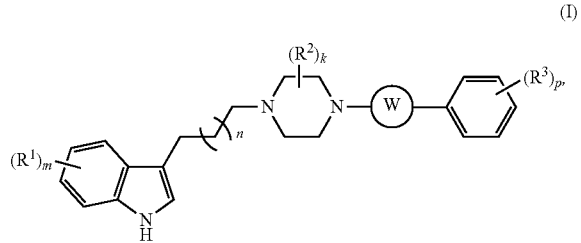

(I)

wherein:

W is a 5- to 6-membered heteroarylene ring, the 5- to 6-membered heteroarylene ring is optionally substituted with one, two, three, or four $R^x$ groups;

each $R^x$ is independently H, D, F, Cl, Br, I, —$NO_2$, —CN, —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, oxo (=O), $C_1$-$C_6$ alkyl, $C_2$-$C_6$ alkenyl, $C_2$-$C_6$ alkynyl or $C_1$-$C_6$ haloalkyl;

each $R^1$ is independently H, D, F, Cl, Br, I, —$NO_2$, —CN, —$NH_2$, —OH, —SH, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxy, ($C_1$-$C_6$ alkoxyl)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-;

each $R^2$ is independently H, D, F, Cl, $C_1$-$C_6$ alkyl, $C_1$-$C_6$ haloalkyl, —$NR^aR^b$, —$OR^c$, —C(=O)$R^d$, —C(=O)$OR^c$, —C(=O)$NR^aR^b$ or ($C_6$-$C_{10}$ aryl)-($C_1$-$C_6$ alkylene)-, or two adjacent $R^2$, together with the carbon atoms to which they are attached, form a $C_3$-$C_6$ carbocyclic ring, a benzene ring, a 3- to 7-membered heterocyclic ring or a 5- to 6-membered heteroaromatic ring, or two $R^2$ attached to one carbon atom, together with the carbon atom, form a $C_3$-$C_6$ carbocyclic ring or a 3- to 7-membered heterocyclic ring;

each $R^3$ is independently H, D, F, Cl, Br, I, —$NO_2$, —CN, —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)$OR^c$, —N($R^a$)C(=O)$NR^aR^b$, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, or two adjacent $R^3$, together with the carbon atoms to which they are attached, form a methylenedioxy or ethylenedioxy group, wherein each —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)$OR^c$, —N($R^a$) C(=O)$NR^aR^b$, alkyl, alkenyl, alkynyl, haloalkyl, cycloalkyl, cycloalkylalkylene, heterocyclyl, heterocyclylalkylene, aryl, arylalkylene, heteroaryl, heteroarylalkylene, methylenedioxy and ethylenedioxy is optionally and independently substituted with one or more $R^4$ groups;

each $R^4$ is independently F, Cl, Br, I, —$NO_2$, —CN, —$N_3$, —$NH_2$, —OH, —SH, $C_1$-$C_4$ alkyl, $C_2$-$C_6$ alkenyl, $C_2$-$C_6$ alkynyl, $C_1$-$C_4$ haloalkyl, $C_1$-$C_4$ alkoxyl, $C_1$-$C_4$ haloalkoxy, $C_1$-$C_4$ alkylamino, $C_1$-$C_4$ alkylthio, $NH_2$—($C_1$-$C_4$ alkylene)-, HO—($C_1$-$C_4$ alkylene)-, HS—($C_1$-$C_4$ alkylene)-, ($C_1$-$C_4$ alkylamino)-($C_1$-$C_4$ alkylene)-, ($C_1$-$C_4$ alkoxyl)-($C_1$-$C_4$ alkylene)-, ($C_1$-$C_4$ alkylthio)-($C_1$-$C_4$ alkylene)-, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-;

each $R^a$ and $R^b$ is independently H, $C_1$-$C_6$ alkyl, $C_3$-$C_6$ alkenyl, $C_3$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-, or $R^a$ and $R^b$ together with the nitrogen atom to which they are attached, form a 3- to 7-membered heterocyclic ring;

each $R^c$ and $R^d$ is independently H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-;

each m and n is independently 0, 1, 2, 3, or 4;

k is independently 0, 1, 2, 3, 4, 5 or 6; and p is independently 0, 1, 2, 3, 4 or 5.

In one embodiment, W is one of the following heteroarylene rings:

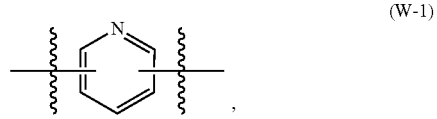

(W-1)

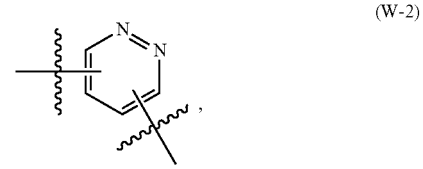

(W-2)

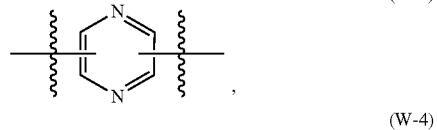

(W-3)

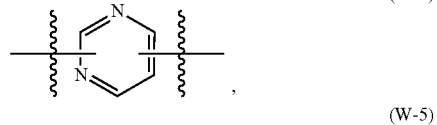

(W-4)

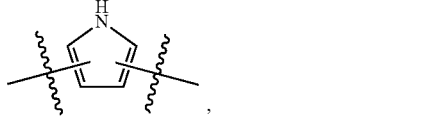

(W-5)

-continued (W-6) 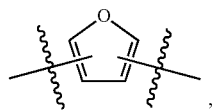, (W-7) 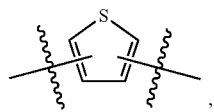, (W-8) 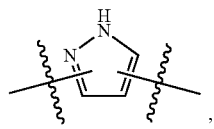, (W-9) 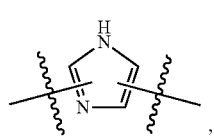, (W-10) 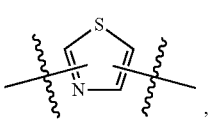, (W-11) , (W-12) 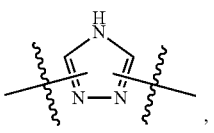, (W-13) 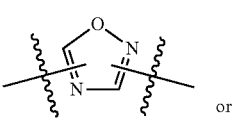 or (W-14) 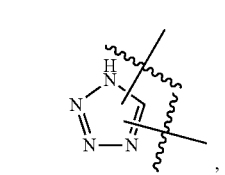, wherein each of Formula (W-1) to (W-14) is optionally and independently substituted with one, two, three or four $R^x$ groups; and each $R^x$ is as defined herein.

In one embodiment, provided herein is a compound of Formula (II) or a stereoisomer, a tautomer, an N-oxide, a solvate, a metabolite, a pharmaceutically acceptable salt or a prodrug thereof,

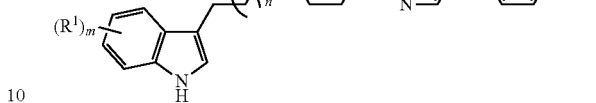
(II)

wherein X is CH or N;
r is independently 0, 1, 2 or 3; and
each $R^1$, $R^x$, $R^3$, m, n and p is as defined herein.

In another embodiment, provided herein is a compound of Formula (III) or a stereoisomer, a tautomer, an N-oxide, a solvate, a metabolite, a pharmaceutically acceptable salt or a prodrug thereof,

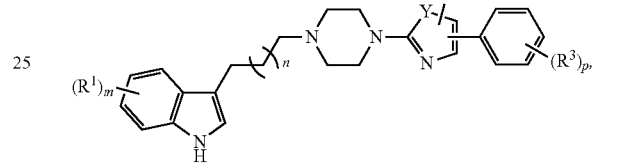
(III)

wherein Y is O, S or NH; and each $R^1$, $R^x$, $R^3$, m, n and p is as defined herein.

In another embodiment, provided herein is a compound of Formula (V) or Formula (VI), or a stereoisomer, a tautomer, an N-oxide, a solvate, a metabolite, a pharmaceutically acceptable salt or a prodrug thereof,

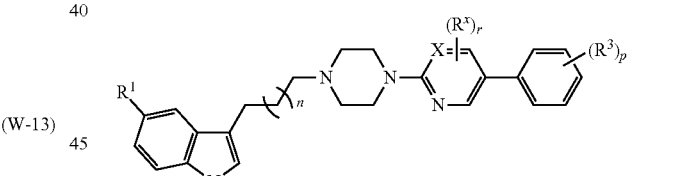
(V)

or

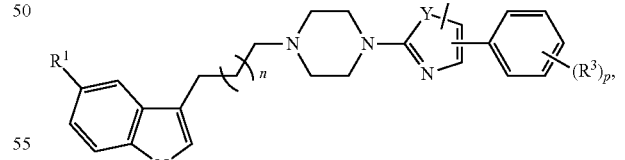
(VI)

wherein X is CH or N;
Y is O, S or NH;
r is independently 0, 1, 2 or 3; and each $R^1$, $R^x$, $R^3$, n and p is as defined herein.

In one embodiment, each $R^x$ of Formula (I), (II), (III), (V) or (VI) is independently H, D, F, Cl, —$NO_2$, —CN, —$NH_2$, —OH, -Me, -Et, -(n-Pr), -(i-Pr), -(t-Bu), —$CHF_2$, —$CF_3$, —$CH_2CF_3$, —$CF_2CHF_2$, —$CHFCF_3$, —$CF_2CF_3$, —$CF_2CH_2CH_3$, —$CF_2CH_2CF_3$, —$CF_2CH_2CHF_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, —OMe, —OEt, —O(i-Pr), —O(t-Bu), —NMe$_2$, —C(=O)H, —C(=O)OH, —C(=O)OMe, —C(=O)OEt, —C(=O)NH$_2$, —C(=O)NMe$_2$ or oxo (=O).

In one embodiment, each R$^1$ of Formula (I), (II), (III), (V) or (VI) is independently H, D, F, Cl, Br, —CN, —NO$_2$, —NH$_2$, —NMe$_2$, —OH, —OMe, —OEt, —O(i-Pr), —O(t-Bu), -Me, -Et, -(n-Pr), -(i-Pr), -(t-Bu) or —CF$_3$.

In one embodiment, each R$^2$ of Formula (I), (II), (III), (V) or (VI) is independently H, D, F, Cl, —NH$_2$, —OH, -Me, -Et, -(n-Pr), -(i-Pr), -(t-Bu), —CF$_3$, —OMe, —O(i-Pr) or —O(t-Bu).

In one embodiment, each R$^3$ of Formula (I), (II), (III), (V) or (VI) is independently H, D, F, Cl, Br, I, —NO$_2$, —CN, —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, C$_1$-C$_6$ alkyl, C$_2$-C$_6$ alkenyl, C$_2$-C$_6$ alkynyl, C$_1$-C$_6$ haloalkyl, C$_3$-C$_{10}$ cycloalkyl, (C$_3$-C$_{10}$ cycloalkyl)-(C$_1$-C$_6$ alkylene)-, 3- to 10-membered heterocyclyl, (3- to 10-membered heterocyclyl)-(C$_1$-C$_6$ alkylene)-, C$_6$-C$_{10}$ aryl, (C$_6$-C$_{10}$ aryl)-(C$_1$-C$_6$ alkylene)-, 5- to 10-membered heteroaryl or (5- to 10-membered heteroaryl)-(C$_1$-C$_6$ alkylene)-, or two adjacent R$^3$, together with the carbon atoms to which they are attached, form a methylenedioxy or ethylenedioxy group, wherein the —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, C$_1$-C$_6$ alkyl, C$_2$-C$_6$ alkenyl, C$_2$-C$_6$ alkynyl, C$_1$-C$_6$ haloalkyl, C$_3$-C$_{10}$ cycloalkyl, (C$_3$-C$_{10}$ cycloalkyl)-(C$_1$-C$_6$ alkylene)-, 3- to 10-membered heterocyclyl, (3- to 10-membered heterocyclyl)-(C$_1$-C$_6$ alkylene)-, C$_6$-C$_{10}$ aryl, (C$_6$-C$_{10}$ aryl)-(C$_1$-C$_6$ alkylene)-, 5- to 10-membered heteroaryl, (5- to 10-membered heteroaryl)-(C$_1$-C$_6$ alkylene)-, methylenedioxy and ethylenedioxy are each optionally and independently substituted with one or more R$^4$ groups; and each R$^a$, R$^b$, R$^c$, R$^d$ and R$^4$ is as defined herein.

In another embodiment, each R$^3$ of Formula (I), (II), (III), (V) or (VI) is independently H, F, Cl, —CN, —NO$_2$, —NH$_2$, —NMe$_2$, —NHEt, —NEt$_2$, —OH, —OMe, —OEt, —O(n-Pr), —O(i-Pr), —O(t-Bu), -Me, -Et, -(n-Pr), -(i-Pr), -(t-Bu), —CF$_3$, —CH$_2$CH$_2$Cl, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$, —OCH$_2$CF$_2$CHF$_2$, —CONH$_2$, —CONHMe, —CONMe$_2$, —C(=O)OMe, —C(=O)OEt, —NHC(=O)H, —NHC(=O)CH$_3$, —NHC(=O)OMe, —NHC(=O)CH$_2$OMe or phenyl.

In another embodiment, each R$^a$ and R$^b$ of Formula (I), (II), (III), (V) or (VI) is independently H, C$_1$-C$_4$ alkyl, C$_3$-C$_4$ alkenyl, C$_3$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5- to 7-membered heterocyclyl, (5- to 7-membered heterocyclyl)-(C$_1$-C$_4$ alkylene)-, phenyl, phenyl-(C$_1$-C$_4$ alkylene)-, 5- to 6-membered heteroaryl or (5- to 6-membered heteroaryl)-(C$_1$-C$_4$ alkylene)-, or R$^a$ and R$^b$ together with the nitrogen atom to which they are attached, form a 5- to 7-membered heterocyclic ring; and each R$^c$ and R$^d$ is independently H, C$_1$-C$_4$ alkyl, C$_2$-C$_4$ alkenyl, C$_2$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5- to 7-membered heterocyclyl, (5- to 7-membered heterocyclyl)-(C$_1$-C$_4$ alkylene)-, phenyl, phenyl-(C$_1$-C$_4$ alkylene)-, 5- to 6-membered heteroaryl or (5- to 6-membered heteroaryl)-(C$_1$-C$_4$ alkylene)-.

In another embodiment, each R$^a$ and R$^b$ of Formula (I), (II), (III), (V) or (VI) is independently H, -Me, -Et, -(n-Pr), -(i-Pr), -(t-Bu), —CF$_3$, —CH$_2$CH$_2$Cl, cyclopentyl, pyrrolidinyl, piperidinyl, morpholinyl or piperazinyl, or R$^a$ and R$^b$ together with the nitrogen atom to which they are attached, form a 5- to 6-membered heterocyclic ring; and each R$^c$ and R$^d$ is independently H, -Me, -Et, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl.

In other aspect, provided herein is a pharmaceutical composition comprising the compounds disclosed herein.

In one embodiment, the pharmaceutical composition disclosed herein further comprises a pharmaceutically acceptable excipient, carrier, adjuvant, or a combination thereof.

In one embodiment, the pharmaceutical composition disclosed herein further comprises a drug for treating a central nervous system dysfunction, the drug is an antidepressant drug, an antianxiety drug, a lithium drug as a mood stabilizer, an atypical antipsychotic drug, an antiepileptic drug, an anti-Parkinson's disease drug, a drug as a selective 5-hydroxytryptamine reuptake inhibitor and/or a 5-HT$_{1A}$ receptor agonist, a central nervous stimulant, a nicotinic antagonist or a combination thereof.

In another embodiment, the drug for treating a central nervous system dysfunction disclosed herein is amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, chlordiazepoxide, perphenazine or a combination thereof.

In other aspect, provided herein is use of the compound or the pharmaceutical composition disclosed herein in the manufacture of a medicament for preventing, treating or lessening a central nervous system dysfunction. For example, in one embodiment, the drug is used for preventing, treating or lessening a mammalian central nervous system dysfunction, and in another embodiment, the drug is used for preventing, treating or lessening a human central nervous system dysfunction.

In one embodiment, the central nervous system dysfunction is depression, anxiety, mania, schizophrenia, a bipolar disorder, a sleep disorder, an obsessive-compulsive disorder, a panic disorder, a post-traumatic stress disorder, a movement disorder, a sexual dysfunction, a musculoskeletal pain disorder, a cognitive disorder, a memory disorder, Parkinson's disease, Huntington's disease, a phobia, substance abuse or addiction, drug addiction withdrawal symptoms or premenstrual tension syndrome.

In other aspect, provided herein is use of the compound or the pharmaceutical composition disclosed herein in the manufacture of a medicament for inhibiting 5-hydroxytryptamine reuptake.

In other aspect, provided herein is use of the compound or the pharmaceutical composition disclosed herein in the manufacture of a medicament for activating partially 5-HT$_{1A}$ receptor.

In other aspect, provided herein is the compound or the pharmaceutical composition disclosed herein for use in preventing, treating or lessening a central nervous system dysfunction.

In one embodiment, the central nervous system dysfunction is depression, anxiety, mania, schizophrenia, a bipolar disorder, a sleep disorder, an obsessive-compulsive disorder, a panic disorder, a post-traumatic stress disorder, a movement disorder, a sexual dysfunction, a musculoskeletal pain disorder, a cognitive disorder, a memory disorder, Parkinson's disease, Huntington's disease, a phobia, substance abuse or addiction, drug addiction withdrawal symptoms or premenstrual tension syndrome.

In other aspect, provided herein is the compound or the pharmaceutical composition disclosed herein for use in inhibiting reuptaking 5-hydroxytryptamine and/or partially activating 5-HT$_{1A}$ receptors.

In other aspect, provided herein is a method for preventing, treating or lessening a central nervous system dysfunction in a subject comprising administering to the subject a therapeutically effective amount of the compound or the pharmaceutical composition disclosed herein.

In one embodiment, the central nervous system dysfunction is depression, anxiety, mania, schizophrenia, a bipolar disorder, a sleep disorder, an obsessive-compulsive disorder, a panic disorder, a post-traumatic stress disorder, a movement disorder, a sexual dysfunction, a musculoskeletal pain disorder, a cognitive disorder, a memory disorder, Parkinson's disease, Huntington's disease, a phobia, substance abuse or addiction, drug addiction withdrawal symptoms or premenstrual tension syndrome.

In other aspect, provided herein is a method for inhibiting reuptaking 5-hydroxytryptamine and/or partially activating 5-HT$_{1A}$ receptors in a subject comprising administering to the subject a therapeutically effective amount of the compound or the pharmaceutical composition disclosed herein.

In another aspect, provided herein are methods for preparing, separating, and purifying the compounds represented by Formula (I), (II), (III), (V) or (VI).

Biological test results show that the compounds of the present invention have strong affinity for human-derived 5-HT transporter (SERT) and 5-HT$_{1A}$ receptor; meanwhile the compounds of the present invention have preferable pharmacokinetic properties in rats, dogs and monkeys, and certain distribution in plasma, brain tissue and cerebrospinal fluid of rats, thus the compounds provided herein can be used as preferable selective 5-hydroxytryptamine reuptake inhibitors and/or 5-HT$_{1A}$ receptor agonists.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

All references cited in the present invention are hereby incorporated by reference in their entirety, and in case of there are inconsistencies between the incorporated references and the present inventive, the present disclosure will prevail. In addition, all terms and phrases used herein have the general meaning known to those skilled in the art. Even so, it is still desired for making a more detailed explanation to the terms and phrases in the present invention. In case of there are inconsistencies between mentioned terms and phrases and well known meaning, the present disclosure will prevail. The following definitions of general terms used in the present description apply irrespective of whether the terms in question appear alone or in combination.

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, include but are not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of Example, "a component" means one or more components, and thus, possibly, more than one component is contemplated and may be employed or used in an implementation of the described embodiments.

As described herein, compounds disclosed herein may optionally be substituted with one or more substituents, such as are illustrated generally below, or as exemplified by particular classes, subclasses, and species of the invention.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

In general, the term "substituted" refers to the replacement of one or more hydrogen radicals in a given structure with the radical of a specified substituent. Unless otherwise indicated, a substituted group may have a substituent at each substitutable position of the group. When more than one position in a given structure can be substituted with more than one substituent selected from a specified group, the substituent may be either the same or different at each position.

The term "unsubstituted" means that the specified group bears no substituent.

The terms "optionally substituted" and "unsubstituted or substituted" can be used interchangeably herein, which mean that the structure is unsubstutited or substitutited by one or more substituents disclosed herein, and the substituents disclosed herein include, but are not limited to D, F, Cl, $N_3$, —CN, —OH, —SH, —$NH_2$, alkyl, alkoxy, alkylthio, alkylamino, cycloalkyl, heterocyclyl, aryl, heteroaryl, and the like.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

The term "unsaturated" refers to a moiety having one or more units of unsaturation.

The term "comprise" is an open expression, it means comprising the contents disclosed herein, but don't exclude other contents.

At various places in the present specification, substituents of compounds disclosed herein are disclosed in groups or in ranges. It is specifically intended that the invention includes each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The terms "halogen" and "halo" are used interchangeably in this invention, and refer to Fluoro (F), Chloro (CO, Bromo (Br), or Iodo (I).

The term "alkyl" or "alkyl group" refers to a saturated linear or branched-chain monovalent hydrocarbon radical of 1 to 20 carbon atoms. Unless otherwise stated, the alkyl group contains 1-20 carbon atoms. In some embodiments, the alkyl group contains 1-10 carbon atoms; in other embodiments, the alkyl group contains 1-8 carbon atoms; in still other embodiments, the alkyl group contains 1-6 carbon atoms; in yet other embodiments, the alkyl group contains 1-4 carbon atoms; in still yet embodiments, the alkyl group contains 1-3 carbon atoms. The alkyl group is optionally substituted with one or more substituents described herein.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, n-heptyl and n-octyl, etc.

The term "alkylene" refers to a saturated divalent hydrocarbon group derived from a straight or branched chain saturated hydrocarbon by the removal of two hydrogen atoms. Unless otherwise stated, the alkylene group contains 1-10 carbon atoms. In some embodiments, the alkylene group contains 1-6 carbon atoms. In other embodiments, the alkylene group contains 1-4 carbon atoms. In still other embodiments, the alkylene group contains 1-2 carbon atoms. Such examples include, but are not limited to methylene (—$CH_2$—), ethylene (—$CH_2CH_2$—), isopropylene (—$CH(CH_3)CH_2$—), and the like. Wherein the alkylene group is optionally substituted with one or more substitutents described herein.

The term "alkenyl" refers to a monovalent hydrocarbon radical having at least one unsaturated carbon-carbon double bond ($SP^2$) site and a linear or branched chain containing 2 to 12 carbon atoms, and it contains a "cis" and "trans" orientations, or "E" and "Z" orientations. In some embodiments, the alkenyl contains 2 to 8 carbon atoms. In other embodiments, the alkenyl contains 2 to 6 carbon atoms. In still other embodiments, the alkenyl contains 2 to 4 carbon atoms. Examples of alkenyl groups include, but are not limited to, ethylenyl or vinyl (—CH=$CH_2$), allyl (—$CH_2$CH=$CH_2$), and the like. The alkenyl group is optionally substituted with one or more substituents described herein.

The term "alkynyl" refers to a monovalent hydrocarbon radical having at least one unsaturated carbon-carbon triple bond (SP) site and a linear or branched chain containing 2 to 12 carbon atoms. In some embodiments, the alkynyl contains 2 to 8 carbon atoms. In other embodiments, the alkynyl contains 2 to 6 carbon atoms. In still other embodiments, the alkynyl contains 2 to 4 carbon atoms. Examples of alkynyl groups include, but are not limited to, ethynyl (—C≡CH), propargyl (—$CH_2$C≡CH), 1-propynyl (—C≡C—$CH_3$), and the like. The alkynyl group is optionally substituted with one or more substituents described herein.

The term "alkoxy" refers to an alkyl group, as previously defined, attached to the parent molecular moiety via an oxygen atom. Unless otherwise stated, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms.

The alkoxy radicals are optionally substituted with one or more substituents described herein.

Some non-limiting examples of the alkoxy group include methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "haloalkyl" or "haloalkoxy" respectively refers to an alkyl or alkoxy group, as the case may be, substituted with one or more halogen atoms, and wherein each of the alkyl or alkoxy is defined as described herein. Examples of such groups include, but are not limited to, chloromethyl, trifluoromethyl, trifluoroethyl, trifluoromethoxy, and the like. The haloalkyl or haloalkoxy group is optionally substituted with one or more substituents described herein.

The term "alkylamino" refers to "N-alkylamino" and "N,N-dialkylamino", wherein amino groups are independently substituted with one alkyl radical or two alkyl groups, respectively. In some embodiments, the alkylamino group is a "lower alkylamino" radical having one or two $C_1$-$C_6$ alkyl groups attached to a nitrogen atom. In other embodiments, the alkylamino group is a lower alkylamino group having 1 to 4 carbon atoms. Some non-limiting examples of suitable alkylamino radical include mono or dialkylamino. Some examples include, but are not limited to, N-methylamino, N-ethylamino, N,N-dimethylamino and N,N-diethylamino, and the like. And wherein the alkylamino radical is optionally substituted with one or more substituents described herein.

The term "alkylthio" refers to a radical containing a linear or branched-alkyl radical of 1 to 10 carbon atoms, attached to a divalent sulfur atom. In some embodiments, the alkylthio group is a lower alkylthio group having 1 to 4 carbon atoms. Some non-limiting examples of "alkylthio" include, but are not limited to, methylthio (CH$_3$S—). Wherein the alkylthio radical is optionally substituted with one or more substitutents described herein.

The term "carbocycle", "carbocyclyl", or "cycloaliphatic" refers to a monocyclic, bicyclic or tricyclic ring system containing 3 to 12 carbon atoms having one or more sites attached to the rest of the molecule, wherein the ring may be saturated or contains one or more units of unsaturation, but one aromatic ring can not exist in the ring. Some non-limiting examples of the cycloaliphatic group include cycloalkyl, cycloalkenyl and cycloalkynyl. Further examples of the cycloaliphatic group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, and the like. Wherein the carbocyclyl group is optionally substituted with one or more substituents described herein.

The term "cycloalkyl" refers to a monovalent or multivalent saturated ring having 3 to 12 carbon atoms as a monocyclic, bicyclic, or tricyclic ring system. And wherein the bicyclic or tricyclic ring system may include fused ring, briged ring and spiro ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. The cycloalkyl radical is optionally substituted with one or more substituents described herein.

The term "cycloalkylalkylene" refers to a cycloalkyl group, attached to the rest part of the molecule through an alkylene group. Wherein the alkylene group and the cycloalkyl group are as defined herein. In some embodiments, the "cycloalkylalkylene group" refers to a "lower alkylene" group having a cycloalkyl group attached to an alkylene group which has one to six carbon atoms. In some other embodiments, a cycloalkyl group attached to an alkylene group which has one to four carbon atoms. In still other embodiments, a cycloalkyl group attached to an alkylene group which has 1 to 3 carbon atoms. The cycloalkylalkylene group is optionally substituted with one or more substituents described herein.

The term "heteroatom" refers to one or more of oxygen (O), sulfur (S), nitrogen (N), phosphorus (P), or silicon (Si), including any oxidized form of nitrogen (N), sulfur (S), or phosphorus (P); the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "heterocyclic ring", "heterocyclyl" or "heterocyclic" as used interchangeably herein refers to a monovalent or multivalent monocyclic, bicyclic or tricyclic ring containing 3 to 14 carbon atoms, wherein each one or more atoms in the ring is independently replaced by heteroatoms, the heteroatom is as defined herein, and the ring may be saturated or contains one or more units of unsaturation, but one aromatic ring can not exist in the ring. In some embodiments, "heterocyclic ring", "heterocyclyl" or "heterocyclic" group is a monocyclic ring having 3 to 8 ring members (e.g., 2 to 6 carbon atoms and 1 to 3 heteroatoms selected from N, O, P and S, wherein the S or P is optionally substituted with one or more oxo to provide the group SO or SO$_2$, PO or P$_{O2}$, when the ring is a 3-membered ring, there is only one heteroatom), or a bicyclic ring having 7 to 12 ring members (e.g., 4 to 9 carbon atoms and 1 to 3 heteroatoms selected from N, O, P and S, wherein the S or P is optionally substituted with one or more oxo to provide the group SO or SO$_2$, PO or PO$_2$), and wherein the carbocyclyl group is optionally substituted with one or more substituents described herein.

The heterocyclyl may be a carbon radical or heteroatom radical, of which a —CH$_2$— group can optionally be replaced by a —C(=O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of the heterocyclyl group of which the ring sulfur atom is oxidized include sulfolanyl, 1,1-dioxo-thiomorpholinyl, and the like. And wherein the carbocyclyl group is optionally substituted with one or more substituents described herein.

The term "heterocyclylalkylene" refers to a heterocyclyl group, attached to the rest part of the molecule through an alkylene group. Wherein the alkylene group and the heterocyclyl group are as defined herein. In some embodiments, the "heterocyclylalkylene group" refers to a "lower heterocyclylalkylene" group having a heterocyclyl group attached to an alkylene group which has 1 to 6 carbon atoms. In some other embodiments, a heterocyclyl group attached to an alkylene group which has 1 to 4 carbon atoms. Some non-limiting examples of such group include, but are not limited to, pyrrolidin-2-ylmethylene-, 2-(pyrrolidin-2-yl) ethylidene-, etc. And the heterocyclylalkylene group is optionally substituted with one or more substituents described herein.

The term "aryl" refers to a monovalent or multivalent monocyclic, bicyclic, or tricyclic carbocyclic ring system having a total of 6 to 14 ring members, preferably, 6 to 10 ring members, and more preferably 6 ring members, and wherein at least one ring in the system is aromatic. The aryl group is generally, but not necessarily bonded to the parent molecule through an aromatic ring of the aryl group. The terms "aryl" and "aromatic ring" can be used interchangeably herein. Examples of aryl group may include phenyl, naphthyl, anthracene, and the like. The aryl radical is optionally substituted with one or more substituents described herein.

The term "arylalkylene" refers to an aryl group, attached to the rest of the molecule through an alkylene group. Wherein the alkylene group and the alkylene group are as defined herein. In some embodiments, the arylalkylene group refers to a "lower arylalkylene" group having an aryl group attached to an alkylene group which has 1 to 6 carbon atoms. In some other embodiments, arylalkylene group refers to a "phenylalkylene" having an alkylene group containing 1 to 4 carbon atoms. Some non-limiting examples include benzyl, 2-phenylethylidene, and the like. And the arylalkylene group is optionally substituted with one or more substituents described herein.

The term "heteroaryl" refers to a monovalent or multivalent monocyclic, bicyclic, or tricyclic ring system having a total of 5 to 14 ring members, preferably, 5 to 10 ring members, and more preferably 5 to 6 ring members, and wherein at least one ring in the system is aromatic, and at least one ring contains one or more heteroatoms. The heteroaryl group is generally, but not necessarily bonded to the parent molecule through an aromatic ring of the heteroaryl group. The term "hetreroaryl", "heteroaromatic ring" or "heteroaromatic compound" can be used interchangeably herein. The heteroaryl group is optionally substituted with one or more substituents disclosed herein. In some embodiments, a 5- to 10-membered heteroaryl group contains 1, 2, 3 or 4 heteroatoms independently selected from O, S and N; in some other embodiments, 5- to 6-membered heteroaryl is monocyclic ring system and contains 1, 2, 3 or 4 heteroatoms independently selected from O, S and N.

Some non-limiting examples of the heteroaryl ring include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the like; and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, and the like.

The term "heteroarylalkylene" refers to a heteroaryl group, attached to the rest of the molecule through an alkylene group. Wherein the alkylene group and the heteroaryl group are as defined herein. In some embodiments, the heteroarylalkylene group refers to a "lower heteroarylalkylene" group having a heteroaryl group attached to an alkylene group which has 1 to 6 carbon atoms. In some other embodiments, a heteroaryl group attached to an alkylene group which has one to four carbon atoms. Some non-limiting examples include pyridine-2-ylmethylene-, 2-(furfuran-3-yl)ethylidene-, and the like. The heteroarylalkylene group is optionally substituted with one or more substituents described herein.

The terms "carboxy" or "carboxyl" refers to —C(=O)— can be used alone or with other terms; the term "acyl" refers to —C(=O)—R; the term "amide group" refers to —NH—C(=O)—R; the term "carbamoyl" refers to —C(=O)NH₂.

As described herein, when two attachment points within a ring system attach to the rest of the molecule, both rest groups of the molecule can attach interchangeably to the two attachment points. Such as shown in Formula a, the ring attaches to the rest of the molecule through E and E', and the group attached to E can interchange with the group attached to E', as shown in Formual a-1 and Formula a-2.

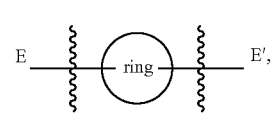

Formula a

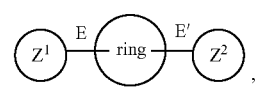

Formula a-1

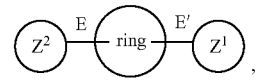

Formula a-2

As described herein, a bond drawn from a substituent R to the center of one ring within a ring system (shown in Formula b) represents substitution of the substituent R at any substitutable position on the ring (shown in B ring of Formula b). For example, Formula b represents the B ring may be substituted at any substitutable position by the substituent R, as shown in Formula c, d and e.

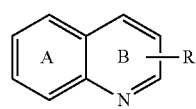

Formula b

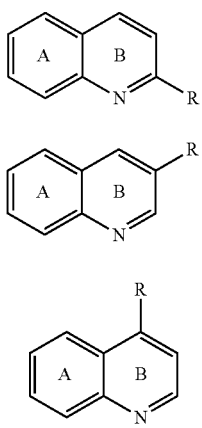

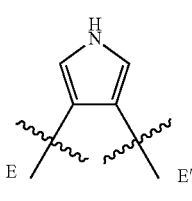

Formula c

Formula d

Formula e

As described herein, the attachment points can attach to the rest of the molecule at any attachable position on the ring, meanwhile, the attachment points can be used interchangeably with each other. For example, Formula f represents any connectable site on the pyrrole ring can be used as the attachment points attached the rest of the molecule as shown in Formula g, h, i, j, k and l, and E and E' can be used interchangeably with each other.

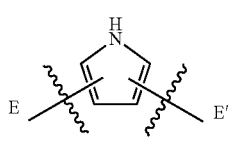

Formula f

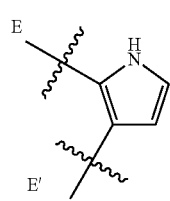

Formula g

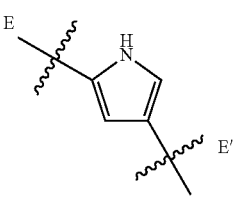

Formula h

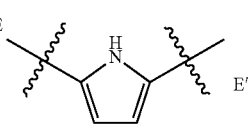

Formula i

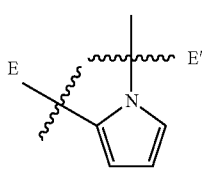

Formula j

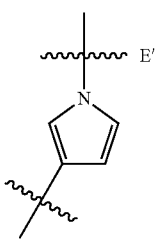

Formula k

Formula l

As used herein, the term "subject" refers to an animal. Typically the animal is a mammal, includes a human. A subject also refers to for example, primates (e.g., humans, male or female), cows, sheep, goats, horses, dogs, cats, rabbits, rats, mice, fish, birds and the like. In some embodiments, the subject is a primate. In some other embodiments, the subject is a human.

As used herein, "patient" refers to a human (including adults and children) or other animal. In some embodiment, "patient" refers to a human.

The term "stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

The term "chiral" refers to molecules which have the property of non-superimposability of the mirror image partner, while the term "achiral" refers to molecules which are superimposable on their mirror image partner.

The term "racemate" or "racemic mixture" refers to a 50:50 mixture of enantiomers which lacks optical activity.

The term "enantiomers" refers to two stereoisomers of a compound which are non-superimposable mirror images of one another.

The term "diastereomer" refers to a stereoisomer with two or more centers of chirality and whose molecules are not mirror images of one another. Diastereomers have different physical properties, e.g. melting points, boling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994, all of which are incorporated herein by reference. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, wherein (−) or l means that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Cis and trans isomers are diastereomer.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* ($2^{nd}$ Ed. Robert E. Gawley, Jeffrey Aube, Elsevier, Oxford, UK, 2012); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

Unless otherwise stated, structures depicted herein are also meant to include all isomeric (e.g., enantiomeric, diastereomeric, and geometric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The term "pharmaceutically acceptable" as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "prodrug" refers to a compound that is transformed in vivo into a compound of Formula (I) to (VI). Such a transformation can be affected, for example, by hydrolysis of the prodrug form in blood or enzymatic transformation to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, Journal of Medicinal Chemistry, 2008, 51, 2328-2345, each of which is incorporated herein by reference.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Some non-limiting examples of suitable hydroxy-protecting groups include trialkylsilyl, acetyl, benzoyl, and benzyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl) ethoxy-methy-1, 2-(p-toluenesulfonyl) ethyl, 2-(p-nitrophenylsulfenyl)-ethyl, 2-(diphenylphosphino)-ethyl, nitroethyl and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_1$-$C_8$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, ethanolamine and the mixture thereof. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "therapeutically effective amount" refers to the amount of a compound that, when administered to a subject for treating a disease, is sufficient to effect such treatment for the disease. The "therapeutically effective amount" will vary depending on the compound, the disease and its severity and the condition, age, weight, etc., of the patient to be treated.

"Treating" or "treatment" of a disease state includes: (1) preventing the disease state, i.e., causing the clinical symptoms of the disease state not to develop in a subject that may be exposed to or predisposed to the disease state, but does not yet experience or display symptoms of the disease state; (2) inhibiting the disease state, i.e., arresting the development of the disease state or its clinical symptoms, or (3) relieving the disease state, i.e., causing temporary or permanent regression of the disease state or its clinical symptoms.

DESCRIPTION OF COMPOUNDS OF THE INVENTION

The present invention relates to piperazine compounds, and the pharmaceutically acceptable salts, pharmaceutical formulation and composition thereof, which can be used as a selective 5-hydroxytryptamine reuptake inhibitor and/or a 5-$HT_{1A}$ receptor agonist, and have potential uses in the treatment of a central nervous system (CNS) dysfunction, such as depression, an anxiety disorder and a bipolar disorder.

In one aspect, provided herein is a compound having Formula (I) or a stereoisomer, a tautomer, an N-oxide, a solvate, a metabolite, a pharmaceutically acceptable salt or a prodrug thereof,

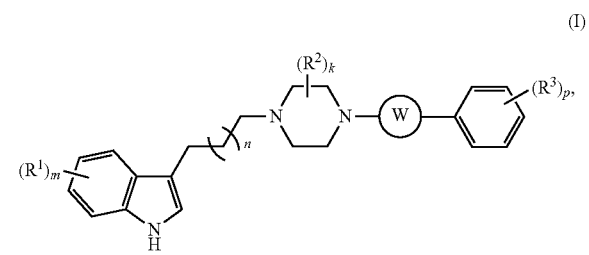

(I)

wherein, each $R^1$, $R^2$, $R^3$, W, m, n, k and p is as defined herein.

In one embodiment, W is a 5- to 6-membered heteroarylene ring, the 5- to 6-membered heteroarylene ring is optionally substituted with one, two, three, or four $R^x$ groups; and $R^x$ is as defined herein.

In one embodiment, each $R^x$ is dependently H, D, F, Cl, Br, I, —$NO_2$, —CN, —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, oxo (=O), $C_1$-$C_6$ alkyl, $C_2$-$C_6$ alkenyl, $C_2$-$C_6$ alkynyl or $C_1$-$C_6$ haloalkyl; and each $R^a$, $R^b$, $R^c$ and $R^d$ is as defined herein.

In one embodiment, each $R^1$ is independently H, D, F, Cl, Br, I, —$NO_2$, —CN, —$NH_2$, —OH, —SH, $C_1$-$C_6$ alkyl, $C_2$-$C_6$ alkenyl, $C_2$-$C_6$ alkynyl, $C_1$-$C_6$haloalkyl, $C_1$-$C_6$ alkoxyl, $C_1$-$C_6$ haloalkoxy, ($C_1$-$C_6$ alkoxyl)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-.

In one embodiment, each $R^2$ is independently H, D, F, Cl, $C_1$-$C_6$ alkyl, $C_1$-$C_6$ haloalkyl, —$NR^aR^b$, —$OR^d$, —C(=O)$R^d$, —C(=O)$OR^c$, —C(=O)$NR^aR^b$ or ($C_6$-$C_{10}$ aryl)-($C_1$-$C_6$ alkylene)-, or two adjacent $R^2$, together with the carbon atoms to which they are attached, form a $C_3$-$C_6$ carbocyclic ring, a benzene ring, a 3- to 7-membered heterocyclic ring or a 5- to 6-membered heteroaromatic ring, or two $R^2$ attached to one carbon atom, together with the carbon atom, form a $C_3$-$C_6$ carbocyclic ring or a 3- to 7-membered heterocyclic ring; and each $R^a$, $R^b$, $R^c$ and $R^d$ is as defined herein.

In one embodiment, each $R^3$ is dependently H, D, F, Cl, Br, I, —$NO_2$, —CN, —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)$OR^c$, —N($R^a$)C(=O)$NR^aR^b$, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, or two adjacent $R^3$, together with the carbon atoms to which they are attached, form a methylenedioxy or ethylenedioxy group, wherein each —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)$OR^c$, —N($R^a$)C(=O)$NR^aR^b$, alkyl, alkenyl, alkynyl, haloalkyl, cycloalkyl, cycloalkylalkylene, heterocyclyl, heterocyclylalkylene, aryl, arylalkylene, heteroaryl, heteroarylalkylene, methylenedioxy and ethylenedioxy is optionally and independently substituted with one or more $R^4$ groups;

each $R^a$, $R^b$, $R^c$, $R^d$ and $R^4$ is as defined herein.

In one embodiment, each $R^4$ is dependently F, Cl, Br, I, —$NO_2$, —CN, —$N_3$, —$NH_2$, —OH, —SH, $C_1$-$C_4$ alkyl, $C_2$-$C_6$ alkenyl, $C_2$-$C_6$ alkynyl, $C_1$-$C_4$ haloalkyl, $C_1$-$C_4$ alkoxyl, $C_1$-$C_4$ haloalkoxy, $C_1$-$C_4$ alkylamino, $C_1$-$C_4$ alkylthio, $NH_2$—($C_1$-$C_4$ alkylene)-, HO—($C_1$-$C_4$ alkylene)-, HS—($C_1$-$C_4$ alkylene)-, ($C_1$-$C_4$ alkylamino)-($C_1$-$C_4$ alkylene)-, ($C_1$-$C_4$ alkoxyl)-($C_1$-$C_4$ alkylene)-, ($C_1$-$C_4$ alkylthio)-($C_1$-$C_4$ alkylene)-, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene), phenyl, phenyl-($C_1$-$C_4$ alkylene)-, 5- to 6-membered heteroaryl or (5- to 6-membered heteroaryl)-($C_1$-$C_4$ alkylene)-.

In one embodiment, each $R^a$ and $R^b$ is independently H, $C_1$-$C_6$ alkyl, $C_3$-$C_6$ alkenyl, $C_3$-$C_6$ alkynyl, $C_1$-$C_6$ haloalkyl, $C_3$-$C_4$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-, or $R^a$ and $R^b$ together with the nitrogen atom to which they are attached, form 3- to 7-membered heterocyclic ring; and each $R^c$ and $R^d$ is independently H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-.

In one embodiment, each m is independently 0, 1, 2, 3, or 4.

In one embodiment, each n is independently 0, 1, 2, 3, or 4.

In one embodiment, each k is independently 0, 1, 2, 3, 4, 5 or 6.

In one embodiment, each p is independently 0, 1, 2, 3, 4 or 5.

In one embodiment, W is one of the following heteroarylene rings:

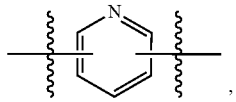
(W-1)

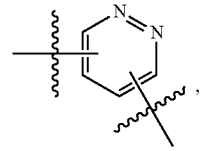
(W-2)

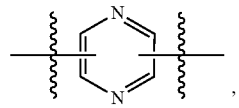
(W-3)

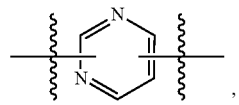
(W-4)

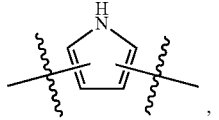
(W-5)

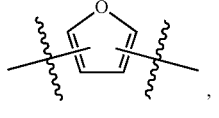
(W-6)

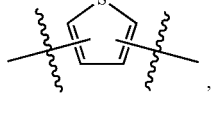
(W-7)

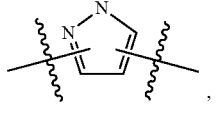
(W-8)

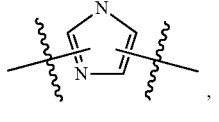
(W-9)

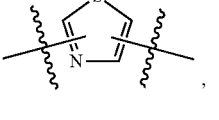
(W-10)

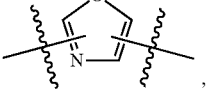
(W-11)

-continued

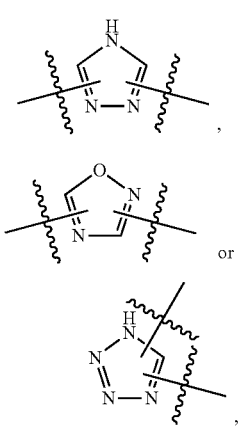

wherein each of Formula (W-1) to (W-14) is optionally and independently substituted with one, two, three or four $R^x$ groups; and each $R^x$ is as defined herein.

In one embodiment, provided herein is a compound having Formula (II) or a stereoisomer, a tautomer, an N-oxide, a solvate, a metabolite, a pharmaceutically acceptable salt or a prodrug thereof,

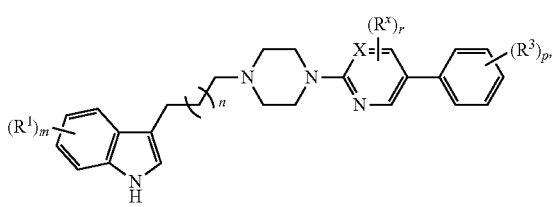

wherein X is CH or N;
r is 0, 1, 2 or 3; and
each $R^1$, $R^x$, $R^3$, m, n and p is as defined herein.

In one embodiment, provided herein is a compound having Formula (III) or a stereoisomer, a tautomer, an N-oxide, a solvate, a metabolite, a pharmaceutically acceptable salt or a prodrug thereof,

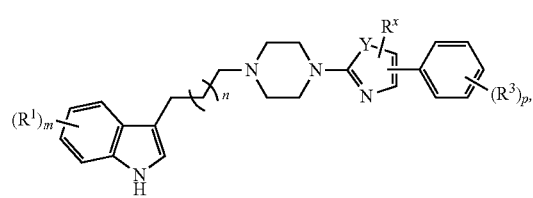

wherein Y is O, S or NH; and
each $R^1$, $R^x$, $R^3$, m, n and p is as defined herein.

In yet another embodiment, provided herein is a compound having Formula (IV) or a stereoisomer, a tautomer, an N-oxide, a solvate, a metabolite, a pharmaceutically acceptable salt or a prodrug thereof,

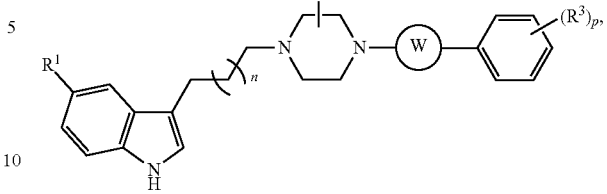

wherein each $R^1$, $R^2$, $R^3$, W, n, k and p is as defined herein.

In yet another embodiment, provided herein is a compound having Formula (V) or a stereoisomer, a tautomer, an N-oxide, a solvate, a metabolite, a pharmaceutically acceptable salt or a prodrug thereof,

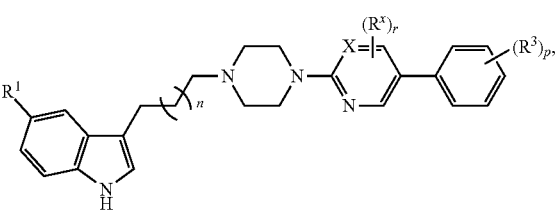

wherein X is CH or N;
r is 0, 1, 2 or 3; and
each $R^1$, $R^x$, $R^3$, n and p is as defined herein.

In yet another embodiment, provided herein is a compound having Formula (VI) or a stereoisomer, a tautomer, an N-oxide, a solvate, a metabolite, a pharmaceutically acceptable salt or a prodrug thereof,

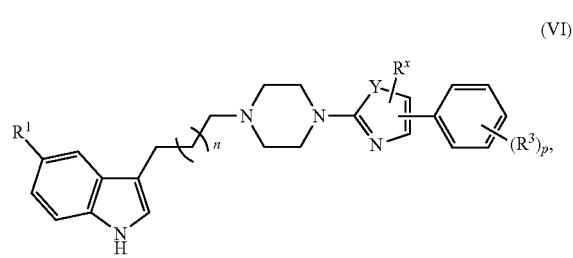

wherein Y is O, S or NH; and
each $R^1$, $R^x$, $R^3$, n and p is as defined herein.

In one embodiment, each $R_x$ is independently H, D, F, Cl, —NO$_2$, —CN, —NH$_2$, —OH, -Me, -Et, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, —OMe, —OEt, —O(i-Pr), —O(t-Bu), —NMe$_2$, —C(=O)H, —C(=O)OH, —C(=O)OMe, —C(=O)OEt, —C(=O)NH$_2$, —C(=O)NMe$_2$ or oxo (=O).

In one embodiment, each $R^1$ is independently H, D, F, Cl, Br, —CN, —NO$_2$, —NH$_2$, —NMe$_2$, —OH, —OMe, —OEt, —O(i-Pr), —O(t-Bu), -Me, -Et, -(n-Pr), -(i-Pr), -(t-Bu) or —CF$_3$.

In another embodiment, each $R^2$ is independently H, D, F, Cl, —NH$_2$, —OH, -Me, -Et, -(n-Pr), -(i-Pr), -(t-Bu), —CF$_3$, —OMe, —O(i-Pr) or —O(t-Bu).

In one embodiment, each $R^3$ is independently H, D, F, Cl, Br, I, —$NO_2$, —CN, —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)$OR^c$, —N($R^a$)C(=O)$NR^aR^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3- to 10-membered heterocyclyl, (3- to 10-membered heterocyclyl)-($C_1$-$C_6$ alkylene)-, $C_6$-$C_{10}$ aryl, ($C_6$-$C_{10}$ aryl)-($C_1$-$C_6$ alkylene)-, 5- to 10-membered heteroaryl or (5- to 10-membered heteroaryl)-($C_1$-$C_6$ alkylene)-, or two adjacent $R^3$, together with the carbon atoms to which they are attached, form a methylenedioxy or ethylenedioxy group, wherein each —$NR^aR^b$, —$OR^c$, —$SR^c$, —C(=O)$R^d$, —C(=O)$OR^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)$OR^c$, —N($R^a$)C(=O)$NR^aR^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3- to 10-membered heterocyclyl, (3- to 10-membered heterocyclyl)-($C_1$-$C_6$ alkylene)-, $C_6$-$C_{10}$ aryl, ($C_6$-$C_{10}$ aryl)-($C_1$-$C_6$ alkylene)-, 5- to 10-membered heteroaryl, (5- to 10-membered heteroaryl)-($C_1$-$C_6$ alkylene)-, methylenedioxy and ethylenedioxy is optionally and independently substituted with one or more $R^4$ groups; and each $R^a$, $R^b$, $R^c$, $R^d$ and $R^4$ is as defined herein.

In yet another embodiment, each $R^3$ is independently H, D, F, Cl, —CN, —$NO_2$, —$NH_2$, —$NMe_2$, —NHEt, —$NEt_2$, —OH, —OMe, —OEt, —O(n-Pr), —O(i-Pr), —O(t-Bu), -Me, -Et, -(n-Pr), -(i-Pr), -(t-Bu), —$CF_3$, —$CH_2CH_2Cl$, —$OCHF_2$, —$OCF_3$, —$OCH_2CF_3$, —$OCF_2CHF_2$, —$OCHFCF_3$, —$OCF_2CF_3$, —$OCF_2CH_2CH_3$, —$OCF_2CH_2CF_3$, —$OCF_2CH_2CHF_2$, —$OCH_2CHFCH_3$, —$OCH_2CF_2CH_3$, —$OCH_2CF_2CF_3$, —$OCH_2CF_2CHF_2$, —$CONH_2$, —CONHMe, —$CONMe_2$, —C(=O)OMe, —C(=O)OEt, —NHC(=O)H, —NHC(=O)$CH_3$, —NHC(=O)OMe, —NHC(=O)$CH_2$OMe or phenyl.

In another embodiment, each $R^a$ and $R^b$ is independently H, $C_1$-$C_4$ alkyl, $C_3$-$C_4$ alkenyl, $C_3$-$C_4$ alkynyl, $C_1$-$C_4$ haloalkyl, $C_5$-$C_6$ cycloalkyl, ($C_5$-$C_6$ cycloalkyl)-($C_1$-$C_4$ alkylene)-, 5- to 7-membered heterocyclyl, (5- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-, or $R^a$ and $R^b$ together with the nitrogen atom to which they are attached, form a 5- to 7-membered heterocyclic ring; and each $R^c$ and $R^d$ is independently H, $C_1$-$C_4$ alkyl, $C_2$-$C_4$ alkenyl, $C_2$-$C_4$ alkynyl, $C_1$-$C_4$ haloalkyl, $C_5$-$C_6$ cycloalkyl, ($C_5$-$C_6$ cycloalkyl)-($C_1$-$C_4$ alkylene)-, 5- to 7-membered heterocyclyl, (5- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-.

In yet another embodiment, each $R^a$ and $R^b$ is independently H, -Me, -Et, -(n-Pr), -(i-Pr), -(t-Bu), —$CF_3$, —$CH_2CH_2Cl$, cyclopentyl, pyrrolidinyl, piperidinyl, morpholinyl or piperazinyl, or $R^a$ and $R^b$ together with the nitrogen atom to which they are attached, form a 5- to 6-membered heterocyclic ring; and each $R^c$ and $R^d$ is independently H, -Me, -Et, -(n-Pr), -(i-Pr), -(t-Bu), —$CHF_2$, —$CF_3$, —$CH_2CF_3$, –$CF_2CHF_2$, —$CHFCF_3$, —$CF_2CF_3$, —$CF_2CH_2CH_3$, —$CF_2CH_2CF_3$, —$CF_2CH_2CHF_2$, —$CH_2CHFCH_3$, —$CH_2CF_2CH_3$, —$CH_2CF_2CF_3$, —$CH_2CF_2CHF_2$, —$CH_2CH_2Cl$, cyclopentyl, pyrrolidinyl, piperidinyl, morpholinyl or piperazinyl.

In yet another embodiment, provided herein is a compound having one of the following structures or a stereoisomer, a tautomer, an N-oxide, a solvate, a metabolite, a pharmaceutically acceptable salt or a prodrug thereof:

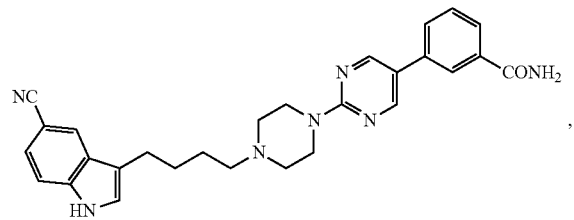

(1)

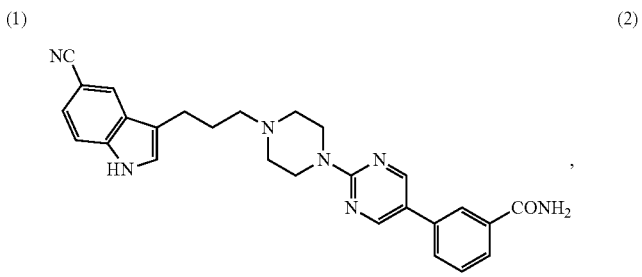

(2)

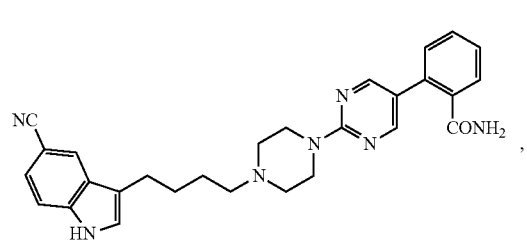

(3)

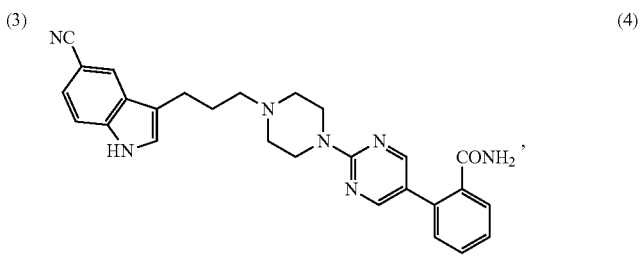

(4)

-continued
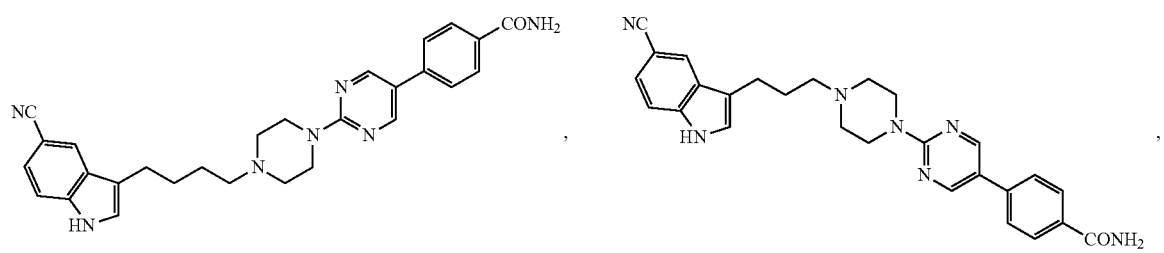
(5) (6)
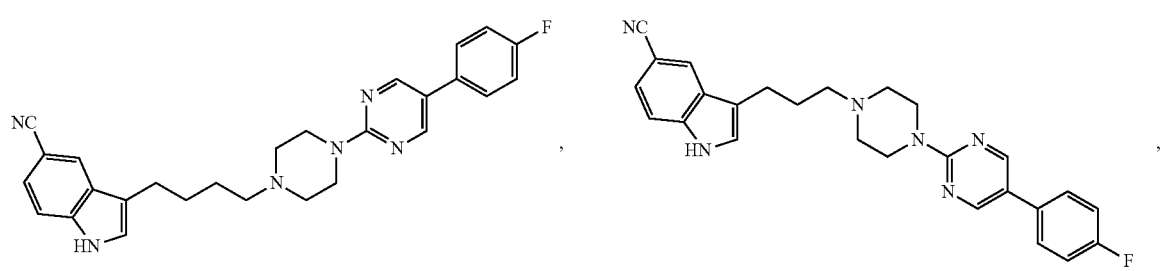
(7) (8)
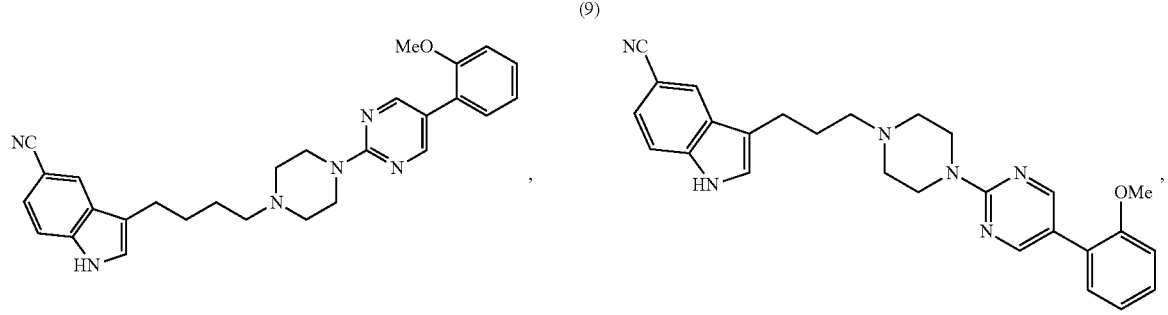
(9) (10)
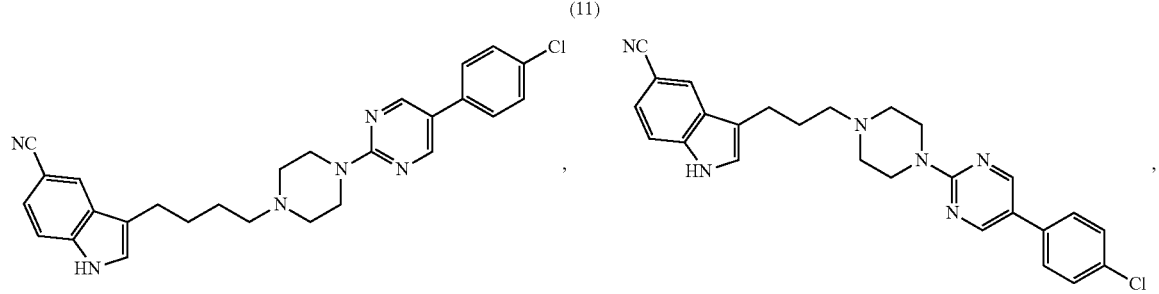
(11) (12)
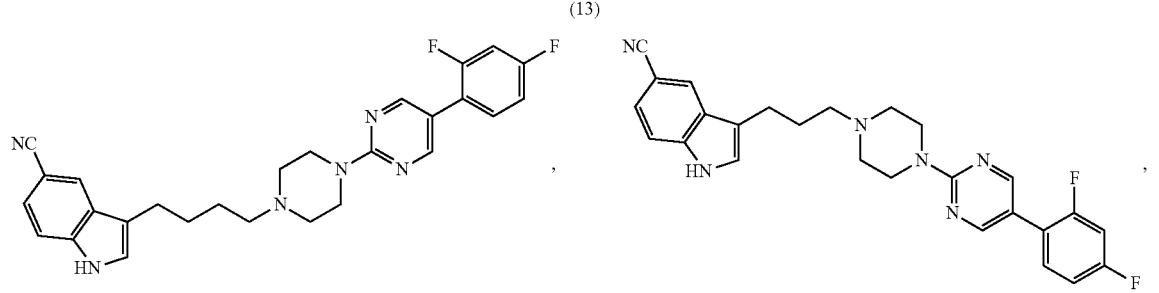
(13) (14)

(15)
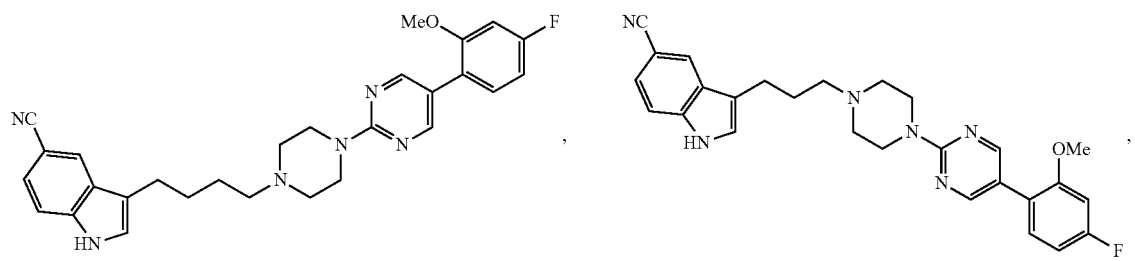
(16)
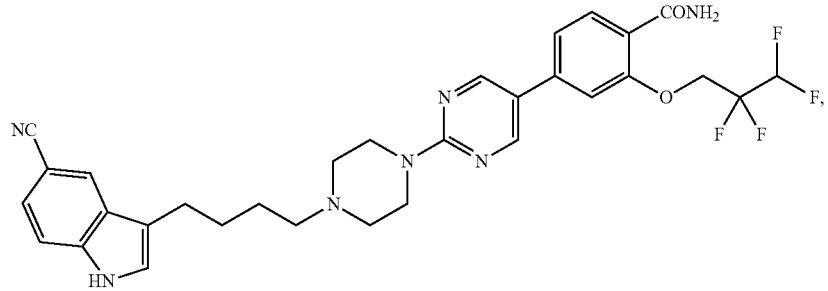
(17)
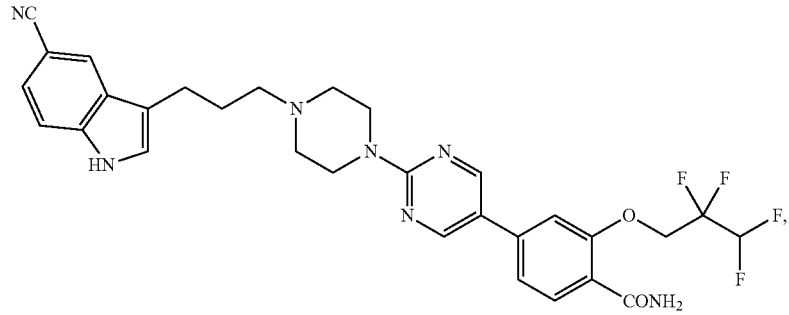
(18)
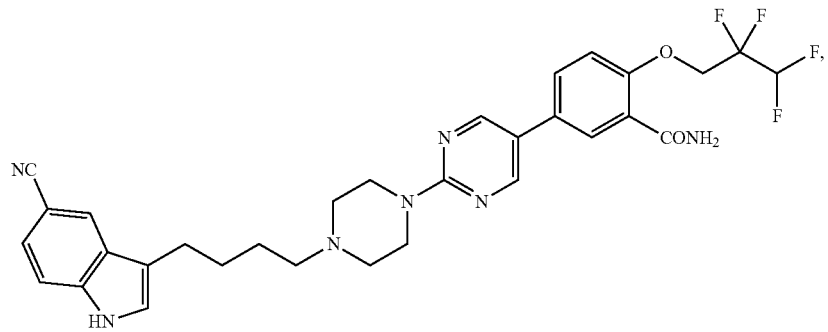
(19)
(20)
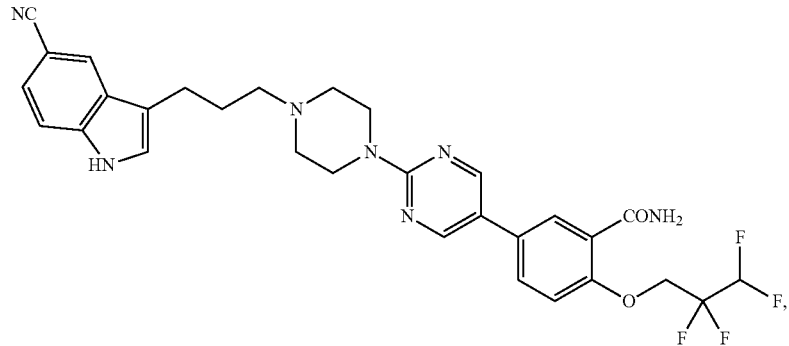

-continued
(21)
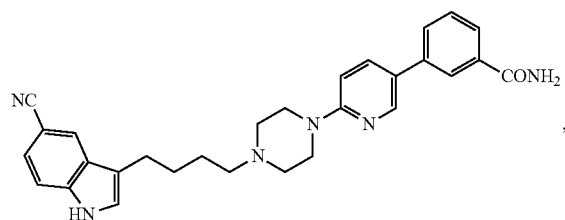
(22)
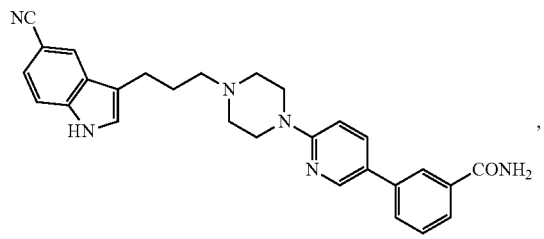
(23)
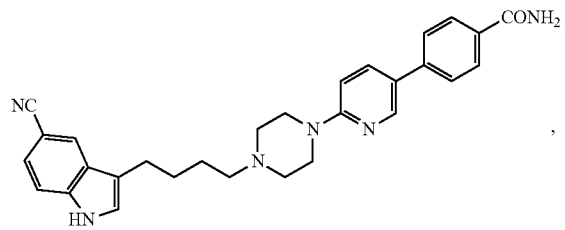
(24)
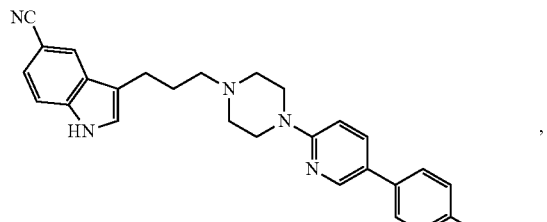
(25)
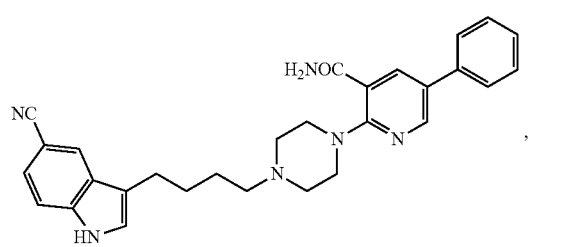
(26)
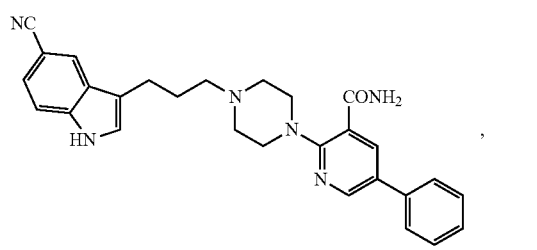
(27)
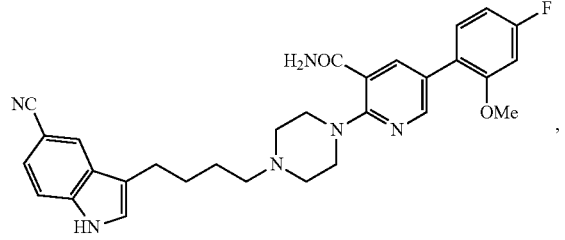
(28)
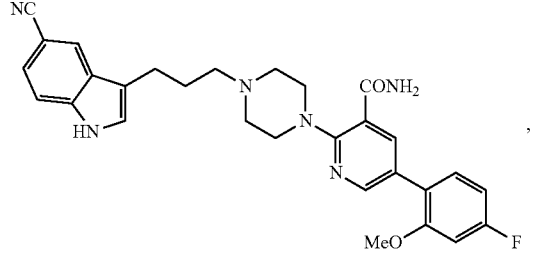
(29)
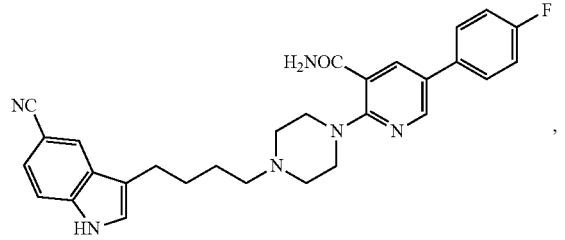
(30)
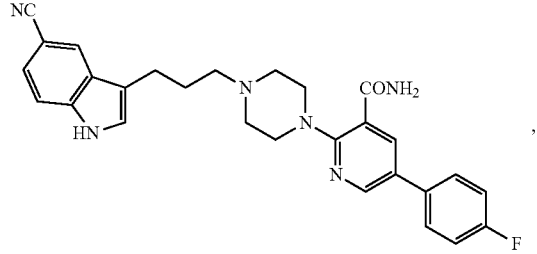
(31)
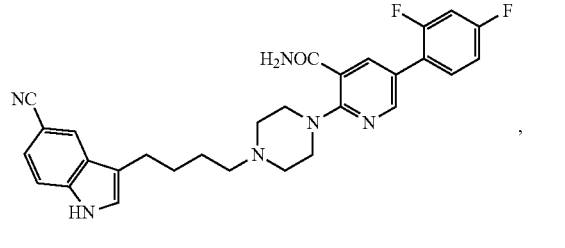
(32)
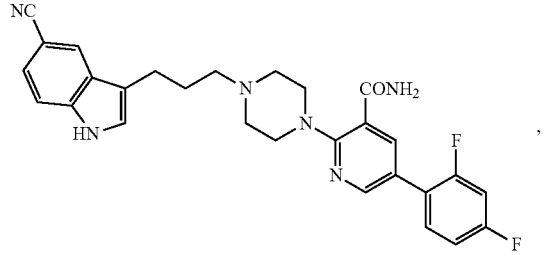

-continued
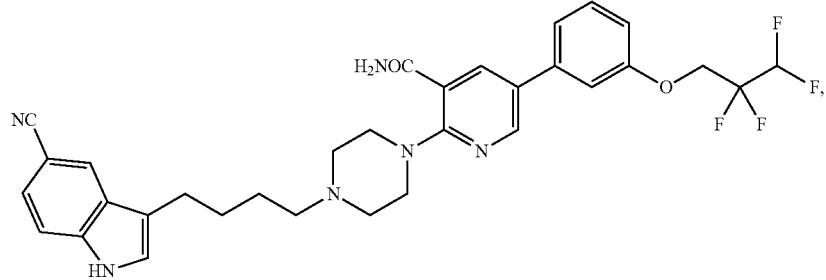
(33)
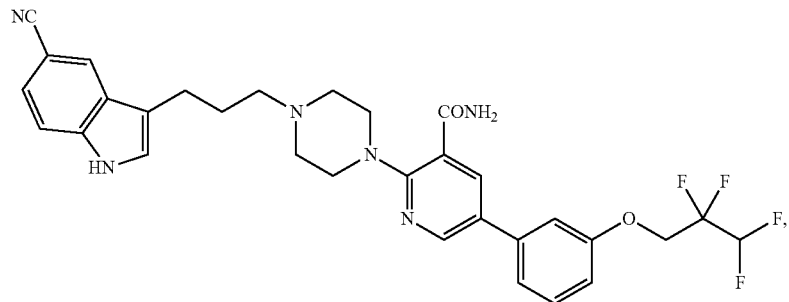
(34)
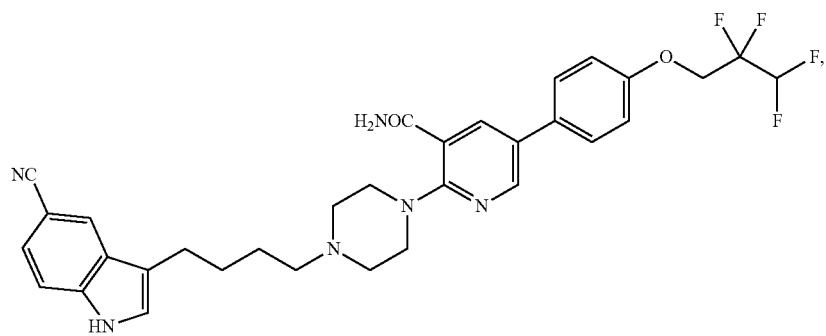
(35)
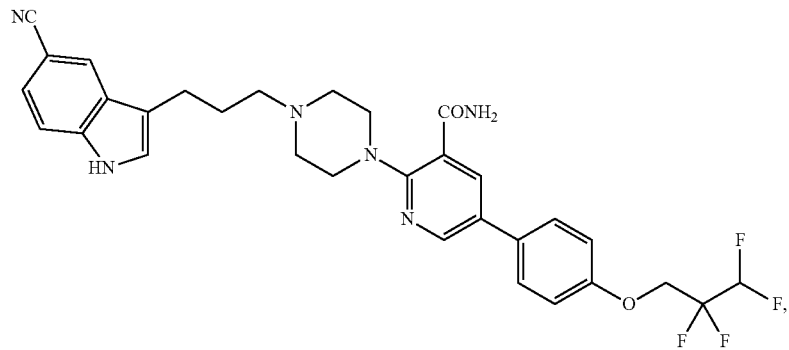
(36)

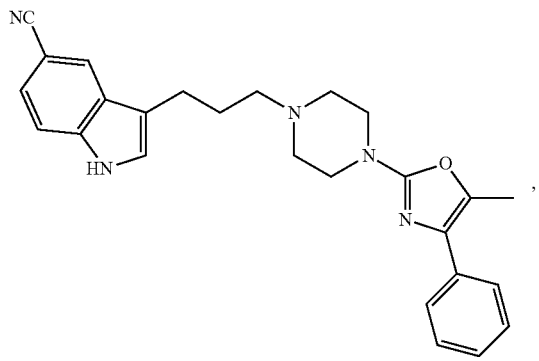

(37)

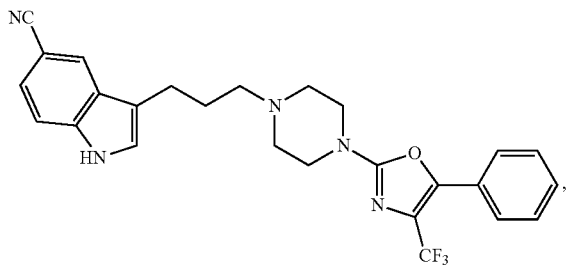

(38)

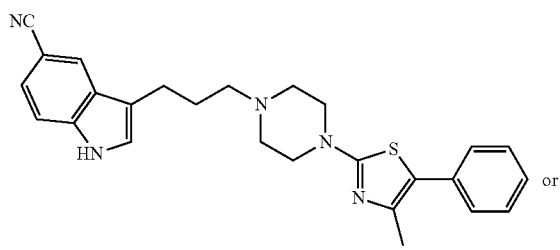

(39) or

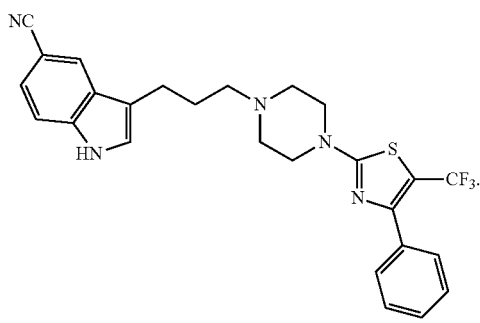

(40)

Unless otherwise stated, all suitable isotope changes, stereoisomers, tautomers, solvates, metabolites, salts and pharmaceutically acceptable prodrugs of the compounds disclosed herein are within the scope of the invention.

The compounds disclosed herein may contain asymmetric or chiral centers, and therefore exist in different stereoisomeric forms. It is intended that all stereoisomeric forms of the compounds shown in Formula (I) to (VI), include, but are not limited to, diastereomers, enantiomers, atropisomer and geometric (or conformational) isomers, as well as mixtures thereof such as racemic mixtures, form parts of the present invention.

In the structure disclosed herein, when the stereochemistry of any particular chiral atom is not specified, all stereoisomers of the structure are contemplated within the scope of the present invention, and contemplated within the scope of the present inventionas as the disclosed compounds disclosed herein. Where stereochemistry is specified by a solid wedge or dashed line representing a particular configuration, then that stereoisomer is so specified and defined.

The compounds shown in Formula (I) to (VI) may exist in different tautomeric forms, and all of these tautomers are contemplated within the scope of the present invention.

N-oxides of the compounds disclosed herein are also within the scope of the invention and may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

The compounds of Formula (I) to (VI) can exist in the form of salts. In some embodiments, the salt is a pharmaceutically acceptable salt. The term "pharmaceutically acceptable" refers to that the substance or composition must be compatible chemically and/or toxicologically, with the other ingredients comprising a formulation, and/or the mammal being treated therewith. In some another embodiments, the salts are not necessarily a pharmaceutical acceptable salt, and which may be useful as intermediates for preparing and/or purifying compounds of Formula (I) to (VI) and/or for separating enantiomers of compounds of Formula (I) to (VI).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Furthermore, the compounds of the present invention, including their salts, can also be obtained in the form of their hydrates, or include other solvents (such as ethanol, DMSO, and the like), used for their crystallization. The compounds of the present invention may inherently or by design form solvates with pharmaceutically acceptable solvents (including water); therefore, it is intended that the compounds of the present invention embrace both solvated and unsolvated forms.

Any formula given herein is also intended to represent isotopically unenriched forms as well as isotopically enriched forms of the compounds. Isotopically enriched compounds have the structure represented by the general formula of the present invention, but for the fact that one or more atoms are replaced by an atom having an atomic mass or mass number. Examples of isotopes that can be incorporated into compounds of the invention include isotopes of hydrogen, carbon, nitrogen, oxygen, phosphorous, sulfur, fluorine and chlorine, such as $^2$H, $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl and $^{125}$I.

In another aspect, the compounds of the invention include isotopically enriched compounds as defined herein, for example, wherein radioisotopes exist, such as $^3$H, $^{14}$C and $^{18}$F, or wherein non-radioactive isotopes exist, such as $^2$H and $^{13}$C. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. $^{18}$F-enriched compounds are particularly desirable for PET or SPECT studies. Isotopically-enriched compounds of Formula (I) to (VI) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability. For example, increased in vivo half-life or reduced dosage requirements or an improvement in therapeutic index. It is understood that deuterium in this context is regarded as a substituent of compounds of Formula (I) to (VI). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

In another aspect, the present invention relates to intermediates useful in the preparation of the compounds represented by Formula (I) to (VI).

In another aspect, the present invention relates to methods for preparing, separating, and purifying the compounds represented by Formula (I) to (VI).

In another aspect, provided herein is a pharmaceutical composition comprising the compounds disclosed herein. In some embodiments, the pharmaceutical compositions disclosed herein further comprise pharmaceutically acceptable carriers, excipients, adjuvants, solvents or any combinations thereof. In some another embodiments, the pharmaceutical compositions may be liquid, solid, semi-solid, gel or spray.

Pharmaceutical Composition of the Compound of the Invention and Preparations and Administration Provided herein is a pharmaceutical composition comprising a compound represented by Formula (I) to (VI) or an individual stereoisomer thereof, a racemic or non-racemic mixture of isomers, or a pharmaceutically acceptable salt or a solvate thereof. In one embodiment of the present invention, the pharmaceutical composition further comprises at least one pharmaceutically acceptable carrier, adjuvant, or excipient, and optionally other therapeutic and/or prophylactic ingredients.

Suitable carriers, adjuvants and excipients are well known to those skilled in the art and described in detail in such as Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C., Handbook of Pharmaceutical Excipients (2005) Pharmaceutical Press, Chicago.

It will also be appreciated that certain compounds of the present invention can exist in free form for treatment, or where appropriate, as a pharmaceutically acceptable derivative or a prodrug thereof. According to the present invention, Some non-limiting examples of the pharmaceutically acceptable derivative include, a pharmaceutically acceptable prodrug, salts, esters, salts of such esters, or any other adduct or derivative which upon administration to a patient in need thereof is capable of providing, directly or indirectly, a compound as otherwise described herein, or a metabolite or residue thereof.

The pharmaceutical compositions of the invention may be prepared and packaged in bulk form, wherein a safe and effective amount of a compound disclosed herein can be extracted and then given to the patient, such as with powders or syrups. Alternatively, the pharmaceutical compositions of the invention may be prepared and packaged in unit dosage form wherein each physically discrete unit contains a safe and effective amount of a compound disclosed herein. When prepared in unit dosage form, the pharmaceutical compositions of the invention commonly contain from about 0.5 mg to 1 g, or 1 mg to 700 mg, or 5 mg to 100 mg, of the compound of the invention.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition, the pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared at for example environment temperature and under barometric pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein will be formulated for oral administration. In another embodiment, the compounds disclosed herein will be formulated for inhaled administration. In a further embodiment, the compounds disclosed herein will be formulated for intranasal administration. In another embodiment, the compounds disclosed herein will be formulated for transdermal administration. In a further embodiment, the compounds disclosed herein will be formulated for topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In another aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the polymorph or salt of the invention may be employed with either a paraffinic or a water-miscible ointment base. Alternatively, the polymorph or salt of the invention may be formulated in a cream with an oil-in-water cream base or a water-in-oil base.

In one embodiment, the therapeutic methods disclosed herein comprise administrating to a patient in need of the treatment a safe and effective amount of the compound of the invention or the pharmaceutical composition containing the compound of the invention. Each example disclosed herein comprises treating the above disorders or diseases by administrating to a patient in need of the treatment a safe and effective amount of the compound of the invention or the pharmaceutical composition containing the compound of the invention.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In one embodiment, the compound of the invention or the pharmaceutical composition thereof may be administered by inhalation. In a further embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally or parenterally, advantageously intravenously, e.g., as a suspension or in aqueous solution.

In one embodiment, a therapeutically effective dosage of the compound disclosed herein from about 0.1 mg to about 2,000 mg per day. The pharmaceutical compositions should provide a dosage of from about 0.1 mg to about 2000 mg of the compound. In a special embodiment, pharmaceutical dosage unit forms are prepared to provide from about 1 mg to about 2,000 mg, about 10 mg to about 1,000 mg, about 20 mg to about 500 mg, or about 25 mg to about 250 mg of the active ingredient or a combination of essential ingredients per dosage unit form. In a special embodiment, pharmaceutical dosage unit forms are prepared to provide about 10 mg, 20 mg, 25 mg, 50 mg, 100 mg, 250 mg, 500 mg, 1000 mg or 2000 mg of the active ingredient.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Use of the Compounds and Pharmaceutical Compositions

The compounds and pharmaceutical compositions disclosed herein can be used in the manufacture of a medicament for preventing, treating or lessening a central nervous system dysfunction in mammals including humans, as well as for inhibiting 5-hydroxytryptamine reuptake and/or acting as 5-$HT_{1A}$ receptor agonists.

In particular, the amount of the compound contained in the composition disclosed herein can effectively, detectably, and selectively inhibit 5-hydroxytryptamine reuptake and has agonistic effects on 5-$HT_{1A}$ receptors, and the compounds disclosed herein can be used as the medicaments for treating a central nervous system (CNS) dysfunction, such as depression, anxiety disorder and bipolar disorder.

Compounds disclosed herein would be useful for, but are not limited to, preventing or treating or lessening a central nervous system dysfunction by administering to the patient a compound or a composition disclosed herein in an effective amount. The central nervous system dysfunctional diseases responded to the regulatory of 5-hydroxytryptamine, further include but are not limited to depression, anxiety, mania, schizophrenia, a sleep disorder, a bipolar disorder, an obsessive-compulsive disorder, a panic disorder, a post-traumatic stress disorder, a movement disorder, a sexual dysfunction, a musculoskeletal pain disorder, a cognitive disorder, a memory disorder, Parkinson's disease, Huntington's disease, a phobia, substance abuse or addiction, drug addiction or withdrawal symptoms and premenstrual tension syndrome.

Besides being useful for human treatment, the compounds of the present invention and the compositions thereof are also useful for veterinary treatment of animals such as companion animals, exotic animals and mammals of farm animals. In other embodiments, the animals disclosed herein include horses, dogs, and cats. As used herein, the compounds disclosed herein include the pharmaceutically acceptable derivatives thereof.

General Synthetic Procedures

The invention is described by the following examples. But it is to be understood that the invention is not limited to those embodiments thereof, the examples are meant only to suggest a method of practicing the present invention.

Generally, the compounds disclosed herein may be prepared by methods described herein, wherein the substituents are as defined for Formula (I) to (VI), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fuchen Reagent Chemical Factory, Wuhan XinHuaYuan Technology Development Co., Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Glassware was oven dried and/or heat dried.

Column chromatography was conducted using a silica gel column. Silica gel (300-400 mesh) was purchased from Qingdao Ocean Chemical Factory.

$^1$H NMR spectra were recorded using a Bruker 400 MHz or 600 MHz spectrometer. $^1$H NMR spectra were obtained by using $CDCl_3$, DMSO-$d_6$, $CD_3OD$ or acetone-$d_6$ solutions (reported in ppm), with TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants (J), when given, were reported in Hertz (Hz).

Low-resolution mass spectral (MS) data were determined on an Agilent 6120 Quadrupole HPLC-MS spectrometer equipped with an Agilent Zorbax SB-C18 (2.1×30 mm, 3.5 µm). The flow rate was 0.6 mL/min. The mobile phases consisted of a combination of A (0.1% formic acid in CH₃CN) and B (0.1% formic acid in H₂O) in gradient mode (5% to 95%), and an ESI source was used, the peak of HPLC was recorded with UV-Vis detection at 210/254 nm.

Purification of compound was detected on Agilent 1260 pre-HPLC or Calesep pump 250 pre-HPLC with UV at 210 nm/254 nm (NOVASEP, 50/80 mm DAC).

The following abbreviations are used throughout the specification:
$CH_2Cl_2$, DCM dichloromethane
$CDCl_3$ chloroform-d
DIEA, DIPEA diisopropylethylamine
DMF N,N-dimethylformamide
DMAP 4-dimethylaminopyridine
DMSO dimethylsulfoxide
EtOAc, EA ethyl acetate
$Et_3N$, TEA triethylamine
EDTA ethylenediaminetetraacetic acid
g gram
h hour, hours
$K_2CO_3$ potassium carbonate
KI potassium iodide
KCl potassium chloride
MeOH, $CH_3OH$ methanol
$MgSO_4$ magnesium sulfate
mL, ml milliliter
min minute, minutes
$N_2$ nitrogen
RT, rt, r.t. room temperature
$NaBH_4$ sodium borohydride
$NaHCO_3$ sodium bicarbonate
$NaH_2PO_4$ sodium dihydrogenphosphate
NaCl sodium chloride
$Na_2SO_4$ sodium sulfate
PE petroleum ether (60-90° C.)
THF tetrahydrofuran
Pd(dppf)Cl₂, [1,1'-bis(diphenylphosphino)ferrocene]dichloropalladium(II)
BSA bovine serum protein
Tris-HCl tris (hydroxymethyl) aminomethane—Hydrochloric acid The following Schemes describe the procedures for preparation of compounds of the present invention. Unless otherwise stated, each W, X, $R^1$, $R_2$, $R^3$, $R^x$, m, n, k, r and p is as defined herein.

Scheme 1:

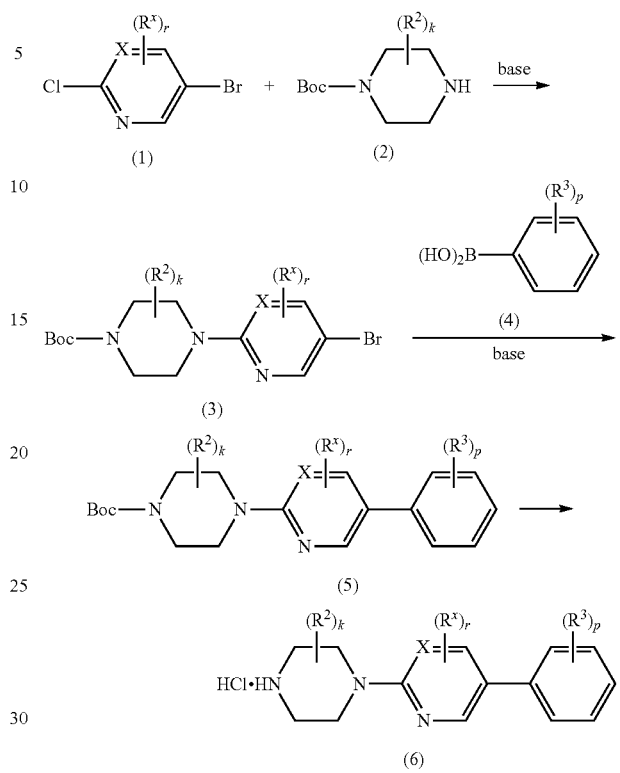

Compound (6) can be prepared by the general synthetic procedure illustrated in Scheme 1, and the specific steps are described in the corresponding examples: firstly, compound (1) can react with compound (2) by substitution reaction in the presence of a base in a suitable solvent (such as acetonitrile or 1,4-dioxane) to afford compound (3); compound (3) can then react with substituted phenylboronic acid (4) to afford compound (5) by suzuki coupled reaction; finally, salt forming reaction of compound (5) in a solution of hydrogen chloride in ethyl acetate to afford compound (6).

Scheme 2:

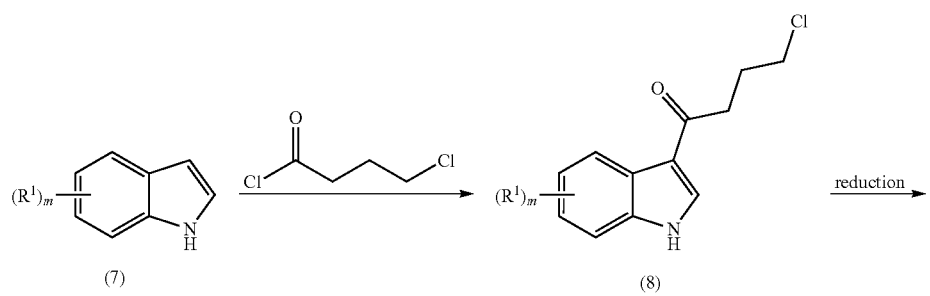

-continued

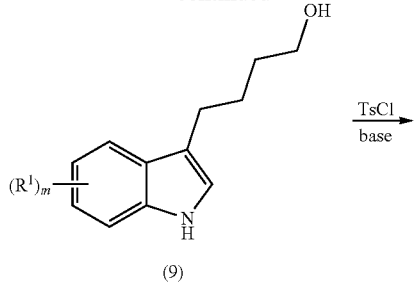

(9)

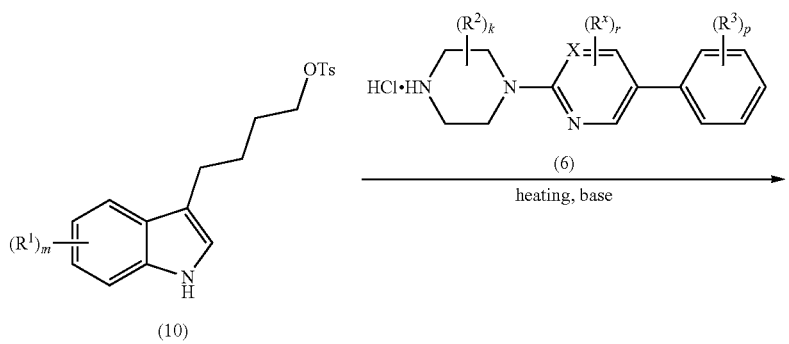

(10)  (6)

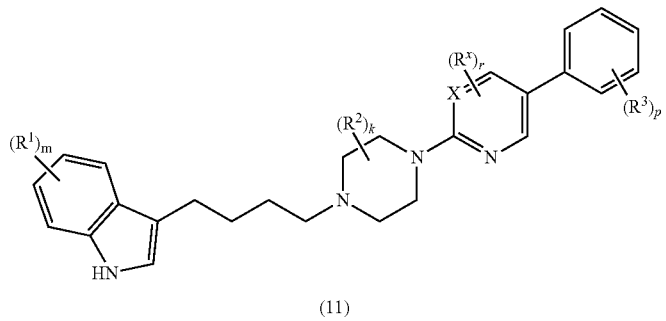

(11)

Compounds of the present invention can be prepared by the general synthetic procedure illustrated in Scheme 2, and the specific steps are described in the corresponding examples. Firstly, compound (7) can react with chlorobutyryl chloride to afford compound (8) by Friedel-Crafts acylation; compound (8) can react with a reducing agent such as sodium borohydride or lithium aluminium hydride, in a suitable solvent (such as tert-butanol or i-propanol) to afford compound (9); the hydroxy group of compound (9) can be converted into toluenesulfonic acid group to afford compound (10), and compound (10) can react with compound (6) in the presence of an inorganic base (such as potassium carbonate or sodium carbonate) or an organic base (such as triethylamine), in a suitable solvent (such as acetonitrile, tetrahydrofuran, ethanol or DMF) to afford object compound (11) by nucleophilic substitution reaction.

Scheme 3:

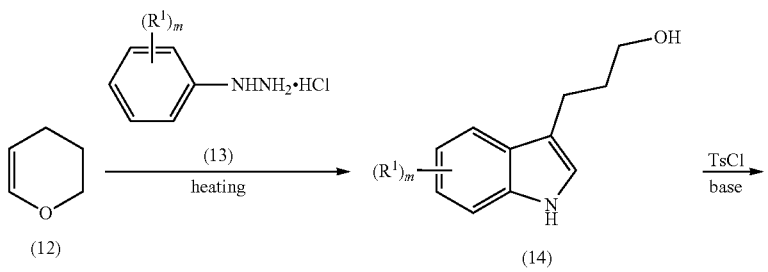

(12) (13) (14)

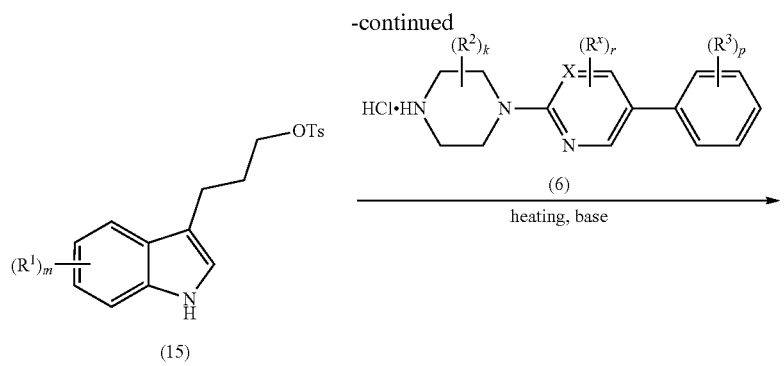

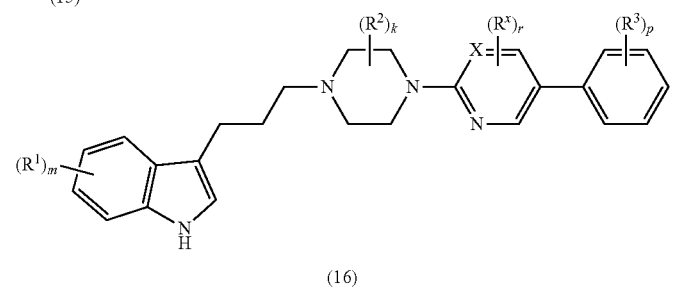

Compounds of the present invention can be prepared by the general synthetic procedure illustrated in Scheme 3, and the specific steps are described in the corresponding examples. Firstly, tetrahydropyran (12) can react with phenylhydrazine compound (13) by Fischer indole n-cyclohexylmaleimide reaction to afford compound (14) at a suitable temperature such as 40~120° C.; the hydroxy group of compound (14) can be converted into toluenesulfonic acid group to afford compound (15) and then compound (15) can react with compound (6) in the presence of an inorganic base (such as potassium carbonate or sodium carbonate) or an organic base (such as triethylamine), in a suitable solvent (such as acetonitrile, tetrahydrofuran, ethanol or DMF) to afford object compound (16) by nucleophilic substitution reaction.

Scheme 4:

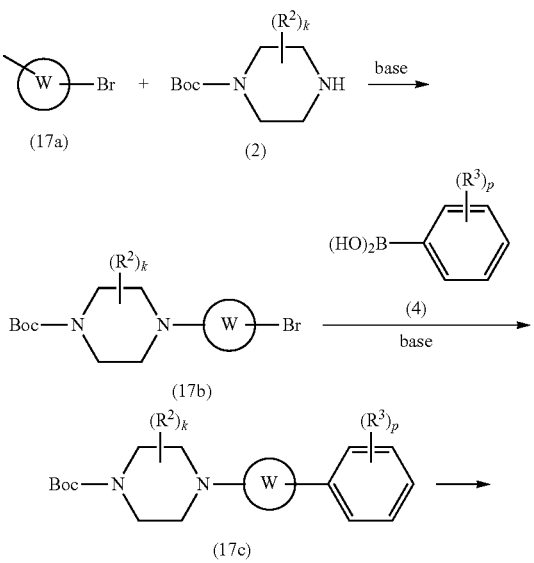

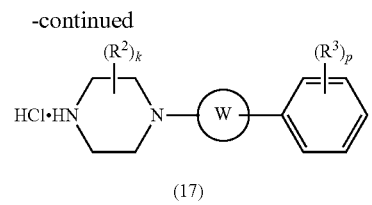

Compound (17) can be prepared by the general synthetic procedure illustrated in Scheme 4, and the specific steps are described in the corresponding examples. Firstly, compound (17a) can react with compound (2) by substitution reaction in the presence of a base in a suitable solvent (such as acetonitrile or 1,4-dioxane) to afford compound (17b); then compounds (17b) can react with substituted phenylboronic acid (4) to afford compound (17c) by suzuki coupled reaction; finally, salt forming reaction of compound (17c) in a solution of hydrogen chloride in ethyl acetate to afford compound (17).

Scheme 5:

-continued

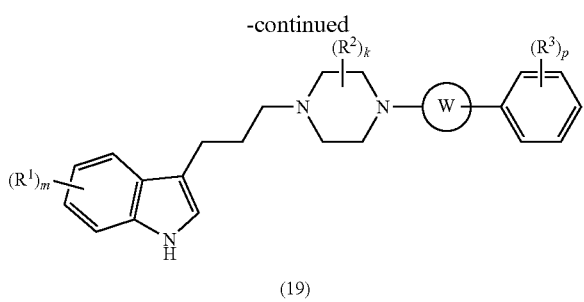

(19)

Compound (19) can be prepared by the general synthetic procedure illustrated in Scheme 5, and the specific steps are described in the corresponding examples. Compound (18) can react with compound (17) in the presence of an inorganic base (such as potassium carbonate or sodium carbonate) or an organic base (such as triethylamine), in a suitable solvent (such as acetonitrile, tetrahydrofuran, ethanol or DMF) to afford object compound (19) by nucleophilic substitution reaction.

Compounds and pharmaceutical compositions provided herein and the application thereof are further illustrated in combination with the following examples.

EXAMPLE

Example 1

3-(2-(4-(4-(5-cyano-1H-indol-3-yl)butyl)piperazin-1-yl)pyrimidin-5-yl)benzamide

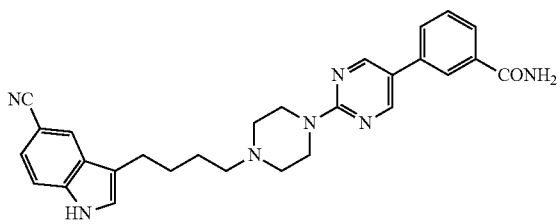 [SMILES: N#Cc1ccc2[nH]cc(CCCCN3CCN(c4ncc(-c5cccc(C(N)=O)c5)cn4)CC3)c2c1]

Step 1) Synthesis of 3-(4-chlorobutanoyl)-1H-indole-5-carbonitrile

To a solution of aluminium chloride (9.00 g, 68.00 mmol) in dichloromethane (90 mL) was added 4-chlorobutyryl chloride (9.60 g, 68.00 mmol) dropwise at 0° C., the reaction mixture was stirred for 30 minutes, and then a soluton of 5-cyanoindole (8.10 g, 57.00 mmol) in dichloromethane (800 mL) was added dropwise. The reaction was warmed to room temperature, and after stirring 2 hours, the mixture was poured into a mixture of ice (50 g) and concentrated hydrochloric acid (50 mL), and then the stir was continued at room temperature for 20 hours. The resulting mixture was filtered by suction, and the filter cake was washed sequentially with water (10 mL) and ethyl acetate (10 mL), then dried to give the title product as a yellow solid (8.90 g, 63.1%).

LC-MS (ESI, pos. ion) m/z: 247.1 [M+H]$^+$.

Step 2) Synthesis of 3-(4-hydroxybutyl)-1H-indole-5-carbonitrile 3-(4-Chlorobutanoyl)-1H-indole-5-carbonitrile (0.49 g, 2.00 mmol) was dissolved in i-propanol (20 mL), the reaction mixture was cooled to 0° C., then sodium borohydride (0.23 g, 6.00 mmol) was added in portions. The reaction mixture was heated to 80° C., after stirring for 6 hours, the reaction mixture was cooled to 0° C. and quenched with saturated sodium carbonate solution (1 mL). The mixture was filtered by suction, and the filtrate was concentrated in vacuo and the residue was purified by silica gel chromatography (PE/EtOAc (v/v)=2/1) to give the title compound as a white solid (343 mg, 80.0%).

LC-MS (ESI, pos. ion) m/z: 215.2 [M+H]$^+$.

Step 3) Synthesis of 4-(5-cyano-1H-indol-3-yl)butyl 4-methylbenzenesulfonate 3-(4-Hydroxybutyl)-1H-indole-5-carbonitril (0.41 g, 1.90 mmol) was dissolved in dichloromethane (20 mL), then triethylamine (0.3 mL, 2.28 mmol) and p-toluensulfonyl chloride (0.43 g, 2.28 mmol) were added in turn. The mixture was stirred at room temperature for 4 hours, then quenched with water (100 mL). After separation, the organic phase was dried over anhydrous sodium sulfate, filtered, and concentrated in vacuo, the residue was purified by silica gel chromatography (PE/EtOAc (v/v)=4/1) to give the title compound as a white solid (0.56 g, 80.0%).

LC-MS (ESI, pos. ion) m/z: 369.2 [M+H]$^+$.

Step 4) Synthesis of tert-butyl 4-(5-bromopyrimidin-2-yl)piperazine-1-carboxylate To 1,4-dioxane (30 mL) were added tert-butyl piperazine-1-carboxylate (2.89 g, 15.51 mmol), 5-bromo-2-chloropyrimidine (2.00 g, 10.34 mmol) and potassium carbonate (2.86 g, 20.68 mmol) sequentially. The mixture was heated to 110° C., after stirring for 12 hours, the reaction mixture was cooled to room temperature, filtered and concentrated in vacuo. The residue was purified by silica gel chromatography (PE/EtOAc (v/v)=20/1) to give the title compound as a pale yellow solid (3.15 g, 88.7%).

MS (ESI, pos. ion) m/z: 343.1 [M+H]$^+$; and $^1$H NMR (400 MHz, CDCl$_3$): δ (ppm) 8.29 (s, 2H), 3.83-3.66 (m, 4H), 3.56-3.41 (m, 4H), 1.48 (s, 9H).

Step 5) Synthesis of tert-butyl 4-(5-(3-carbamoylphenyl)pyrimidin-2-yl)piperazine-1-carboxylate To a mixed solvent of 1,4-dioxane (15 mL) and water (1 mL) were added tert-butyl 4-(5-bromopyrimidin-2-yl)piperazine-1-carboxylate (840 mg, 2.45 mmol), (3-carbamoylphenyl)boric acid (403 mg, 2.45 mmol), Pd(dppf)Cl$_2$ (180 mg, 0.24 mmol) and cesium carbonate (2.39 g, 7.34 mmol) sequentially. The mixture was heated to 110° C., after stirring for 24 hours, the reaction was cooled to room temperature, then concentrated in vacuo to remove 1,4-dioxane. To the residue was added water (10 mL), and the resulting mixture was extracted with dichloromethane (20 mL×3). The combined organic phase was dried over anhydrous sodium sulfate, filtered and concentrated in vacuo, the residue was purified by silica gel chromatography (PE/EtOAc (v/v)=1/2) to give the title compound as a white solid (340 mg, 36.2%).

MS (ESI, pos. ion) m/z: 384.3 [M+H]$^+$; and $^1$H NMR (600 MHz, DMSO-d$_6$): δ (ppm) 8.79 (s, 2H), 8.12 (d, J=1.6 Hz, 1H), 8.05 (s, 1H), 7.83 (d, J=7.8 Hz, 1H), 7.80 (d, J=7.8 Hz, 1H), 7.53 (t, J=7.8 Hz, 1H), 7.43 (s, 1H), 3.84-3.77 (m, 4H), 3.49-3.39 (m, 4H), 1.44 (s, 9H).

Step 6) Synthesis of 3-(2-(piperazin-1-yl)pyrimidin-5-yl)benzamide hydrochloride To tert-butyl 4-(5-(3-carbamoylphenyl)pyrimidin-2-yl)piperazine-1-carboxylate (650 mg, 1.70 mmol) was added a solution of hydrogen chloride in ethyl acetate (15 mL, 4 N), after reacting at room temperature for 3 hours, then the reaction mixture was concentrated in vacuo to afford the title compound as a pale yellow solid (520 mg, 95.9%).

MS (ESI, pos. ion) m/z: 320.1 [M+H]$^+$; and $^1$H NMR (600 MHz, DMSO-d$_6$): δ (ppm) 8.91 (s, 2H), 8.04 (s, 2H), 7.36 (s, 1H), 7.04 (d, J=7.2 Hz, 1H), 7.00 (d, J=7.0 Hz, 1H), 6.82-6.66 (m, 1H), 3.30-3.20 (m, 4H), 2.40-2.30 (m, 4H), 1.49 (s, 1H).

Step 7) Synthesis of 3-(2-(4-(4-(5-cyano-1H-indol-3-yl)butyl)piperazin-1-yl)pyrimidin-5-yl) benzamide To acetonitrile (15 mL) were added 4-(5-cyano-1H-indol-3-yl)butyl 4-methylbenzenesulfonate (346 mg, 0.94 mmol), 3-(2-(piperazin-1-yl)pyrimidin-5-yl)benzamide hydrochloride (250 mg, 0.78 mmol), sodium carbonate (249 mg, 2.35 mmol) and potassium iodide (13 mg, 0.08 mmol) sequentially, the mixture was warmed to 100° C. under N$_2$, after stirring for 24 hours, the reaction mixture was cooled to room temperature. To the resulting mixture was added water (20 mL), and the mixture was extracted with dichloromethane (20 mL×3). The combined organic phase was dried over anhydrous sodium sulfate, filtered, and concentrated in vacuo, the residue was purified by silica gel chromatography (DCM/MeOH (v/v)=50/1) to give the title compound as a pale yellow solid (235 mg, 62.7%).

MS (ESI, pos. ion) m/z: 480.2 [M+H]$^+$;

$^1$H NMR (400 MHz, DMSO-d$_6$): δ (ppm) 11.46 (s, 1H), 8.86 (s, 2H), 8.22 (s, 1H), 8.17 (s, 1H), 8.15 (s, 1H), 7.93 (d, J=7.7 Hz, 1H), 7.89 (d, J=7.9 Hz, 1H), 7.67-7.57 (m, 2H), 7.56-7.47 (m, 2H), 7.43 (d, J=1.8 Hz, 1H), 3.90 (brs, 4H), 2.85 (t, J=7.4 Hz, 2H), 2.65-2.58 (m, 2H), 2.56 (brs, 4H), 1.83-1.76 (m, 2H), 1.69-1.64 (m, 2H); and $^{13}$C NMR (100 MHz, DMSO-d$_6$): δ (ppm) 168.2, 161.1, 156.3, 138.5, 135.5, 135.4, 129.5, 128.5, 127.6, 126.7, 125.3, 124.8, 124.6, 124.0, 121.9, 121.4, 116.5, 113.0, 100.6, 58.0, 55.3, 53.0, 43.9, 28.1, 24.5.

Example 2

3-(2-(4-(3-(5-cyano-1H-indol-3-yl)propyl)piperazin-1-yl)pyrimidin-5-yl) benzamide

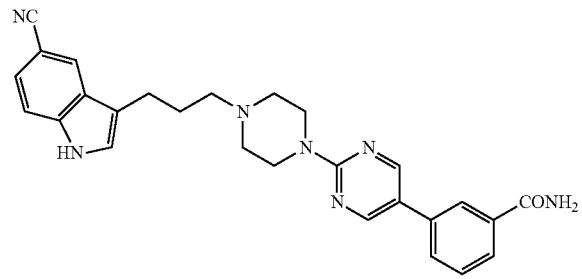 [SMILES: N#Cc1ccc2[nH]cc(CCCN3CCN(c4ncc(-c5cccc(C(N)=O)c5)cn4)CC3)c2c1]

Step 1) Synthesis of 3-(3-hydroxypropyl)-1H-indole-5-carbonitrile

4-Cyanophenylhydrazine hydrochloride (3.53 g, 20.8 mmol) was dissolved in a mixed solvent of dilute sulphuric acid (4%, 50 mL) and N,N-dimethylacetamide (10 mL). To the reaction was added 3,4-dihydro-2H-pyrane (1.9 mL, 20.8 mmol) dropwise. The mixture was heated to 100° C., after stirring for 20 hours, the reaction was cooled to room temperature, and extracted with ethyl acetate (50 mL×3). The combined organic phase was washed with water (50 mL×3), then dried over ahydrous sodium sulfate, filtered, and concentrated in vacuo, the residue was purified by silica gel chromatography (PE/EtOAc (v/v)=2/1) to give the title compound as a white solid (1.46 g, 35.0%).

LC-MS (ESI, pos. ion) m/z: 201.1 [M+H]$^+$.

Step 2) Synthesis of 3-(5-cyano-1H-indol-3-yl)propyl 4-methylbenzenesulfonate 3-(3-Hydroxypropyl)-1H-indole-5-carbonitril (1.00 g, 5.00 mmol) was dissolved in dichloromethane (20 mL), then triethylamine (0.8 mL, 6.00 mmol) and p-toluensulfonyl chloride (1.14 g, 6.00 mmol) were added to the mixture sequentially. The mixture was stirred at room temperature for 4 hours, then quenched with water (100 mL). After separation, the combined organic phases were dried over anhydrous sodium sulfate, filtered, and concentrated in vacuo, the residue was purified by silica gel chromatography (PE/EtOAc (v/v)=4/1) to give the title compound as a white solid (1.33 g, 75.0%).

LC-MS (ESI, pos. ion) m/z: 355.1 [M+H]$^+$.

Step 3) Synthesis of 3-(2-(4-(3-(5-cyano-1H-indol-3-yl)propyl)piperazin-1-yl)pyrimidin-5-yl) benzamide The title compound was prepared using 3-(5-cyano-1H-indol-3-yl)propyl 4-methylbenzenesulfonate (532 mg, 1.50 mmol), 3-(2-(piperazin-1-yl)pyrimidin-5-yl)benzamide hydrochloride (400 mg, 1.25 mmol), sodium carbonate (398 mg, 3.75 mmol) and potassium iodide (21 mg, 0.13 mmol) in acetonitrile (15 mL) according to the process described in Step 7 of Example 1, and the crude product was purified by silica gel chromatography (DCM/MeOH (v/v)=50/1) to give the title compound as a pale yellow solid (384 mg, 66.1%).

MS (ESI, pos. ion) m/z: 466.2 [M+H]$^+$;

$^1$H NMR (600 MHz, DMSO-d$_6$): δ (ppm) 11.37 (s, 1H), 8.75 (s, 2H), 8.12 (s, 1H), 8.09 (s, 1H), 8.05 (s, 1H), 7.83 (d, J=7.7 Hz, 1H), 7.78 (d, J=7.9 Hz, 1H), 7.53-7.49 (m, 2H), 7.43 (s, 1H), 7.39 (dd, J=8.4, 1.4 Hz, 1H), 7.34 (d, J=1.8 Hz, 1H), 3.80 (brs, 4H), 2.75 (t, J=7.4 Hz, 2H), 2.43 (t, J=4.8 Hz, 4H), 2.36 (t, J=7.1 Hz, 2H), 1.86-1.81 (m, 2H); and $^{13}$C NMR (100 MHz, DMSO-d$_6$): δ (ppm) 168.2, 161.1, 156.3, 138.4, 135.5, 135.4, 129.5, 128.5, 127.7, 126.7, 125.4, 124.8, 124.7, 124.0, 121.9, 121.4, 116.3, 113.0, 100.7, 57.8, 53.1, 44.0, 27.6, 22.4.

Example 3

2-(2-(4-(4-(5-cyano-1H-indol-3-yl)butyl)piperazin-1-yl)pyrimidin-5-yl)benzamide

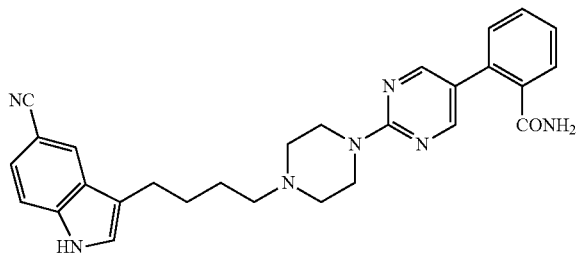 [SMILES: N#Cc1ccc2[nH]cc(CCCCN3CCN(c4ncc(-c5ccccc5C(N)=O)cn4)CC3)c2c1]

Step 1) Synthesis of tert-butyl 4-(5-(2-carbamoyl-phenyl)pyrimidin-2-yl)piperazine-1-carboxylate The title compound was prepared using tert-butyl 4-(5-bromopyrimidin-2-yl)piperazine-1-carboxylate (3.77 g, 11.00 mmol), (2-carbamoylphenyl) boric acid (1.81 g, 11.00 mmol), Pd(dppf)Cl$_2$ (732 mg, 0.98 mmol) and caesium carbonate (10.75 g, 33.00 mmol) in a mixture of 1,4-dioxane (45 mL) and water (3 mL) according to the process described in Step 5 of Example 1, and the crude product was purified by silica gel chromatography (PE/EtOAc (v/v)=5.5/1) to give the title compound as a pale yellow solid (2.15 g, 50.9%).

MS (ESI, pos. ion) m/z: 384.0 [M+H]$^+$; and $^1$H NMR (400 MHz, DMSO-d$_6$): δ (ppm) 8.40 (s, 2H), 7.73 (s, 1H), 7.52-7.46 (m, 2H), 7.43-7.38 (m, 2H), 7.36 (s, 1H), 3.78-3.75 (m, 4H), 3.44-3.41 (m, 4H), 1.43 (s, 9H).

Step 2) Synthesis of 2-(2-(piperazin-1-yl)pyrimidin-5-yl)benzamide hydrochloride The title compound was prepared using a solution of hydrogen chloride in ethyl acetate (10 mL, 4 N) and tert-butyl 4-(5-(2-carbamoylphenyl)pyrimidin-2-yl)piperazine-1-carboxylate (2.15 g, 5.61 mmol) according to the process described in Step 6 of Example 1 as a pale yellow solid (1.70 g, 95.0%).

MS (ESI, pos. ion) m/z: 284.0 [M+H−HCl]$^+$.

Step 3) Synthesis of 2-(2-(4-(4-(5-cyano-1H-indol-3-yl)butyl)piperazin-1-yl)pyrimidin-5-yl) benzamide The title compound was prepared using 4-(5-cyano-1H-indol-3-yl)butyl 4-methylbenzenesulfonate (558 mg, 1.51 mmol), 2-(2-(piperazin-1-yl)pyrimidin-5-yl)benzamide hydrochloride (440 mg, 1.38 mmol), sodium carbonate (437 mg, 4.13 mmol) and potassium iodide (23 mg, 0.13 mmol) in acetonitrile (15 mL) according to the process described in Step 7 of Example 1, and the crude product was purified by silica gel chromatography (DCM/MeOH (v/v)=50/1) to give the title compound as a pale yellow solid (335 mg, 50.8%).

MS (ESI, pos. ion) m/z: 479.9 [M+H]$^+$;

$^1$H NMR (600 MHz, DMSO-d$_6$): δ (ppm) 11.37 (s, 1H), 8.37 (s, 2H), 8.08 (s, 1H), 7.75 (s, 1H), 7.49-7.46 (m, 3H), 7.41-7.39 (m, 4H), 7.34 (s, 1H), 3.75 (brs, 4H), 2.74 (t, J=6.6 Hz, 2H), 2.41 (brs, 4H), 2.35 (t, J=6.6 Hz, 2H), 1.68-1.66 (m, 2H), 1.53-1.51 (m, 2H); and $^{13}$C NMR (150 MHz, DMSO-d$_6$): δ (ppm) 171.0, 160.2, 156.7, 138.0, 136.8, 133.2, 129.6, 129.4, 127.8, 127.2, 127.1, 124.9, 124.3, 123.6, 122.2, 121.0, 116.1, 112.6, 100.1, 57.6, 52.7, 43.4, 27.7, 26.1, 24.1.

Example 4

2-(2-(4-(3-(5-cyano-1H-indol-3-yl)propyl)piperazin-1-yl)pyrimidin-5-yl) benzamide

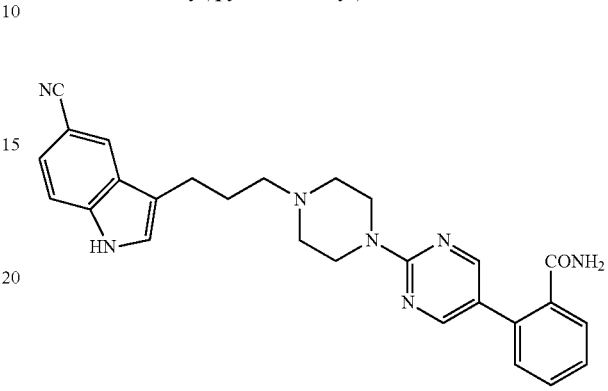

The title compound was prepared using 3-(5-cyano-1H-indol-3-yl)propyl 4-methylbenzenesulfonate (665 mg, 1.88 mmol), 2-(2-(piperazin-1-yl)pyrimidin-5-yl)benzamide hydrochloride (500 mg, 1.56 mmol), sodium carbonate (497 mg, 4.69 mmol) and potassium iodide (26 mg, 0.16 mmol) in acetonitrile (20 mL) according to the process described in Step 7 of Example 1, and the crude product was purified by silica gel chromatography (DCM/MeOH (v/v)=50/1) to give the title compound as a pale yellow solid (458 mg, 63.0%).

MS (ESI, pos. ion) m/z: 466.3 [M+H]$^+$; and $^1$H NMR (600 MHz, DMSO-d$_6$): δ (ppm) 11.39 (s, 1H), 8.38 (s, 2H), 8.11 (s, 1H), 7.75 (s, 1H), 7.51-7.46 (m, 3H), 7.41-7.38 (m, 4H), 7.36 (s, 1H), 3.78 (brs, 4H), 2.76 (t, J=6.6 Hz, 2H), 2.44 (brs, 4H), 2.36 (t, J=6.6 Hz, 2H), 1.85-1.83 (m, 2H).

Example 5

4-(2-(4-(4-(5-cyano-1H-indol-3-yl)butyl)piperazin-1-yl)pyrimidin-5-yl)benzamide

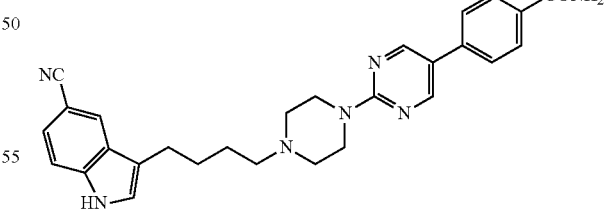

Step 1) Synthesis of tert-butyl 4-(5-(4-carbamoyl-phenyl)pyrimidin-2-yl)piperazine-1-carboxylate The title compound was prepared using tert-butyl 4-(5-bromopyrimidin-2-yl)piperazine-1-carboxylate (800 mg, 2.33 mmol), (4-carbamoylphenyl) boric acid (384 mg, 2.33 mmol), Pd(dppf)Cl$_2$ (172 mg, 0.23 mmol) and caesium carbonate (2.28 g, 6.99 mmol) in a mixture of 1,4-dioxane (15 mL) and water (1 mL) according to the process described in Step 5 of Example 1, and the crude product was purified by silica gel chromatography (PE/EtOAc (v/v)=1/2) to give the title compound as a pale yellow solid (615 mg, 68.8%).

MS (ESI, pos. ion) m/z: 384.2 [M+H]$^+$; and
$^1$H NMR (400 MHz, DMSO-d$_6$): δ (ppm) 8.81 (s, 2H), 7.95 (d, J=8.3 Hz, 2H), 7.75 (d, J=8.2 Hz, 2H), 7.37 (s, 2H), 3.84-3.75 (m, 4H), 3.47-3.40 (m, 4H), 1.44 (s, 9H).

Step 2) Synthesis of 4-(2-(piperazin-1-yl)pyrimidin-5-yl)benzamide hydrochloride The title compound was prepared using a solution of hydrogen chloride in ethyl acetate (10 mL, 4 N) and tert-butyl 4-(5-(4-carbamoylphenyl)pyrimidin-2-yl)piperazine-1-carboxylate (610 mg, 1.59 mmol) according to the process described in Step 6 of Example 1 as a pale yellow solid (500 mg, 98.2%).

MS (ESI, pos. ion) m/z: 284.2 [M+H–HCl]$^+$; and
$^1$H NMR (400 MHz, D$_2$O): δ (ppm) δ 8.77 (s, 2H), 7.81 (d, J=8.3 Hz, 2H), 7.63 (d, J=8.4 Hz, 2H), 4.14-4.03 (m, 4H), 3.43-3.36 (m, 4H).

Step 3) Synthesis of 4-(2-(4-(4-(5-cyano-1H-indol-3-yl)butyl)piperazin-1-yl)pyrimidin-5-yl) benzamide The title compound was prepared using 4-(5-cyano-1H-indol-3-yl)butyl 4-methylbenzenesulfonate (317 mg, 0.86 mmol), 4-(2-(piperazin-1-yl)pyrimidin-5-yl)benzamide hydrochloride (250 mg, 0.78 mmol), sodium carbonate (249 mg, 2.35 mmol) and potassium iodide (13 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (170 mg, 45.3%).

MS (ESI, pos. ion) m/z: 479.9 [M+H]$^+$; and
$^1$H NMR (600 MHz, DMSO-d$_6$): δ (ppm) 11.38 (s, 1H), 8.78 (s, 2H), 8.09 (s, 1H), 8.01 (s, 1H), 7.95 (d, J=8.4 Hz, 2H), 7.74 (d, J=8.4 Hz, 2H), 7.50 (d, J=8.4 Hz, 1H), 7.44-7.37 (m, 2H), 7.35 (d, J=1.8 Hz, 1H), 3.78 (brs, 4H), 2.74 (t, J=7.5 Hz, 2H), 2.41 (brs, 4H), 2.37 (s, 2H), 1.68 (dt, J=15.0, 7.6 Hz, 2H), 1.54 (dd, J=14.0, 7.1 Hz, 2H).

Example 6

4-(2-(4-(3-(5-cyano-1H-indol-3-yl)propyl)piperazin-1-yl)pyrimidin-5-yl) benzamide

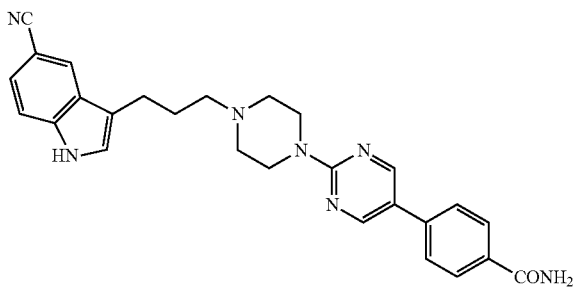 [SMILES: N#Cc1ccc2[nH]cc(CCCN3CCN(c4ncc(-c5ccc(C(N)=O)cc5)cn4)CC3)c2c1]

The title compound was prepared using 3-(5-cyano-1H-indol-3-yl)propyl 4-methylbenzenesulfonate (330 mg, 0.93 mmol) reacted with 4-(2-(piperazin-1-yl)pyrimidin-5-yl)benzamide hydrochloride (248 mg, 0.78 mmol), sodium carbonate (247 mg, 2.33 mmol) and potassium iodide (13 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (176 mg, 48.8%).

MS (ESI, pos. ion) m/z: 466.9 [M+H]$^+$;
$^1$H NMR (400 MHz, DMSO-d$_6$): δ (ppm) 11.38 (s, 1H), 8.77 (s, 2H), 8.11 (s, 1H), 8.00 (s, 1H), 7.95 (d, J=8.3 Hz, 2H), 7.74 (d, J=8.3 Hz, 2H), 7.50 (d, J=8.4 Hz, 1H), 7.40 (dd, J=8.5, 1.2 Hz, 1H), 7.36 (s, 2H), 3.81 (brs, 4H), 2.76 (t, J=7.2 Hz, 2H), 2.44 (brs, 4H), 2.36 (t, J=7.2 Hz, 2H), 1.90-1.78 (m, 2H); and
$^{13}$C NMR (150 MHz, DMSO-d$_6$): δ (ppm) 167.9, 161.1, 156.4, 138.4, 138.2, 133.1, 128.7, 127.7, 125.5, 125.4, 124.7, 124.0, 121.4, 116.3, 113.0, 110.0, 100.7, 57.8, 53.1, 44.1, 27.6, 22.4.

Example 7

3-(4-(4-(5-(4-fluorophenyl)pyrimidin-2-yl)piperazin-1-yl)butyl)-1H-indole-5-carbonitrile

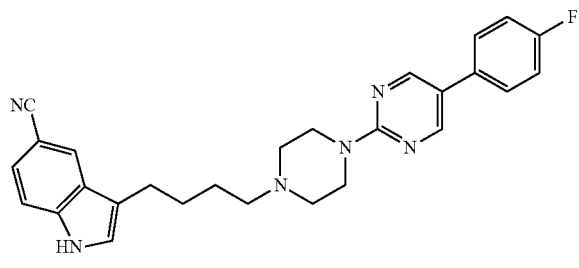 [SMILES: N#Cc1ccc2[nH]cc(CCCCN3CCN(c4ncc(-c5ccc(F)cc5)cn4)CC3)c2c1]

Step 1) Synthesis of tert-butyl 4-(5-(4-fluorophenyl) pyrimidin-2-yl)piperazine-1-carboxylate The title compound was prepared using tert-butyl 4-(5-bromopyrimidin-2-yl)piperazine-1-carboxylate (840 mg, 2.45 mmol), (4-fluorophenyl) boric acid (342 mg, 2.45 mmol), Pd(dppf)Cl$_2$ (180 mg, 0.24 mmol) and caesium carbonate (2.39 g, 7.34 mmol) in a mixture of 1,4-dioxane (15 mL) and water (1 mL) according to the process described in Step 5 of Example 1, and the crude product was purified by silica gel chromatography (PE/EtOAc (v/v)=1/2) to give the title compound as a white solid (336 mg, 38.3%).

MS (ESI, pos. ion) m/z: 359.3 [M+H]$^+$; and
$^1$H NMR (600 MHz, CDCl$_3$): δ (ppm) 8.50 (s, 2H), 7.43-7.39 (m, 2H), 7.12 (t, J=8.6 Hz, 2H), 3.92 (t, J=4.8 Hz, 4H), 3.50 (t, J=4.8 Hz, 4H), 1.49 (s, 9H).

Step 2) Synthesis of 5-(4-fluorophenyl)-2-(piperazin-1-yl)pyrimidine hydrochloride The title compound was prepared using a solution of hydrogen chloride in ethyl acetate (10 mL, 4 N) and tert-butyl 4-(5-(4-fluorophenyl)pyrimidin-2-yl)piperazine-1-carboxylate (330 mg, 0.92 mmol) according to the process described in Step 6 of Example 1 as a pale yellow solid (269 mg, 99.1%).

MS (ESI, pos. ion) m/z: 295.2 [M+H]$^+$; and
$^1$H NMR (400 MHz, CDCl$_3$): δ (ppm) 8.49 (s, 2H), 7.44-7.38 (m, 2H), 7.16-7.02 (m, 2H), 3.84 (t, J=4.8 Hz, 4H), 2.95 (t, J=4.8 Hz, 4H).

Step 3) 3-(4-(4-(5-(4-fluorophenyl)pyrimidin-2-yl)piperazin-1-yl)butyl)-1H-indole-5-carbonitrile The title compound was prepared using 4-(5-cyano-1H-indol-3-yl)butyl 4-methylbenzenesulfonate (390 mg, 1.06 mmol), 5-(4-(fluorophenyl)-2-(pyrimidin-1-yl)pyrimidine hydrochloride (260 mg, 0.88 mmol), sodium carbonate (280 mg, 2.65 mmol) and potassium iodide (15 mg, 0.09 mmol) in acetonitrile (15 mL) according to the process described in Step 7 of Example 1, and the crude product was purified by silica gel chromatography (DCM/MeOH (v/v)=50/1) to give the title compound as a pale yellow solid (281 mg, 70.2%).

MS (ESI, pos. ion) m/z: 455.2 [M+H]$^+$;

$^1$H NMR (600 MHz, CDCl$_3$): δ (ppm) 8.69 (s, 1H), 8.48 (s, 2H), 7.95 (s, 1H), 7.41-7.40 (m, 2H), 7.39 (s, 2H), 7.14-7.08 (m, 3H), 3.95-3.83 (m, 4H), 2.78 (t, J=7.5 Hz, 2H), 2.56-2.48 (m, 4H), 2.48-2.36 (m, 2H), 1.79-1.69 (m, 2H), 1.68-1.54 (m, 2H); and $^{13}$H NMR (150 MHz, CDCl$_3$): δ (ppm) 162.4 (d, J=245.1 Hz), 161.0, 155.8, 138.1, 131.8 (d, J=3.3 Hz), 127.5 (d, J=8.1 Hz), 127.4, 124.8, 124.7, 123.4, 122.1, 121.0, 117.6, 116.1, 112.0, 102.1, 58.5, 53.2, 43.9, 27.9, 26.7, 24.8.

Example 8

3-(3-(4-(5-(4-fluorophenyl)pyrimidin-2-yl)piperazin-1-yl)propyl)-1H-indole-5-carbonitrile

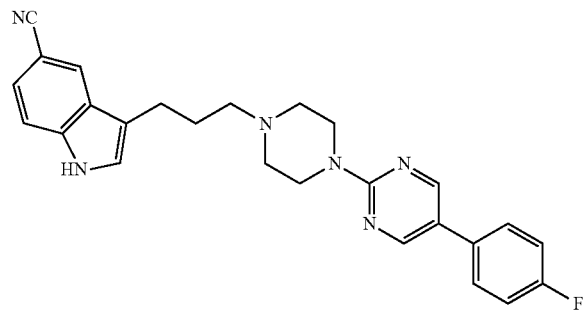 [SMILES: N#Cc1ccc2[nH]cc(CCCN3CCN(c4ncc(-c5ccc(F)cc5)cn4)CC3)c2c1]

The title compound was prepared using 3-(5-cyano-1H-indol-3-yl)propyl 4-methylbenzenesulfonate (375 mg, 1.06 mmol), 5-(4-(fluorophenyl)-2-(pyrimidin-1-yl)pyrimidine hydrochloride (260 mg, 0.88 mmol), sodium carbonate (280 mg, 2.65 mmol) and potassium iodide (15 mg, 0.09 mmol) in acetonitrile (15 mL) according to the process described in Step 7 of Example 1, and the crude product was purified by silica gel chromatography (DCM/MeOH (v/v)=50/1) to give the title compound as a pale yellow solid (281 mg, 70.2%).

MS (ESI, pos. ion) m/z: 441.3 [M+H]$^+$;

$^1$H NMR (600 MHz, CDCl$_3$): δ (ppm) 8.52 (s, 2H), 8.48 (s, 1H), 8.01 (s, 1H), 7.44-7.42 (m, 2H), 7.16-7.13 (m, 3H), 4.00-3.82 (m, 4H), 2.84 (t, J=7.4 Hz, 2H), 2.62-2.53 (m, 4H), 2.53-2.45 (m, 2H), 2.03-1.89 (m, 2H); and $^{13}$C NMR (150 MHz, CDCl$_3$): δ (ppm) 162.4 (d, J=245.1 Hz), 161.0, 155.8, 138.0, 131.8 (d, J=3.3 Hz), 127.5 (d, J=8.1 Hz), 127.4, 124.9, 124.8, 123.3, 122.2, 120.8, 117.5, 116.1, 111.9, 102.4, 58.1, 53.2, 43.9, 27.2, 22.6.

Example 9

3-(4-(4-(5-(2-methoxyphenyl)pyrimidin-2-yl)piperazin-1-yl)butyl)-1H-indole-5-carbonitrile

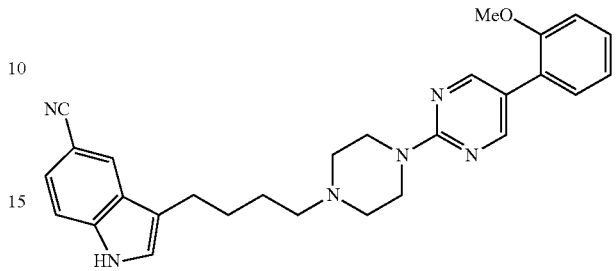

Step 1) Synthesis of tert-butyl 4-(5-(2-methoxyphenyl)pyrimidin-2-yl)piperazine-1-carboxylate The title compound was prepared using tert-butyl 4-(5-bromopyrimidin-2-yl)piperazine-1-carboxylate (840 mg, 2.62 mmol), (2-methoxyphenyl) boric acid (398 mg, 2.62 mmol), Pd(dppf)Cl$_2$ (197 mg, 0.26 mmol) and caesium carbonate (2.56 g, 7.87 mmol) in a mixture of 1,4-dioxane (15 mL) and water (1 mL) according to the process described in Step 5 of Example 1, and the crude product was purified by silica gel chromatography (PE/EtOAc (v/v)=1/2) to give the title compound as a white solid (293 mg, 30.1%).

MS (ESI, pos. ion) m/z: 371.2 [M+H]$^+$; and $^1$H NMR (600 MHz, DMSO-d$_6$): δ (ppm) 8.80 (s, 2H), 8.14 (dd, J=8.0, 1.6 Hz, 1H), 7.63 (d, J=7.7 Hz, 1H), 6.87-6.75 (m, 2H), 3.84 (s, 3H), 3.84-3.76 (m, 4H), 3.50-3.39 (m, 4H), 1.44 (s, 9H).

Step 2) Synthesis of 5-(2-methoxyphenyl)-2-(piperazin-1-yl)pyrimidine hydrochloride The title compound was prepared using a solution of hydrogen chloride in ethyl acetate (10 mL, 4 N) and tert-butyl 4-(5-(2-methoxyphenyl)pyrimidin-2-yl)piperazine-1-carboxylate (290 mg, 0.78 mmol) according to the process described in Step 6 of Example 1 as a pale yellow solid (228 mg, 94.9%).

MS (ESI, pos. ion) m/z: 306.2 [M+H]$^+$; and $^1$H NMR (600 MHz, DMSO-d$_6$): δ (ppm) 8.79 (s, 2H), 8.13 (dd, J=7.8, 1.6 Hz, 1H), 7.63 (d, J=7.8 Hz, 1H), 6.88-6.75 (m, 2H), 3.83 (s, 3H), 3.80 (t, J=4.8 Hz, 4H), 3.45 ((t, J=4.8 Hz, 4H), 1.45 (s, 9H).

Step 3) 3-(4-(4-(5-(2-methoxyphenyl)pyrimidin-2-yl)piperazin-1-yl)butyl)-1H-indole-5-carbonitrile The title compound was prepared using 4-(5-cyano-1H-indol-3-yl)butyl 4-methylbenzenesulfonate (317 mg, 0.86 mmol), 5-(2-(methoxyphenyl)-2-(pyrimidin-1-yl)pyrimidine hydrochloride (220 mg, 0.72 mmol), sodium carbonate (228 mg, 2.15 mmol) and potassium iodide (12 mg, 0.07 mmol) in acetonitrile (15 mL) according to the process described in Step 7 of Example 1, and the crude product was purified by silica gel chromatography (DCM/MeOH (v/v)=50/1) to give the title compound as a pale yellow solid (193 mg, 57.7%).

MS (ESI, pos. ion) m/z: 467.3 [M+H]$^+$; and $^1$H NMR (600 MHz, CDCl$_3$): δ (ppm) 8.82 (s, 1H), 8.54 (s, 2H), 7.97 (s, 1H), 7.41 (s, 2H), 7.33 (td, J=8.2, 1.7 Hz, 1H), 7.30-7.24 (m, 1H), 7.11 (d, J=2.0 Hz, 1H), 7.04 (td, J=7.5, 0.9 Hz, 1H), 6.99 (d, J=8.2 Hz, 1H), 3.95-3.86 (m, 4H), 3.83 (s, 3H), 2.80 (t, J=7.4 Hz, 2H), 2.59-2.50 (m, 4H), 2.50-2.41 (m, 2H), 1.79-1.76 (m, 2H), 1.68-1.63 (m, 2H).

Example 10

3-(4-(4-(5-(2-methoxyphenyl)pyrimidin-2-yl)piperazin-1-yl)butyl)-1H-indole-5-carbonitrile

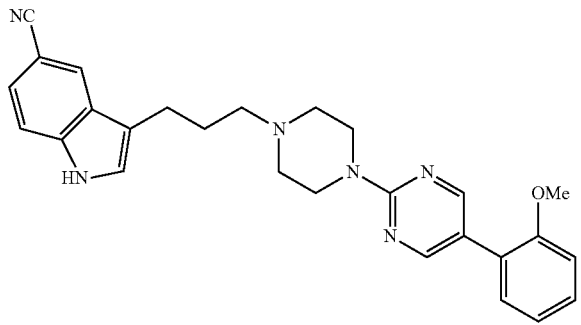 [SMILES: COc1ccccc1-c1cnc(N2CCN(CCCc3c[nH]c4ccc(C#N)cc34)CC2)nc1]

The title compound was prepared using 3-(5-cyano-1H-indol-3-yl)propyl 4-methylbenzenesulfonate (347 mg, 0.98 mmol), 5-(2-(methoxyphenyl)-2-(pyrimidin-1-yl)pyrimidine hydrochloride (250 mg, 0.81 mmol), sodium carbonate (259 mg, 2.44 mmol) and potassium iodide (14 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (217 mg, 60.0%).

MS (ESI, pos. ion) m/z: 453.3 [M+H]$^+$;
$^1$H NMR (600 MHz, CDCl$_3$): δ (ppm) 8.78 (s, 1H), 8.54 (s, 2H), 7.99 (s, 1H), 7.41 (s, 2H), 7.32 (td, J=8.2, 1.7 Hz, 1H), 7.27 (dd, J=6.9, 1.8 Hz, 1H), 7.13 (d, J=2.4 Hz, 1H), 7.04 (td, J=7.4, 0.6 Hz, 1H), 6.98 (d, J=8.2 Hz, 1H), 3.98-3.87 (m, 4H), 3.82 (s, 3H), 2.82 (t, J=7.5 Hz, 2H), 2.58-2.50 (m, 4H), 2.50-2.43 (m, 2H), 1.99-1.94 (m, 2H); and
$^{13}$H NMR (150 MHz, CDCl$_3$): δ (ppm) 160.5, 157.8, 156.6, 138.0, 129.5, 128.9, 127.5, 124.9, 124.8, 124.7, 123.4, 121.2, 120.9, 120.4, 117.3, 112.0, 111.3, 102.1, 58.2, 55.5, 53.2, 43.9, 27.2, 22.6.

Example 11

3-(4-(4-(5-(4-chlorophenyl)pyrimidin-2-yl)piperazin-1-yl)butyl)-1H-indole-5-carbonitrile

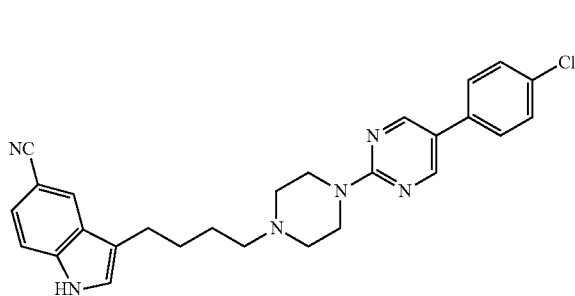 [SMILES: N#Cc1ccc2[nH]cc(CCCCN3CCN(c4ncc(-c5ccc(Cl)cc5)cn4)CC3)c2c1]

Step 1) Synthesis of tert-butyl 4-(5-(4-chlorophenyl)pyrimidin-2-yl)piperazine-1-carboxylate The title compound was prepared using tert-butyl 4-(5-bromopyrimidin-2-yl)piperazine-1-carboxylate (840 mg, 2.45 mmol), (4-chlorophenyl)boric acid (383 mg, 2.45 mmol), Pd(dppf)Cl$_2$ (180 mg, 0.24 mmol) and caesium carbonate (2.39 g, 7.34 mmol) in a mixture of 1,4-dioxane (15 mL) and water (1 mL) according to the process described in Step 5 of Example 1, and the crude product was purified by silica gel chromatography (PE/EtOAc (v/v)=1/2) to give the title compound as a white solid (333 mg, 36.3%).
$^1$H NMR (600 MHz, CDCl$_3$): δ (ppm) 8.51 (s, 2H), 7.55 (dd, J=7.8, 1.6 Hz, 2H), 7.35 (dd, J=7.8, 1.6 Hz, 2H), 3.93 (t, J=4.8 Hz, 4H), 3.51 (t, J=4.8 Hz, 4H), 1.49 (s, 9H).

Step 2) Synthesis of 5-(4-chlorophenyl)-2-(piperazin-1-yl)pyrimidine hydrochloride The title compound was prepared using a solution of hydrogen chloride in ethyl acetate (10 mL, 4 N) and tert-butyl 4-(5-(4-chlorophenyl)pyrimidin-2-yl)piperazine-1-carboxylate (330 mg, 0.77 mmol) according to the process described in Step 6 of Example 1 as a pale yellow solid (229 mg, 96.5%).
$^1$H NMR (600 MHz, CDCl$_3$): δ (ppm) 8.50 (s, 2H), 7.42-7.39 (m, 4H), 3.53 (t, J=4.8 Hz, 4H), 2.95 (t, J=4.8 Hz, 4H).

Step 3) 3-(4-(4-(5-(4-chlorophenyl)pyrimidin-2-yl)piperazin-1-yl)butyl)-1H-indole-5-carbonitrile The title compound was prepared using 4-(5-cyano-1H-indol-3-yl)butyl 4-methylbenzenesulfonate (313 mg, 0.85 mmol), 5-(4-(chlorophenyl)-2-(pyrimidin-1-yl)pyrimidine hydrochloride (220 mg, 0.71 mmol), sodium carbonate (225 mg, 2.12 mmol) and potassium iodide (12 mg, 0.07 mmol) in acetonitrile (15 mL) according to the process described in Step 7 of Example 1, and the crude product was purified by silica gel chromatography (DCM/MeOH (v/v)=50/1) to give the title compound as a pale yellow solid (204 mg, 61.3%).

MS (ESI, pos. ion) m/z: 472.2 [M+H]$^+$;
$^1$H NMR (600 MHz, CDCl$_3$): δ (ppm) 8.53 (s, 1H), 8.50 (s, 2H), 7.95 (s, 1H), 7.41-7.36 (m, 6H), 7.10 (d, J=1.9 Hz, 1H), 3.91-3.84 (m, 4H), 2.78 (t, J=7.5 Hz, 2H), 2.54-2.48 (m, 4H), 2.46-2.39 (m, 2H), 1.79-1.70 (m, 2H), 1.67-1.58 (m, 2H); and
$^{13}$H NMR (150 MHz, CDCl$_3$): δ (ppm) 161.0, 155.8, 138.0, 134.2, 133.3, 129.3, 127.5, 127.0, 124.8, 124.7, 123.3, 121.8, 120.9, 117.6, 111.9, 102.2, 58.5, 53.2, 43.9, 27.9, 26.7, 24.8.

Example 12

3-(3-(4-(5-(4-chlorophenyl)pyrimidin-2-yl)piperazin-1-yl)propyl)-1H-indole-5-carbonitrile

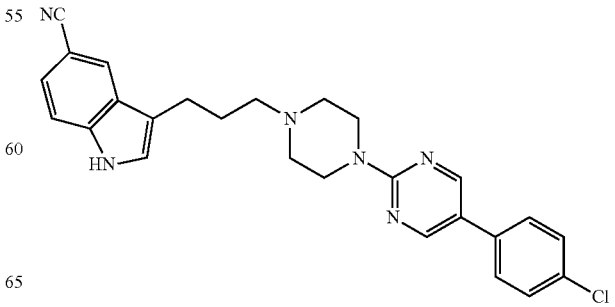

The title compound was prepared using 3-(5-cyano-1H-indol-3-yl)propyl 4-methylbenzenesulfonate (328 mg, 0.93 mmol), 5-(4-chlorophenyl)-2-(pyrimidin-1-yl)pyrimidine hydrochloride (240 mg, 0.77 mmol), sodium carbonate (245 mg, 2.31 mmol) and potassium iodide (13 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (200 mg, 56.8%).

MS (ESI, pos. ion) m/z: 457.3 [M+H]$^+$;

$^1$H NMR (400 MHz, CDCl$_3$): δ (ppm) 8.65 (s, 1H), 8.50 (s, 2H), 7.98 (s, 1H), 7.39 (m, 6H), 7.12 (s, 1H), 3.90 (brs, 4H), 2.81 (t, J=7.1 Hz, 2H), 2.53 (brs, 4H), 2.50-2.38 (m, 2H), 2.04-1.80 (m, 2H); and $^{13}$C NMR (100 MHz, CDCl$_3$): δ (ppm) 161.0, 155.7, 138.0, 134.2, 133.3, 129.3, 127.5, 127.0, 124.8, 124.7, 123.3, 121.8, 120.9, 117.4, 111.9, 102.3, 58.1, 53.1, 43.9, 27.2, 22.5.

Example 13

3-(4-(4-(5-(2,4-difluorophenyl)pyrimidin-2-yl)piperazin-1-yl)butyl)-1H-indole-5-carbonitrile

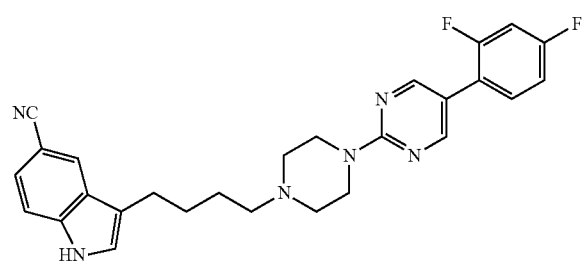 [SMILES: N#Cc1ccc2[nH]cc(CCCCN3CCN(c4ncc(-c5ccc(F)cc5F)cn4)CC3)c2c1]

Step 1) Synthesis of tert-butyl 4-(5-(2,4-difluorophenyl)pyrimidin-2-yl)piperazine-1-carboxylate The title compound was prepared using tert-butyl 4-(5-bromopyrimidin-2-yl)piperazine-1-carboxylate (840 mg, 2.45 mmol), (2,4-difluorophenyl)boric acid (386 mg, 2.45 mmol), Pd(dppf)Cl$_2$ (180 mg, 0.24 mmol) and caesium carbonate (2.39 g, 7.34 mmol) in a mixture of 1,4-dioxane (15 mL) and water (1 mL) according to the process described in Step 5 of Example 1, and the crude product was purified by silica gel chromatography (PE/EtOAc (v/v)=1/2) to give the title compound as a white solid (399 mg, 43.3%).

MS (ESI, pos. ion) m/z: 377.2 [M+H]$^+$; and $^1$H NMR (600 MHz, CDCl$_3$): δ (ppm) 8.78 (d, J=1.2 Hz, 2H), 7.42 (td, J=8.6 Hz, 6.2 Hz, 1H), 7.05 (td, J=7.8 Hz, 1.6 Hz, 1H), 7.03-6.99 (m, 1H), 3.92 (t, J=4.8 Hz, 4H), 3.49 (t, J=4.8 Hz, 4H), 1.49 (s, 9H).

Step 2) Synthesis of 5-(2,4-difluorophenyl)-2-(piperazin-1-yl)pyrimidine hydrochloride The title compound was prepared using a solution of hydrogen chloride in ethyl acetate (10 mL, 4 N) and tert-butyl 4-(5-(2,4-difluorophenyl)pyrimidin-2-yl)piperazine-1-carboxylate (390 mg, 1.04 mmol) according to the process described in Step 6 of Example 1 as a pale yellow solid (295 mg, 92.8%).

MS (ESI, pos. ion) m/z: 313.1 [M+H]$^+$; and $^1$H NMR (600 MHz, CDCl$_3$): δ (ppm) 8.78 (d, J=1.2 Hz, 2H), 7.43 (td, J=8.8 Hz, 6.0 Hz, 1H), 7.07-7.04 (m, 1H), 7.03-7.00 (m, 1H), 3.52 (t, J=4.8 Hz, 4H), 2.91 (t, J=4.8 Hz, 4H), 1.46 (s, 9H).

Step 3) Synthesis of 3-(4-(4-(5-(2,4-difluorophenyl)pyrimidin-2-yl)piperazin-1-yl)butyl)-1H-indole-5-carbonitrile The title compound was prepared using 4-(5-cyano-1H-indol-3-yl)butyl 4-methylbenzenesulfonate (410 mg, 1.11 mmol), 5-(2,4-chlorophenyl)-2-(pyrimidin-1-yl)pyrimidine hydrochloride (290 mg, 0.93 mmol), sodium carbonate (294 mg, 2.78 mmol) and potassium iodide (15 mg, 0.09 mmol) in acetonitrile (15 mL) according to the process described in Step 7 of Example 1, and the crude product was purified by silica gel chromatography (DCM/MeOH (v/v)=50/1) to give the title compound as a pale yellow solid (313 mg, 71.4%).

MS (ESI, pos. ion) m/z: 473.2 [M+H]$^+$;

$^1$H NMR (600 MHz, CDCl$_3$): δ (ppm) 8.73 (s, 1H), 8.45 (s, 2H), 7.95 (s, 1H), 7.38 (s, 2H), 7.30 (dd, J=15.0, 8.4 Hz, 1H), 7.09 (s, 1H), 6.94 (t, J=8.3 Hz, 1H), 6.92-6.87 (m, 1H), 3.88 (brs, 4H), 2.78 (t, J=7.4 Hz, 2H), 2.56-2.46 (m, 4H), 2.48-2.38 (m, 2H), 1.77-1.73 (m, 2H), 1.68-1.57 (m, 2H); and $^{13}$H NMR (150 MHz, CDCl$_3$): δ (ppm) 162.3 (dd, J=248.1, 11.7 Hz), 160.8, 159.8 (d, J=248.4, 11.7 Hz), 157.2, 157.1, 138.1, 130.0 (q, J=4.8 Hz), 127.5, 124.8, 124.6, 123.4, 121.0, 119.8 (dd, J=14.3, 3.8 Hz), 117.6, 117.1 (d, J=1.4 Hz), 112.0, 111.9 (dd, J=21.2, 3.3 Hz), 104.6 (t, J=25.7 Hz), 102.1, 58.5, 53.1, 43.8, 27.9, 26.6, 24.8.

Example 14

3-(3-(4-(5-(2,4-difluorophenyl)pyrimidin-2-yl)piperazin-1-yl)propyl)-1H-indole-5-carbonitrile

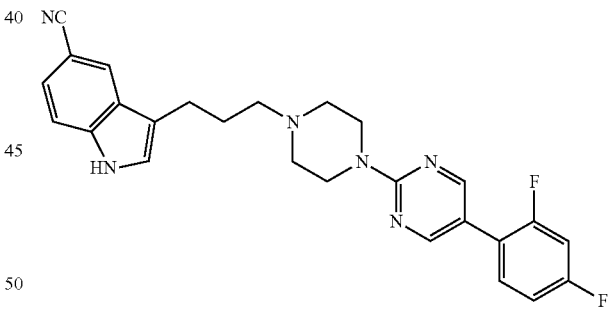

The title compound was prepared using 3-(5-cyano-1H-indol-3-yl)propyl 4-methylbenzenesulfonate (340 mg, 0.96 mmol), 5-(2,4-chlorophenyl)-2-(pyrimidin-1-yl)pyrimidine hydrochloride (250 mg, 0.80 mmol), sodium carbonate (254 mg, 2.40 mmol) and potassium iodide (13 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (270 mg, 73.6%).

MS (ESI, pos. ion) m/z: 459.2 [M+H]$^+$;

$^1$H NMR (600 MHz, CDCl$_3$): δ (ppm) 8.58 (s, 1H), 8.45 (s, 2H), 7.98 (s, 1H), 7.40 (s, 2H), 7.30 (dd, J=15.0, 8.5 Hz, 1H), 7.12 (s, 1H), 6.95 (t, J=7.8 Hz, 2H), 6.91 (t, J=7.8 Hz, 2H), 3.90 (brs, 4H), 2.81 (t, J=7.4 Hz, 2H), 2.58-2.49 (m, 4H), 2.49-2.40 (m, 2H), 2.00-1.90 (m, 2H); and ¹³H NMR (150 MHz, CDCl₃): δ (ppm) 162.3 (dd, J=248.0, 11.7 Hz), 160.8, 159.8 (dd, J=248.3, 11.9 Hz), 157.2, 157.1, 138.0, 130.0 (q, J=5.0 Hz), 127.5, 124.8, 124.7, 123.4, 120.9, 119.8 (dd, J=14.3, 3.8 Hz), 117.4, 117.1 (d, J=2.0 Hz), 112.0, 111.9 (dd, J=21.2, 3.8 Hz), 104.6 (t, J=25.7 Hz), 102.2, 58.1, 53.2, 43.9, 27.3, 22.6.

Example 15

3-(4-(4-(5-(4-fluoro-2-methoxyphenyl)pyrimidin-2-yl)piperazin-1-yl)butyl)-1H-indole-5-carbonitrile

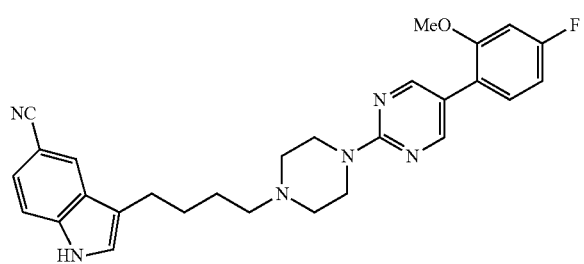 [SMILES: COc1cc(F)ccc1-c1cnc(N2CCN(CCCCc3c[nH]c4ccc(C#N)cc34)CC2)nc1]

Step 1) Synthesis of tert-butyl 4-(5-(4-fluoro-2-methoxyphenyl)pyrimidin-2-yl)piperazine-1-carboxylate The title compound was prepared using tert-butyl 4-(5-bromopyrimidin-2-yl)piperazine-1-carboxylate (840 mg, 2.45 mmol), (4-fluoro-2-methoxyphenyl)boric acid (416 mg, 2.45 mmol), Pd(dppf)Cl₂ (180 mg, 0.24 mmol) and caesium carbonate (2.39 g, 7.34 mmol) in a mixture of 1,4-dioxane (15 mL) and water (1 mL) according to the process described in Step 5 of Example 1, and the crude product was purified by silica gel chromatography (PE/EtOAc (v/v)=1/2) to give the title compound as a white solid (368 mg, 38.7%).

¹H NMR (600 MHz, CDCl₃): δ (ppm) 8.73 (s, 2H), 7.26 (dd, J=8.4, 6.5 Hz, 1H), 6.83-6.72 (m, 2H), 3.93 (t, J=4.8 Hz, 4H), 3.83 (s, 3H), 3.48 (t, J=4.8 Hz, 4H), 1.49 (s, 9H).

Step 2) Synthesis of 5-(4-fluoro-2-methoxyphenyl)-2-(piperazin-1-yl)pyrimidine hydrochloride The title compound was prepared using a solution of hydrogen chloride in ethyl acetate (10 mL, 4 N) and tert-butyl 4-(5-(4-fluoro-2-methoxyphenyl)pyrimidin-2-yl)piperazine-1-carboxylate (360 mg, 0.93 mmol) according to the process described in Step 6 of Example 1 as a pale yellow solid (275 mg, 96.7%).

¹H NMR (400 MHz, CDCl₃): δ (ppm) 8.72 (s, 2H), 7.25 (dd, J=8.4, 6.4 Hz, 1H), 6.82-6.70 (m, 2H), 3.83 (s, 3H), 3.50 (t, J=4.8 Hz, 4H), 2.87 (t, J=4.8 Hz, 4H).

Step 3) Synthesis of 3-(4-(4-(5-(4-fluoro-2-methoxyphenyl)pyrimidin-2-yl)piperazin-1-yl)butyl)-1H-indole-5-carbonitrile The title compound was prepared using 4-(5-cyano-1H-indol-3-yl)butyl 4-methylbenzenesulfonate (367 mg, 0.10 mmol), 5-(4-fluoro-2-methoxyphenyl)-2-(pyrimidin-1-yl)pyrimidine hydrochloride (270 mg, 0.83 mmol), sodium carbonate (264 mg, 2.49 mmol) and potassium iodide (14 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (274 mg, 68.0%).

MS (ESI, pos. ion) m/z: 485.2 [M+H]⁺;

¹H NMR (600 MHz, CDCl₃): δ (ppm) 8.58 (s, 1H), 8.45 (s, 2H), 7.95 (s, 1H), 7.44-7.36 (m, 2H), 7.18 (dd, J=8.3, 6.7 Hz, 1H), 7.10 (s, 1H), 6.76-6.63 (m, 2H), 3.91-3.83 (m, 4H), 3.79 (s, 3H), 2.78 (t, J=7.5 Hz, 2H), 2.55-2.47 (m, 4H), 2.47-2.39 (m, 2H), 1.77-1.72 (m, 2H), 1.66-1.60 (m, 2H); and ¹³C NMR (150 MHz, CDCl₃): δ (ppm) 163.2 (d, J=245.0 Hz), 160.5, 157.7 (d, J=9.6 Hz), 157.6, 138.0, 130.2 (d, J=9.8 Hz), 127.5, 124.8, 124.7, 123.3, 120.9, 120.8 (d, J=3.3 Hz), 119.6, 117.6, 111.9, 107.4 (d, J=21.0 Hz), 102.2, 99.6 (d, J=25.7 Hz), 58.6, 55.7, 53.2, 43.9, 27.9, 26.7, 24.8.

Example 16

3-(3-(4-(5-(4-fluoro-2-methoxyphenyl)pyrimidin-2-yl)piperazin-1-yl)propyl)-1H-indole-5-carbonitrile

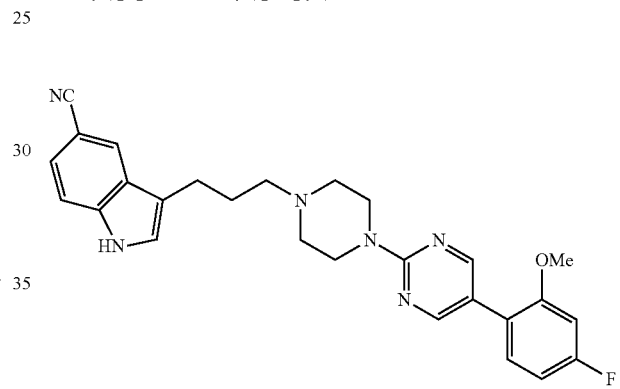

The title compound was prepared using 3-(5-cyano-1H-indol-3-yl)propyl 4-methylbenzenesulfonate (354 mg, 1.00 mmol), 5-(4-fluoro-2-methoxyphenyl)-2-(piperazin-1-yl)pyrimidine hydrochloride (270 mg, 0.83 mmol), sodium carbonate (264 mg, 2.49 mmol) and potassium iodide (14 mg, 0.08 mmol) in acetonitrile (15 mL) according to the process described in Step 7 of Example 1, and the crude product was purified by silica gel chromatography (DCM/MeOH (v/v)=50/1) to give the title compound as a pale yellow solid (263 mg, 67.2%).

MS (ESI, pos. ion) m/z: 471.2 [M+H]⁺;

¹H NMR (600 MHz, CDCl₃): δ (ppm) 8.73 (s, 1H), 8.45 (s, 2H), 7.97 (s, 1H), 7.44-7.35 (m, 2H), 7.17 (dd, J=8.4, 6.6 Hz, 1H), 7.13-7.05 (m, 1H), 6.76-6.61 (m, 2H), 3.95-3.84 (m, 4H), 3.79 (s, 3H), 2.81 (t, J=7.5 Hz, 2H), 2.58-2.50 (m, 4H), 2.50-2.39 (m, 2H), 1.99-1.83 (m, 2H); and ¹³C NMR (150 MHz, CDCl₃): δ (ppm) 163.2 (d, J=245.1 Hz), 160.5, 157.7, 157.6 (d, J=9.6 Hz), 138.0, 130.1 (d, J=9.8 Hz), 127.5, 124.8, 124.7, 123.4, 120.9, 120.8 (d, J=3.2 Hz), 119.7, 117.3, 112.0, 107.4 (d, J=21.0 Hz), 102.2, 99.6 (d, J=25.7 Hz), 58.1, 55.7, 53.2, 43.9, 27.3, 22.6.

Example 17

3-(6-(4-(4-(5-cyano-1H-indol-3-yl)butyl)piperazin-1-yl)pyridin-3-yl)benzamide

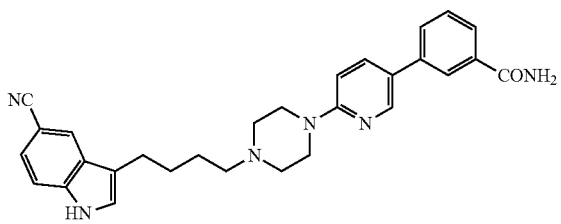 [SMILES: N#Cc1ccc2[nH]cc(CCCCN3CCN(c4ccc(-c5cccc(C(N)=O)c5)cn4)CC3)c2c1]

Step 1) Synthesis of tert-butyl 4-(5-bromopyridin-2-yl)piperazine-1-carboxylate The title compound was prepared using tert-butyl piperazine-1-carboxylate (1.45 g, 7.79 mmol), 5-bromo-2-chloropyridine (1.00 g, 5.20 mmol) and potassium carbonate (1.44 g, 10.39 mmol) in acetonitrile (30 mL) according to the process described in Step 4 of Example 1, and the crude product was purified by silica gel chromatography (PE/EtOAc (v/v)=20/1) to give the title compound as a pale yellow solid (1.45 g, 81.5%).

MS (ESI, pos. ion) m/z: 342.1 [M+H]$^+$; and
$^1$H NMR (600 MHz, CDCl$_3$): δ (ppm) 8.17 (d, J=2.4 Hz, 1H), 7.52 (dd, J=9.0, 2.5 Hz, 1H), 6.52 (d, J=9.0 Hz, 1H), 3.55-3.49 (m, 4H), 3.49-3.45 (m, 4H), 1.46 (s, 9H).

Step 2) Synthesis of tert-butyl 4-(5-(3-carbamoylphenyl)pyridin-2-yl)piperazine-1-carboxylate The title compound was prepared using tert-butyl 4-(5-bromopyridin-2-yl)piperazine-1-carboxylate (1.45 g, 4.24 mmol), (3-carbamoylphenyl) boric acid (700 mg, 4.24 mmol), Pd(dppf)Cl$_2$ (310 mg, 0.42 mmol) and caesium carbonate (4.14 g, 12.71 mmol) in a mixture of 1,4-dioxane (30 mL) and water (3 mL) according to the process described in Step 5 of Example 1, and the crude product was purified by silica gel chromatography (DCM/MeOH (v/v)=50/1) to give the title compound as a pale yellow solid (1.25 mg, 77.2%).

MS (ESI, pos. ion) m/z: 383.0 [M+H]$^+$; and
$^1$H NMR (600 MHz, DMSO-d$_6$): δ (ppm) 8.53 (d, J=2.5 Hz, 1H), 8.11 (s, 1H), 8.07 (s, 1H), 7.95 (dd, J=8.9, 2.5 Hz, 1H), 7.80 (d, J=7.7 Hz, 1H), 7.77 (d, J=7.9 Hz, 1H), 7.50 (t, J=7.7 Hz, 1H), 7.42 (s, 1H), 6.95 (d, J=8.9 Hz, 1H), 3.58-3.51 (m, 4H), 3.46-3.40 (m, 4H), 1.43 (s, 9H).

Step 3) Synthesis of 3-(6-(piperazin-1-yl)pyridin-3-yl)benzamide hydrochloride The title compound was prepared using a solution of hydrogen chloride in ethyl acetate (10 mL, 4 N) and tert-butyl 4-(5-(3-carbamoylphenyl)pyridin-2-yl)piperazine-1-carboxylate (1.25 mg, 3.27 mmol) according to the process described in Step 6 of Example 1 as a pale yellow solid (950 mg, 91.3%).

MS (ESI, pos. ion) m/z: 283.1 [M+H−HCl]$^+$; and
$^1$H NMR (400 MHz, D$_2$O): δ (ppm) 8.17 (d, J=9.4 Hz, 1H), 8.05 (s, 1H), 7.73 (s, 2H), 7.66 (d, J=7.7 Hz, 1H), 7.52 (t, J=8.0 Hz, 1H), 7.32 (d, J=9.5 Hz, 1H), 4.06-3.89 (m, 4H), 3.69-3.47 (m, 4H).

Step 4) Synthesis of 3-(6-(4-(4-(5-cyano-1H-indol-3-yl)butyl)piperazin-1-yl)pyridin-3-yl) benzamide The title compound was prepared using 4-(5-cyano-1H-indol-3-yl)butyl 4-methylbenzenesulfonate (209 mg, 1.38 mmol), 3-(6-(piperazin-1-yl)pyridin-3-yl)benzamide hydrochloride (400 mg, 1.25 mmol), sodium carbonate (399 mg, 3.76 mmol) and potassium iodide (21 mg, 0.13 mmol) in acetonitrile (15 mL) according to the process described in Step 7 of Example 1, and the crude product was purified by silica gel chromatography (DCM/MeOH (v/v)=50/1) to give the title compound as a pale yellow solid (379 mg, 63.2%).

MS (ESI, pos. ion) m/z: 479.4 [M+H]$^+$;
$^1$H NMR (600 MHz, DMSO-d$_6$): δ (ppm) 11.38 (s, 1H), 8.52 (d, J=2.2 Hz, 1H), 8.13 (s, 1H), 8.10 (s, 1H), 8.08 (s, 1H), 7.90 (dd, J=8.8, 2.4 Hz, 1H), 7.81 (d, J=7.7 Hz, 1H), 7.75 (d, J=7.8 Hz, 1H), 7.54-7.46 (m, 2H), 7.44 (s, 1H), 7.40 (dd, J=8.4, 1.2 Hz, 1H), 7.33 (s, 1H), 6.88 (d, J=8.9 Hz, 1H), 3.56-3.46 (m, 4H), 2.73 (t, J=7.4 Hz, 2H), 2.46-2.38 (m, 4H), 2.37-2.28 (m, 2H), 1.66 (dt, J=15.1, 7.6 Hz, 2H), 1.51 (dt, J=14.3, 7.3 Hz, 2H); and
$^{13}$C NMR (150 MHz, DMSO-d$_6$): δ (ppm) 168.4, 158.9, 146.1, 138.5, 138.1, 136.2, 135.4, 129.4, 128.7, 127.6, 126.3, 125.3, 125.0, 124.7, 124.6, 124.0, 121.4, 116.5, 113.1, 107.3, 100.6, 58.1, 53.0, 45.1, 28.2, 26.5, 24.6.

Example 18

3-(6-(4-(3-(5-cyano-1H-indol-3-yl)propyl)piperazin-1-yl)pyridin-3-yl)benzamide

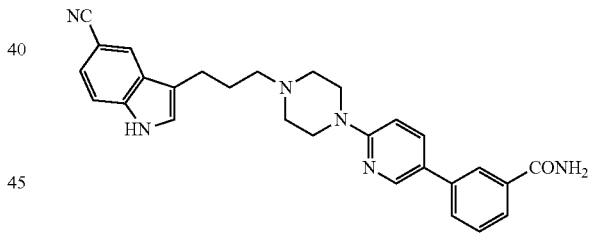

The title compound was prepared using 3-(5-cyano-1H-indol-3-yl)butyl 4-methylbenzenesulfonate (580 mg, 1.64 mmol), 3-(6-(piperazin-1-yl)pyridin-3-yl)benzamide hydrochloride (435 mg, 1.36 mmol), sodium carbonate (433 mg, 4.09 mmol) and potassium iodide (23 mg, 0.14 mmol) in acetonitrile (15 mL) according to the process described in Step 7 of Example 1, and the crude product was purified by silica gel chromatography (DCM/MeOH (v/v)=50/1) to give the title compound as a pale yellow solid (328 mg, 51.8%).

MS (ESI, pos. ion) m/z: 464.9 [M+H]$^+$;
$^1$H NMR (600 MHz, DMSO-d$_6$): δ (ppm) 11.39 (s, 1H), 8.51 (d, J=2.3 Hz, 1H), 8.11 (s, 2H), 8.07 (s, 1H), 7.91 (dd, J=8.9, 2.5 Hz, 1H), 7.79 (d, J=7.7 Hz, 1H), 7.76 (d, J=7.9 Hz, 1H), 7.49 (t, J=7.4 Hz, 2H), 7.40 (dd, J=8.5, 1.4 Hz, 2H), 7.36 (d, J=1.6 Hz, 1H), 6.92 (d, J=8.9 Hz, 1H), 3.60-3.50 (m, 4H), 2.75 (t, J=7.4 Hz, 2H), 2.50-2.43 (m, 4H), 2.40-2.31 (m, 2H), 1.89-1.78 (m, 2H); and
$^{13}$C NMR (150 MHz, DMSO-d$_6$): δ (ppm) 168.3, 158.9, 146.2, 138.4, 138.1, 136.3, 135.4, 129.4, 128.7, 127.6, 126.3, 125.5, 125.0, 124.8, 124.6, 124.0, 121.4, 116.3, 113.0, 107.4, 100.6, 57.9, 53.1, 45.2, 27.6, 22.4.

Example 19

4-(6-(4-(4-(5-cyano-1H-indol-3-yl)butyl)piperazin-1-yl)pyridin-3-yl)benzamide

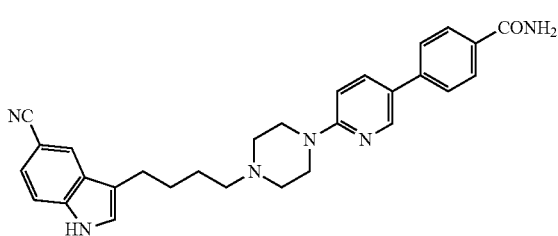 [SMILES: N#Cc1ccc2[nH]cc(CCCCN3CCN(c4ccc(-c5ccc(C(N)=O)cc5)cn4)CC3)c2c1]

Step 1) Synthesis of tert-butyl 4-(5-(4-carbamoyl-phenyl)pyridin-2-yl)piperazine-1-carboxylate The title compound was prepared using tert-butyl 4-(5-bromopyridin-2-yl)piperazine-1-carboxylate (0.81 g, 2.37 mmol), (4-carbamoylphenyl) boric acid (390 mg, 2.37 mmol), Pd(dppf)Cl$_2$ (173 mg, 0.24 mmol) and caesium carbonate (2.31 g, 7.10 mmol) in a mixture of 1,4-dioxane (15 mL) and water (1 mL) according to the process described in Step 5 of Example 1, and the crude product was purified by silica gel chromatography (DCM/MeOH (v/v)=50/1) to give the title compound as a pale yellow solid (707 mg, 78.1%).

MS (ESI, pos. ion) m/z: 383.0 [M+H]$^+$; and $^1$H NMR (400 MHz, DMSO-d$_6$): δ (ppm) 8.54 (d, J=2.4 Hz, 1H), 8.01-7.93 (m, 3H), 7.92 (s, 1H), 7.72 (s, 1H), 7.70 (s, 1H), 7.33 (s, 1H), 6.94 (d, J=8.8 Hz, 1H), 3.56 (t, J=4.8 Hz, 4H), 3.42 (t, J=4.8 Hz, 4H), 1.43 (s, 9H).

Step 2) Synthesis of 4-(6-(piperazin-1-yl)pyridin-3-yl)benzamide hydrochloride The title compound was prepared using a solution of hydrogen chloride in ethyl acetate (10 mL, 4 N) and tert-butyl 4-(5-(4-carbamoylphenyl)pyridin-2-yl)piperazine-1-carboxylate (567 mg, 1.48 mmol) according to the process described in Step 6 of Example 1 as a pale yellow solid (470 mg, 99.4%).

MS (ESI, pos. ion) m/z: 283.2 [M+H−HCl]$^+$.

Step 3) Synthesis of 4-(6-(4-(4-(5-cyano-1H-indol-3-yl)butyl)piperazin-1-yl)pyridin-3-yl) benzamide The title compound was prepared using 4-(5-cyano-1H-indol-3-yl)butyl 4-methylbenzenesulfonate (299 mg, 0.81 mmol), 4-(6-(piperazin-1-yl)pyridin-3-yl)benzamide hydrochloride (235 mg, 0.74 mmol), sodium carbonate (234 mg, 2.21 mmol) and potassium iodide (12 mg, 0.07 mmol) in acetonitrile (15 mL) according to the process described in Step 7 of Example 1, and the crude product was purified by silica gel chromatography (DCM/MeOH (v/v)=50/1) to give the title compound as a pale yellow solid (150 mg, 42.5%).

MS (ESI, pos. ion) m/z: 479.3 [M+H]$^+$;

$^1$H NMR (600 MHz, DMSO-d$_6$): δ (ppm) 11.38 (s, 1H), 8.52 (d, J=1.8 Hz, 1H), 8.08 (s, 1H), 7.98 (s, 1H), 7.95-7.92 (m, 3H), 7.71 (s, 1H), 7.70 (s, 1H), 7.50 (d, J=8.4 Hz, 1H), 7.40 (d, J=8.4 Hz, 1H), 7.34 (s, 2H), 6.91 (d, J=8.4 Hz, 1H), 3.54 (t, J=4.8 Hz, 4H), 2.74 (t, J=7.2 Hz, 2H), 2.50 (t, J=4.8 Hz, 4H), 2.42 (s, 2H), 1.67 (dt, J=14.4, 7.2 Hz, 2H), 1.55 (s, 2H); and $^{13}$C NMR (150 MHz, DMSO-d$_6$): δ (ppm) 168.0, 158.9, 146.3, 140.7, 138.5, 136.3, 132.6, 128.7, 128.5, 127.5, 126.0, 125.6, 125.4, 124.8, 124.2, 124.0, 121.4, 116.5, 113.1, 107.4, 100.6, 65.5, 57.9, 52.9, 44.9, 28.1, 24.5.

Example 20

4-(6-(4-(3-(5-cyano-1H-indol-3-yl)propyl)piperazin-1-yl)pyridin-3-yl)benzamide

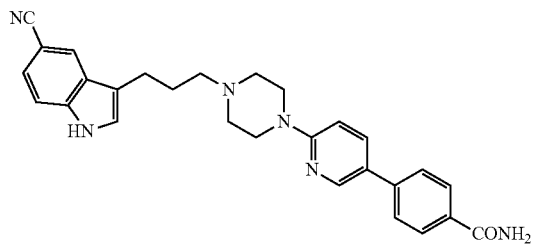 [SMILES: N#Cc1ccc2[nH]cc(CCCN3CCN(c4ccc(-c5ccc(C(N)=O)cc5)cn4)CC3)c2c1]

The title compound was prepared using 3-(5-cyano-1H-indol-3-yl)propyl 4-methylbenzenesulfonate (304 mg, 0.86 mmol), 4-(6-(piperazin-1-yl)pyridin-3-yl)benzamide hydrochloride (228 mg, 0.72 mmol), sodium carbonate (227 mg, 2.15 mmol) and potassium iodide (12 mg, 0.07 mmol) in acetonitrile (15 mL) according to the process described in Step 7 of Example 1, and the crude product was purified by silica gel chromatography (DCM/MeOH (v/v)=50/1) to give the title compound as a pale yellow solid (165 mg, 49.8%).

MS (ESI, pos. ion) m/z: 465.3 [M+H]$^+$;

$^1$H NMR (600 MHz, DMSO-d$_6$): δ (ppm) 11.39 (s, 1H), 8.52 (d, J=2.4 Hz, 1H), 8.11 (s, 1H), 7.98 (s, 1H), 7.95-7.92 (m, 3H), 7.73-7.65 (m, 2H), 7.50 (d, J=8.4 Hz, 1H), 7.40 (dd, J=8.4, 1.2 Hz, 1H), 7.36 (d, J=1.2 Hz, 1H), 7.34 (s, 1H), 6.92 (d, J=9.0 Hz, 1H), 3.57 (t, J=4.8 Hz, 4H), 2.76 (t, J=7.2 Hz, 2H), 2.50 (t, J=4.8 Hz, 4H), 2.39 (s, 2H), 1.89-1.81 (m, 2H); and $^{13}$C NMR (150 MHz, DMSO-d6): δ (ppm) 167.6, 167.0, 158.5, 145.9, 140.3, 138.0, 135.8, 132.2, 131.7, 131.6, 128.7, 128.2, 127.2, 125.1, 125.0 124.3, 123.6, 121.0, 112.6, 106.9, 100.2, 65.0, 30.0, 21.9, 18.4, 13.6.

Example 21

2-(4-(4-(5-cyano-1H-indol-3-yl)butyl)piperazin-1-yl)-5-phenylnicotinamide

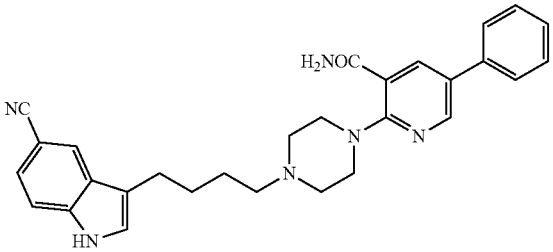 [SMILES: N#Cc1ccc2[nH]cc(CCCCN3CCN(c4ncc(-c5ccccc5)cc4C(N)=O)CC3)c2c1]

Step 1) Synthesis of tert-butyl 4-(5-bromo-3-carbamoylpyridin-2-yl)piperazine-1-carboxylate The title compound was prepared using 5-bromo-2-chloronicotinamide (1.50 g, 6.37 mmol), tert-butyl piperazine 1-carboxylate (1.19 g, 6.37 mmol) and potassium carbonate (3.52 g, 25.48 mmol) in acetonitrile (20 mL) according to the process described in Step 4 of Example 1, and the crude product was purified by silica gel chromatography (PE/EtOAc (v/v)=20/1) to give the title compound as a pale yellow solid (2.25 g, 91.8%).

MS (ESI, pos. ion) m/z: 385.2 [M+H]$^+$; and
$^1$H NMR (400 MHz, DMSO-d$_6$): δ (ppm) 8.31 (d, J=2.4 Hz, 1H), 7.95 (s, 1H), 7.82 (d, J=2.0 Hz, 1H), 7.63 (s, 1H), 3.42 (d, J=4.8 Hz, 4H), 3.27 (d, J=4.8 Hz, 4H), 1.41 (s, 9H).

Step 2) Synthesis of tert-butyl 4-(3-carbamoyl-5-phenylpyridin-2-yl)piperazine-1-carboxylate The title compound was prepared using tert-butyl 4-(5-bromo-3-carbamoylpyridin-2-yl)piperazine-1-carboxylate (1.25 g, 3.24 mmol), phenylboronic acid (396 mg, 3.24 mmol), Pd(dppf)Cl$_2$ (237 mg, 0.32 mmol) and caesium carbonate (3.17 g, 9.73 mmol) in a mixture of 1,4-dioxane (30 mL) and water (2 mL) according to the process described in Step 5 of Example 1, and the crude product was purified by silica gel chromatography (DCM/MeOH (v/v)=50/1) to give the title compound as a pale yellow solid (946 mg, 76.3%).

MS (ESI, pos. ion) m/z: 383.0 [M+H]$^+$; and
$^1$H NMR (400 MHz, DMSO-d$_6$): δ (ppm) 8.56 (d, J=2.4 Hz, 1H), 7.99 (d, J=2.4 Hz, 1H), 7.97 (s, 1H), 7.68 (s, 1H), 7.66 (s, 1H), 7.59 (s, 1H), 7.46 (t, J=7.6 Hz, 2H), 7.35 (t, J=7.6 Hz, 1H), 3.46 (t, J=4.8 Hz, 4H), 3.30 (t, J=4.8 Hz, 4H), 1.42 (s, 9H).

Step 3) Synthesis of 5-phenyl-2-(piperazin-1-yl)nicotinamide hydrochloride

The title compound was prepared using a solution of hydrogen chloride in ethyl acetate (10 mL, 4 N) and tert-butyl 4-(3-carbamoyl-5-phenylpyridin-2-yl)piperazine-1-carboxylate (945 mg, 2.47 mmol) according to the process described in Step 6 of Example 1 as a yellow solid (780 mg, 99.0%).

MS (ESI, pos. ion) m/z: 283.3 [M+H–HCl]$^+$.

Step 4) Synthesis of 2-(4-(4-(5-cyano-1H-indol-3-yl)butyl)piperazin-1-yl)-5-phenylnicotinamide The title compound was prepared using 4-(5-cyano-1H-indol-3-yl)butyl 4-methylbenzenesulfonate (478 mg, 1.30 mmol), 5-phenyl-2-(piperazin-1-yl)nicotinamide hydrochloride (346 mg, 1.09 mmol), sodium carbonate (344 mg, 3.25 mmol) and potassium iodide (18 mg, 0.11 mmol) in acetonitrile (15 mL) according to the process described in Step 7 of Example 1, and the crude product was purified by silica gel chromatography (DCM/MeOH (v/v)=50/1) to give the title compound as a pale yellow solid (250 mg, 48.8%).

MS (ESI, pos. ion) m/z: 478.9 [M+H]$^+$;
$^1$H NMR (600 MHz, DMSO-d$_6$): δ (ppm) 11.37 (s, 1H), 8.54 (d, J=1.8 Hz, 1H), 8.08 (s, 1H), 7.96 (d, J=2.4 Hz, 1H), 7.95 (s, 1H), 7.66 (s, 1H), 7.65 (s, 1H), 7.58 (s, 1H), 7.49 (d, J=8.4 Hz, 1H), 7.47-7.45 (m, 2H), 7.40 (d, J=8.4 Hz, 1H), 7.35-7.33 (m, 2H), 3.29 (t, J=4.8 Hz, 4H), 2.73 (t, J=7.8 Hz, 2H), 2.46 (t, J=4.8 Hz, 4H), 2.35 (t, J=6.6 Hz, 2H), 1.67 (dt, J=14.4, 7.2 Hz, 2H), 1.52 (dt, J=14.4, 7.2 Hz, 2H); and
$^{13}$C NMR (150 MHz, DMSO-d$_6$): δ (ppm) 169.2, 157.0, 146.1, 138.0, 136.8, 136.2, 129.1, 127.3, 127.1, 126.8, 126.0, 124.9, 124.2, 123.5, 121.0, 120.2, 116.0, 112.6, 100.1, 57.7, 52.6, 48.6, 27.7, 26.1, 24.1.

Example 22

2-(4-(3-(5-cyano-1H-indol-3-yl)propyl)piperazin-1-yl)-5-phenylnicotinamide

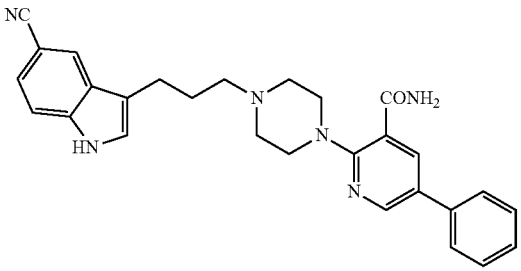 [SMILES: N#Cc1ccc2[nH]cc(CCCN3CCN(c4ncc(-c5ccccc5)cc4C(N)=O)CC3)c2c1]

The title compound was prepared using 3-(5-cyano-1H-indol-3-yl)propyl 4-methylbenzenesulfonate (467 mg, 1.32 mmol), 5-phenyl-2-(piperazin-1-yl)nicotinamide hydrochloride (350 mg, 1.10 mmol), sodium carbonate (349 mg, 3.29 mmol) and potassium iodide (18 mg, 0.11 mmol) in acetonitrile (15 mL) according to the process described in Step 7 of Example 1, and the crude product was purified by silica gel chromatography (DCM/MeOH (v/v)=50/1) to give the title compound as a pale yellow solid (291 mg, 57.1%).

MS (ESI, pos. ion) m/z: 464.9 [M+H]$^+$;
$^1$H NMR (600 MHz, DMSO-d6): δ (ppm) 11.38 (s, 1H), 8.55 (d, J=2.4 Hz, 1H), 8.10 (s, 1H), 7.96 (d, J=2.4 Hz, 1H), 7.95 (s, 1H), 7.67 (s, 1H), 7.65 (s, 1H), 7.58 (s, 1H), 7.49 (d, J=8.4 Hz, 1H), 7.46 (t, J=7.8 Hz, 2H), 7.40 (dd, J=8.4, 1.2 Hz, 1H), 7.37-7.31 (m, 2H), 3.36 (t, J=4.8 Hz, 4H), 2.75 (t, J=7.2 Hz, 2H), 2.48 (t, J=4.8 Hz, 4H), 2.37 (s, 2H), 1.88-1.79 (m, 2H); and
$^{13}$C NMR (150 MHz, DMSO-d$_6$): δ (ppm) 169.2, 156.9, 146.1, 137.9, 136.8, 136.2, 129.1, 127.2, 127.1, 126.7, 126.0, 125.0, 124.3, 123.6, 121.0, 120.2, 115.8, 112.6, 100.2, 57.4, 52.6, 48.6, 27.1, 21.9.

Example 23

2-(4-(4-(5-cyano-1H-indol-3-yl)butyl)piperazin-1-yl)-5-(4-fluoro-2-methoxy phenyl)nicotinamide

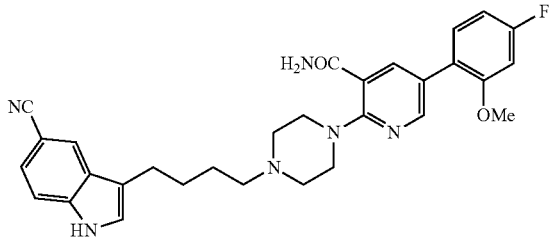 [SMILES: COc1cc(F)ccc1-c1cnc(N2CCN(CCCCc3c[nH]c4ccc(C#N)cc34)CC2)c(C(N)=O)c1]

Step 1) Synthesis of tert-butyl 4-(3-carbamoyl-5-(4-fluoro-2-methoxyphenyl)pyridin-2-yl) piperazine-1-carboxylate The title compound was prepared using tert-butyl 4-(5-bromo-3-carbamoylpyridin-2-yl)piperazine-1-carboxylate (966 mg, 2.51 mmol) reacted with (4-fluoro-2-methoxyphenyl)boronic acid (426 mg, 2.51 mmol), Pd(dppf)Cl$_2$ (183 mg, 0.25 mmol) and caesium carbonate (2.45 g, 7.52 mmol) in a mixture of 1,4-dioxane (30 mL) and water (2 mL) according to the process described in Step 5 of Example 1, and the crude product was purified by silica gel chromatography (DCM/MeOH (v/v)=50/1) to give the title compound as a pale yellow solid (900 mg, 83.3%).

MS (ESI, pos. ion) m/z: 431.3 [M+H]$^+$; and $^1$H NMR (400 MHz, DMSO-d$_6$): δ (ppm) 8.32 (d, J=2.4 Hz, 1H), 7.91 (s, 1H), 7.82 (d, J=2.4 Hz, 1H), 7.56 (s, 1H), 7.36-7.34 (m, 1H), 7.03 (dd, J=11.6, 2.4 Hz, 1H), 6.86 (td, J=8.4, 2.4 Hz, 1H), 3.80 (s, 3H), 3.46 (t, J=4.8 Hz, 4H), 3.28 (t, J=4.8 Hz, 4H), 1.42 (s, 9H).

Step 2) Synthesis of 5-(4-fluoro-2-methoxyphenyl)-2-(piperazin-1-yl)nicotinamide hydrochloride The title compound was prepared using a solution of hydrogen chloride in ethyl acetate (10 mL, 4 N) and tert-butyl 4-(3-carbamoyl-5-(4-fluoro-methoxyphenyl)pyridin-2-yl)piperazine-1-carboxylate (900 mg, 2.09 mmol) according to the process described in Step 6 of Example 1 as a yellow solid (660 mg, 99.0%).

MS (ESI, pos. ion) m/z: 331.1 [M+H−HCl]$^+$.

Step 3) Synthesis of 2-(4-(4-(5-cyano-1H-indol-3-yl)butyl)piperazin-1-yl)-5-(4-fluoro-2-methoxyphenyl)nicotinamide The title compound was prepared using 4-(5-cyano-1H-indol-3-yl)butyl 4-methylbenzenesulfonate (397 mg, 1.08 mmol), 5-(4-fluoro-methoxyphenyl)-2-(piperazin-1-yl)nicotinamide hydrochloride (330 mg, 0.90 mmol), sodium carbonate (286 mg, 2.69 mmol) and potassium iodide (15 mg, 0.09 mmol) in acetonitrile (15 mL) according to the process described in Step 7 of Example 1, and the crude product was purified by silica gel chromatography (DCM/MeOH (v/v)=50/1) to give the title compound as a pale yellow solid (270 mg, 57.1%).

MS (ESI, pos. ion) m/z: 526.8 [M+H]$^+$;

$^1$H NMR (600 MHz, DMSO-d$_6$): δ (ppm) 9.80 (s, 1H), 8.37 (d, J=2.4 Hz, 1H), 8.10 (s, 1H), 7.95 (s, 1H), 7.88 (d, J=2.4 Hz, 1H), 7.64 (s, 1H), 7.51 (d, J=8.4 Hz, 1H), 7.41 (d, J=8.4 Hz, 1H), 7.39-7.35 (m, 2H), 7.05 (dd, J=11.4, 1.8 Hz, 1H), 6.88 (td, J=8.4, 1.8 Hz, 1H), 4.22 (t, J=4.8 Hz, 4H), 3.80 (s, 3H), 3.58 (d, J=11.4 Hz, 2H), 3.27 (t, J=4.8 Hz, 4H), 3.17-3.06 (m, 2H), 2.78 (t, J=7.2 Hz, 2H), 1.72-1.66 (m, 2H); and $^{13}$C NMR (150 MHz, DMSO-d$_6$): δ (ppm) 168.7, 162.7 (d, J=243.2 Hz), 157.6 (d, J=10.3 Hz), 155.4, 148.4, 139.1, 138.1, 131.1 (d, J=9.9 Hz), 126.8, 125.7, 125.4, 124.3, 123.8, 122.0 (d, J=3.0 Hz), 120.9, 120.2, 115.2, 112.7, 107.2 (d, J=21.3 Hz), 100.4, 100.1 (d, J=25.9 Hz), 56.1, 55.6, 50.8, 45.8, 26.8, 23.7, 23.0.

Example 24

2-(4-(3-(5-cyano-1H-indol-3-yl)propyl)piperazin-1-yl)-5-(4-fluoro-2-methoxy phenyl)nicotinamide

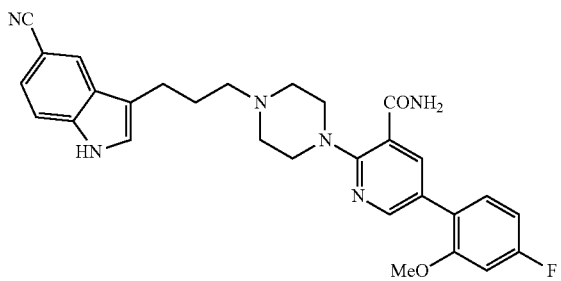 [SMILES: COc1cc(F)ccc1-c1cnc(N2CCN(CCCc3c[nH]c4ccc(C#N)cc34)CC2)c(C(N)=O)c1]

The title compound was prepared using 3-(5-cyano-1H-indol-3-yl)propyl 4-methylbenzenesulfonate (383 mg, 1.08 mmol), 5-(4-fluoro-2-methoxyphenyl)-2-(piperazin-1-yl)nicotinamide hydrochloride (330 mg, 0.90 mmol), sodium carbonate (286 mg, 2.70 mmol) and potassium iodide (15 mg, 0.09 mmol) in acetonitrile (15 mL) according to the process described in Step 7 of Example 1, and the crude product was purified by silica gel chromatography (DCM/MeOH (v/v)=50/1) to give the title compound as a pale yellow solid (290 mg, 62.9%).

MS (ESI, pos. ion) m/z: 513.3 [M+H]$^+$;

$^1$H NMR (600 MHz, DMSO-d$_6$): δ (ppm) 9.88 (s, 1H), 8.37 (s, 1H), 8.14 (s, 1H), 7.93 (s, 1H), 7.88 (s, 1H), 7.63 (s, 1H), 7.53 (d, J=8.4 Hz, 1H), 7.45-7.40 (m, 2H), 7.37 (t, J=7.8 Hz, 1H), 7.05 (d, J=11.4 Hz, 1H), 6.87 (t, J=7.2 Hz, 1H), 4.32 (t, J=4.8 Hz, 4H), 3.80 (s, 3H), 3.61 (d, J=10.2 Hz, 2H), 3.22 (t, J=4.8 Hz, 4H), 2.80 (t, J=6.6 Hz, 2H), 2.08 (d, J=7.2 Hz, 2H); and $^{13}$H NMR (150 MHz, DMSO-d$_6$): δ (ppm) 168.6, 162.8 (d, J=243.2 Hz), 157.6 (d, J=10.3 Hz), 155.4, 148.4, 139.1, 138.1, 131.1 (d, J=9.9 Hz), 126.8, 125.7, 125.4, 124.3, 123.8, 122.0 (d, J=3.0 Hz), 120.9, 120.2, 114.2, 112.8, 107.2 (d, J=21.3 Hz), 100.4, 100.1 (d, J=25.9 Hz), 56.1, 55.6, 50.8, 45.9, 24.2, 21.5.

Examples 25-40

Suitable materials were used to afford the following compounds by using the methods described in Scheme 1-5 and Example 1.

| Example | Compound structure | Characterization data |
|---|---|---|
| Example 25 | ![structure] | LC-MS: (pos.ion) m/z: 610.2 [M + 1]$^+$. |

| Example | Compound structure | Characterization data |
| --- | --- | --- |
| Example 26 | 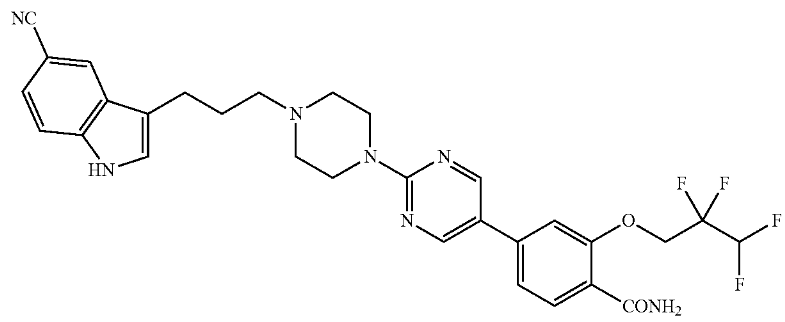 [SMILES: N#Cc1ccc2[nH]cc(CCCN3CCN(c4ncc(-c5ccc(C(N)=O)c(OCC(F)(F)C(F)F)c5)cn4)CC3)c2c1] | LC-MS: (pos.ion) m/z: 596.2 [M + 1]+. |
| Example 27 | 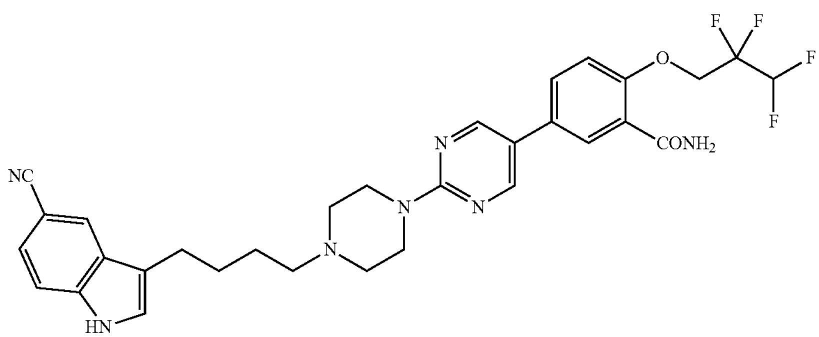 [SMILES: N#Cc1ccc2[nH]cc(CCCCN3CCN(c4ncc(-c5ccc(OCC(F)(F)C(F)F)c(C(N)=O)c5)cn4)CC3)c2c1] | LC-MS: (pos.ion) m/z: 610.2 [M + 1]+. |
| Example 28 | 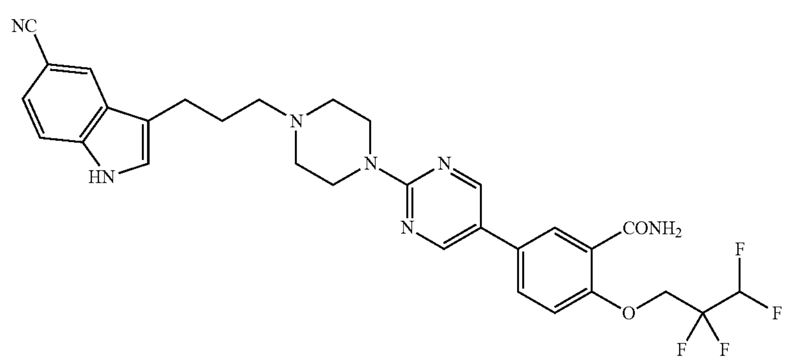 [SMILES: N#Cc1ccc2[nH]cc(CCCN3CCN(c4ncc(-c5ccc(OCC(F)(F)C(F)F)c(C(N)=O)c5)cn4)CC3)c2c1] | LC-MS: (pos.ion) m/z: 596.2 [M + 1]+. |
| Example 29 | 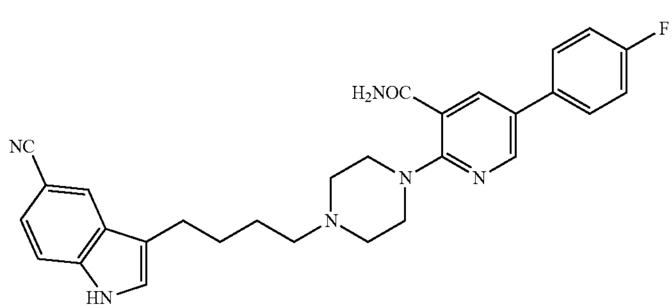 [SMILES: N#Cc1ccc2[nH]cc(CCCCN3CCN(c4ncc(-c5ccc(F)cc5)cc4C(N)=O)CC3)c2c1] | LC-MS: (pos.ion) m/z: 497.2 [M + 1]+. |

| Example | Compound structure | Characterization data |
| --- | --- | --- |
| Example 30 | 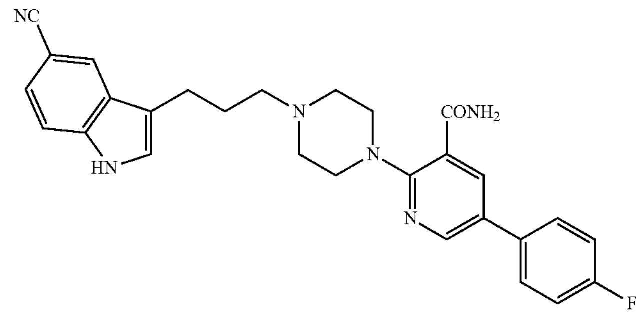 [SMILES: N#Cc1ccc2[nH]cc(CCCN3CCN(c4ncc(-c5ccc(F)cc5)cc4C(N)=O)CC3)c2c1] | LC-MS: (pos.ion) m/z: 483.2 [M + 1]+. |
| Example 31 | 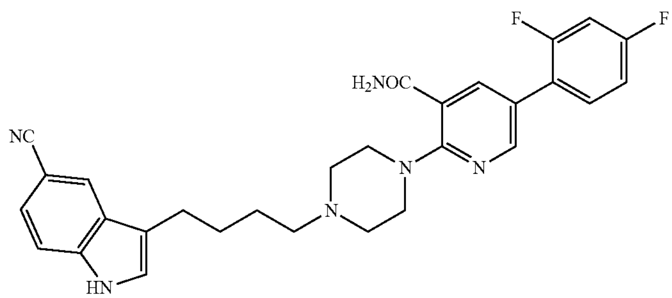 [SMILES: N#Cc1ccc2[nH]cc(CCCCN3CCN(c4ncc(-c5ccc(F)cc5F)cc4C(N)=O)CC3)c2c1] | LC-MS: (pos.ion) m/z: 515.2 [M + 1]+. |
| Example 32 | 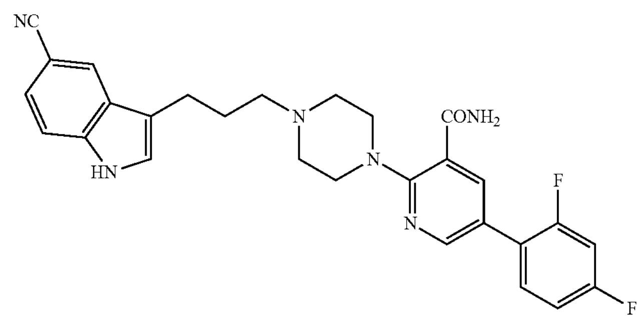 [SMILES: N#Cc1ccc2[nH]cc(CCCN3CCN(c4ncc(-c5ccc(F)cc5F)cc4C(N)=O)CC3)c2c1] | LC-MS: (pos.ion) m/z: 501.2 [M + 1]+. |
| Example 33 | 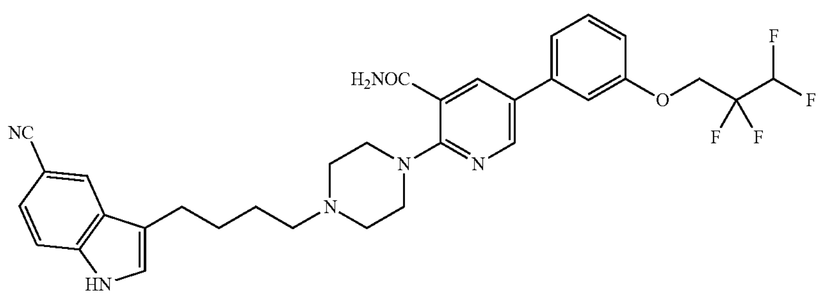 [SMILES: N#Cc1ccc2[nH]cc(CCCCN3CCN(c4ncc(-c5cccc(OCC(F)(F)C(F)F)c5)cc4C(N)=O)CC3)c2c1] | LC-MS: (pos.ion) m/z: 609.2 [M + 1]+. |
| Example 34 | 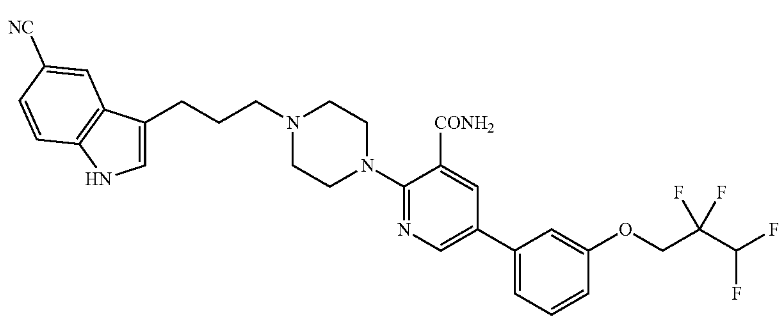 [SMILES: N#Cc1ccc2[nH]cc(CCCN3CCN(c4ncc(-c5cccc(OCC(F)(F)C(F)F)c5)cc4C(N)=O)CC3)c2c1] | LC-MS: (pos.ion) m/z: 595.2 [M + 1]+. |

-continued

| Example | Compound structure | Characterization data |
|---|---|---|
| Example 35 | 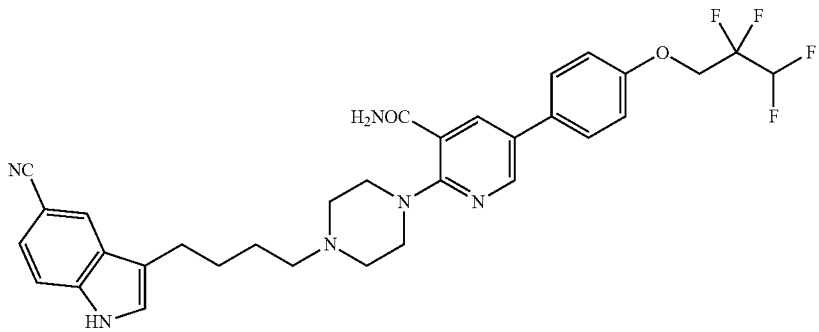 [SMILES: N#Cc1ccc2[nH]cc(CCCCN3CCN(c4ncc(-c5ccc(OCC(F)(F)C(F)F)cc5)cc4C(N)=O)CC3)c2c1] | LC-MS: (pos.ion) m/z: 609.2 [M + 1]+. |
| Example 36 | 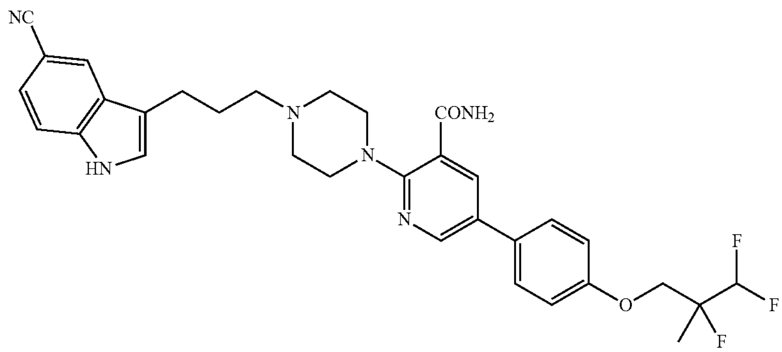 | LC-MS: (pos.ion) m/z: 595.2 [M + 1]+. |
| Example 37 | 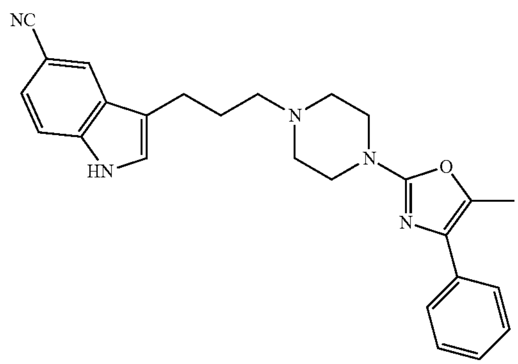 [SMILES: Cc1oc(N2CCN(CCCc3c[nH]c4ccc(C#N)cc34)CC2)nc1-c1ccccc1] | LC-MS: (pos.ion) m/z: 426.2 [M + 1]+. |
| Example 38 | 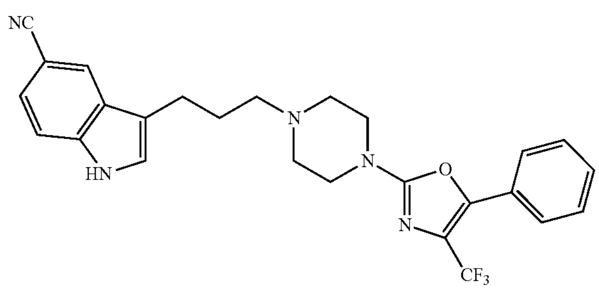 [SMILES: N#Cc1ccc2[nH]cc(CCCN3CCN(c4nc(C(F)(F)F)c(-c5ccccc5)o4)CC3)c2c1] | LC-MS: (pos.ion) m/z: 480.2 [M + 1]+. |
| Example 39 | 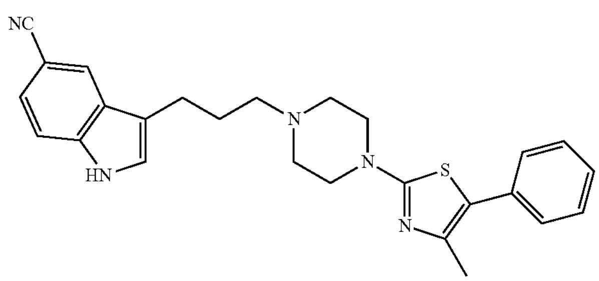 [SMILES: Cc1nc(N2CCN(CCCc3c[nH]c4ccc(C#N)cc34)CC2)sc1-c1ccccc1] | LC-MS: (pos.ion) m/z: 442.2 [M + 1]+. |

| Example | Compound structure | Characterization data |
|---|---|---|
| Example 40 | (structure) | LC-MS: (pos.ion) m/z: 496.2 [M + 1]$^+$. |

Biological Assay

Example A

Evaluation of the Affinity of Compounds to CHO Cells-Transfected Human-Derived 5-HT Transporter Test Method To a mixed system of cell membrane homogenate protein (12 μg), 2 nM of [$^3$H] imipramine and buffer solution (50 mM of Tris-HCl (pH 7.4), 120 mM of NaCl, 0.5 mM of KCl and 0.1% BSA) was added or not added the test compound at 22° C., and then the resulting mixture was incubated for 60 minutes.

To the mixed system mentioned above was added 10 μM of imipramine for measuring nonspecific binding values.

After incubation, the samples were filtered rapidly in vacuo with a 96-sample cell harvester (Unifilter, Packard) through glass-fiber filters (GF/B, Packard) pre-soaked with 0.3% PEI and rinsed several times with an ice-cold 50 mM of Tris-HCl and 150 mM of NaCl. The filters were dried and the retained radioactivity was measured by means of a scintillation counter (Topcount, Packard) using a scintillation cocktail (Microscint O, Packard). Each experimental result was expressed as a percentage inhibition of radioactive ligand specific binding relative to control groups.

The standard reference compound was imipramine, and ICso values were calculated by the competitive curve obtained from a series of concentrations of the experimental test. The experimental results of the affinity of the compounds disclosed herein to human 5-HT transporters (SERT) were listed in Table A.

TABLE A

The experimental results of the affinity of the compounds disclosed herein to human 5-HT transporters (SERT)

| Example number | IC$_{50}$ (nM) |
|---|---|
| Example 1 | 0.86 |
| Example 2 | 0.35 |
| Example 5 | 0.79 |
| Example 6 | 0.93 |
| Example 7 | 0.88 |
| Example 8 | 1.3 |
| Example 9 | 1.0 |
| Example 10 | 0.84 |
| Example 11 | 1.6 |

TABLE A-continued

The experimental results of the affinity of the compounds disclosed herein to human 5-HT transporters (SERT)

| Example number | IC$_{50}$ (nM) |
|---|---|
| Example 12 | 0.32 |
| Example 13 | 1.2 |
| Example 14 | 0.58 |
| Example 15 | 0.96 |
| Example 16 | 0.87 |

The experimental results show that the compounds of this invention have a strong affinity to human 5-HT transporter (SERT).

Example B h5-HT$_{1A}$ Binding Affinity Test

Test Method

Human HEK-293 cell homogenates (36 μg of protein) were incubated at 22° C. for 60 minutes with 0.3 nM of [$^3$H]8-OH-DPAT (Perkin-Elmer) in the absence or presence of the test compound in a buffer solution containing 50 mM of Tris-HCl (pH 7.4), 10 mM of MgSO$_4$, 0.5 mM of EDTA and 2 μg/mL aprotinine.

The non-specific binding value was determined by incubating the same mixture in the presence of 10 μM of 8-OH-DPAT, which was used as the standard reference compound. Competitive curve was obtained by testing data of 8-OH-DPAT in each experiment at several concentrations.

The incubated samples were filtered fastly using a 96-sample cell harvester (Unifilter, Packard) through fiberglass filter membranes (GF/B, Packard) pre-soaked with 0.3% PEI in vacuo, and washed several times with an ice cold 50 mM of Tris-HCl. The filter membranes were dried and the retained radioactivity was measured in a scintillation counter (Topcount, Packard) using a scintillation cocktail (Microscint 0, Packard). The experimental results were expressed as inhibition percentage of radioactive ligand specific binding relative to control groups.

Data Analysis

The experiments of combining [$^3$H]8-OH-DPAT (0.3 nM) with 5-HT$_{1A}$ receptors of human HEK-293 cells were accomplished by using Scintillation Proximity Assay on membrane. The test compounds were required to be tested at least three times in the case of a concentration of more than 6 log, and the data were analyzed by the method of nonlinear regression using Hill equation curve to obtain an $IC_{50}$ value, and then the $IC_{50}$ value was calculated by ChengPrusoff equation to obtain a Ki value. The experimental results of the binding affinity of the compounds disclosed herein to 5-$HT_{1A}$ receptors were listed in Table B.

TABLE B

The experimental results of the binding affinity of the compounds disclosed herein to 5-$HT_{1A}$ receptors

| Example number | $K_i$ (nM) |
| --- | --- |
| Example 1 | 2.87 |
| Example 2 | 1.21 |
| Example 5 | 8.42 |
| Example 6 | 4.13 |
| Example 7 | 3.7 |
| Example 8 | 1.9 |
| Example 9 | 2.7 |
| Example 10 | 3.4 |
| Example 11 | 13 |
| Example 12 | 5.5 |
| Example 13 | 1.3 |
| Example 14 | 0.92 |
| Example 15 | 11 |
| Example 16 | 7.1 |

The experimental results show that the compounds of this invention have a strong binding affinity to human 5-$HT_{1A}$ receptor.

Example C

Pharmacokinetic Evaluation of the Compounds of this Invention in Rats, Dogs and Monkeys After Intravenous or Gavage Quantitative Administration The pharmacokinetic evaluation of the compound disclosed herein in rats, dogs and monkeys was carried out in this invention, and animal information as described in Table 1.

TABLE 1 animal subjects information of the present invention

| genus | classification | gender | weight | age | source |
| --- | --- | --- | --- | --- | --- |
| SD rats | SPF | Male | 170-250 g | 6-9 weeks old | Hunan SJA Laboratory Animal Co., Ltd |
| Beagle dogs | clean grade | Male | 8~10 kg | 6-7 weeks old | Hunan SJA Laboratory Animal Co., Ltd |
| Cynomolgus monkeys | SPF | Male | 3~5 kg | 4 years old | Guangdong Landau Biotechnology Co., Ltd |

Test Method

The compounds disclosed herein were administered in form of a saline solution containing 5% DMSO, 5% Kolliphor HS 15, 2% (2% HCl) and 88% Saline, or a physiological saline solution containing 10% DMSO, 10% Kolliphor HS 15 and 80% physiological saline to an animal subject. The animals of the intravenous administration group were administered at a dose of 1 mg/kg, and 0.3 mL of vein blood samples were collected at the time points of 0, 0.083, 0.25, 0.5, 1.0, 2.0, 5.0, 7.0 and 24 h after drug administration, then each blood sample was processed to separate plasma by centrifugation at 3000 rpm or 4000 rpm for 10 minutes, and the plasma samples were collected and stored at −20° C. or −70° C. The animals of the gavage administration group were administered at a dose of 2.5 mg/kg, and 0.3 mL of vein blood samples were collected at the time points of 0, 0.083, 0.25, 0.5, 1.0, 2.0, 5.0, 7.0 and 24 h after drug administration, then each blood sample was processed to separate plasma by centrifugation at 3000 rpm or 4000 rpm for 10 minutes, and the plasma samples were collected and stored at −20° C. or −70° C.

The above plasma was analyzed by the LC/MS/MS system.

LC/MS/MS Analysis Method

The LC/MS/MS system for the analysis comprises an Agilent 1200 Series Vacuum Degasser, binary syringe pumps, a well-plate autosampler, a column oven and an Agilent G6430A Triple Quadrupole Mass Spectrometer equiped with an electrospray ionization (ESI) source. Quantitative analysis was performed in the MRM mode and the conversion parameters of MRM were listed in Table 2:

TABLE 2

| Ion source voltage | 3500 V |
| --- | --- |
| Dry gas temperature | 350° C. |
| Nebulizer | 40 psi |
| Dry gas flow rate | 9 L/min |

Analysis was performed on waters XBridge C18 (2.1×50 mm, 3.5 μM column, and 5 μL of sample was injected). Conditions of the analysis comprise: a mobile phase consisting of mobile phase A (water, 2 mM ammonium formate and 0.1% formic acid) and mobile phase B (methanol, 2 mM ammonium formate and 0.1% formic acid). A flow rate of 0.4 mL/min. Conditions of gradient elution were listed in Table 3:

TABLE 3

| Time | Gradient of mobile phase B |
| --- | --- |
| 0.9 min | 5% |
| 1.6 min | 85% |

TABLE 3-continued

| Time | Gradient of mobile phase B |
| --- | --- |
| 2.7 min | 95% |
| 2.8 min | 5% |
| 4.0 min | Stop |

The pharmacokinetic experimental results of compounds disclosed herein in rats are listed in Table C.

TABLE C

The pharmacokinetic experimental results of compounds disclosed herein in rats

| Compound Number | Administration route | Dose (mg/kg) | $T_{max}$ (h) | $C_{max}$ (ng/mL) | $AUC_{last}$ (h*ng/mL) | $AUC_{INF}$ (h*ng/mL) | $T_{1/2}$ (h) | Cl (mL/min/kg) | $V_{ss}$ (L/kg) | F (%) |
|---|---|---|---|---|---|---|---|---|---|---|
| Example 2 | iv | 1 | 0.083 | 409 | 722 | 753 | 1.59 | 22.9 | 2.33 | N/A |
|  | po | 2.5 | 0.833 | 241 | 706 | 767 | 1.95 | N/A | N/A | 39.2 |
| Example 7 | iv | 1 | 0.139 | 299 | 1010 | 1030 | 4.64 | 16.7 | 5.03 | N/A |
|  | po | 2.5 | 2.67 | 194 | 1960 | 2010 | 4.37 | N/A | N/A | 78.1 |
| Example 8 | iv | 1 | 0.139 | 195 | 1180 | 1250 | 5.85 | 13.4 | 6.01 | N/A |
|  | po | 2.5 | 4 | 180 | 2140 | 2070 | 4.85 | N/A | N/A | 68.48 |
| Example 12 | iv | 1 | 0.083 | 444 | 1870 | 2240 | 9.52 | 7.5 | 5.46 | N/A |
|  | po | 2.5 | 5.67 | 207 | 2950 | N/A | N/A | N/A | N/A | 52.62 |
| Example 13 | iv | 1 | 0.083 | 330 | 643 | 724 | 3.9 | 23.8 | 6 | N/A |
|  | po | 2.5 | 1 | 152 | 1070 | 1160 | 4.14 | N/A | N/A | 66.4 |
| Example 14 | iv | 1 | 0.25 | 193 | 1340 | 1500 | 7.53 | 11.6 | 6.41 | N/A |
|  | po | 2.5 | 5 | 180 | 2790 | 3130 | 7.28 | N/A | N/A | 83.28 |

Note:
"iv" means intravenous administration;
"po" means oral administration;
"N/A" means no test result.

The experimental results show that the compounds of the invention have good pharmacokinetic properties in rats.

Example D

The Distribution of the Compounds of this Invention in the Plasma, Brain Tissue and Cerebrospinal Fluid of Rats The distribution of the compound disclosed herein in the plasma, brain tissue and cerebrospinal fluid of rats (animal subjects information as shown in Table 1) were studied in this invention. The compounds disclosed herein were administered intravenously at a dose of 1 mg/kg to the test animals in form of a solution containing 5% DMSO, 60% PEG400, 35% saline, or a solution containing 5% DMSAO, 5% Kolliphor HS15, 88% saline, 2% (2% HCl). 0.3 mL of vein blood samples were collected at the time points of 15 min, 45 min and 75 min after drug administration, and the rats were sacrificed (3 rats per time point) and then their cerebrospinal fluid and brain tissue were removed. Each blood sample was processed to separate plasma by centrifugation at 10000 rpm for 2 minutes, and the plasma samples were collected. The plasma samples, brain tissue and cerebrospinal fluid were stored at −20° C. or −70° C. until LC/MS/MS analysis described above.

The experimental results show that the compounds of this invention have a certain distribution in the plasma, brain tissue and cerebrospinal fluid of rats.

Example E

The Evaluation of Potential the Compound Disclosed Herein Induced Prolongation of QT Interval Test Method Potential the compound disclosed herein induced QT interval prolongation was evaluated by detecting if the compound would block the hERG channel. The specific test method is as follows:

Precisely weighed compound disclosed herein was dissolved in DMSO to formulate a solution at the highest concentration of 10.0 mM, and then the solution was diluted to a initial concentration of 120.0 μM with hERG FP Assay Buffer (Invitrogen); the hERG Tracer Red stock solution (Invitrogen) and the positive control E-4031 stock solution were respectively diluted to initial concentrations of 4.0 nM and 120.0 μM with hERG FP Assay Buffer (Invitrogen). 2.5 μL of the compound disclosed herein at a initial concentration or the positive control E-4031 at a initial concentration (positive control group) or hERG FP Assay Buffer (negative control group), 5 μL of hERG Membrane and 2.5 μL of hERG Tracer Red were added into a 384-well plate, and 5 μL of hERG FP Assay Buffer and 5 μL of hERG Membrane were added as a blank control group, and the test final concentration of the compound disclosed herein, E-4031 and hERG Tracer Red were respectively 30.0 μM, 30.0 μM and 1.0 nM. Four duplicated wells per group were established. After that, the 384-well plate was put in to an oscillator (PHMP-4, Grant-sio, 25° C., 250 rpm) to incubate for 4 hours, and the fluorescence polarization values were measured by multi-function microplate reader (PHERAStarFS, BMG LABTECH), and the relative inhibition rate and 50% inhibition concentration ($IC_{50}$) of the compound disclosed herein to hERG channel were calculated.

In the case of E-4031 was as a positive control, if the relative inhibition rate of 30.0 μM of the compound disclosed herein to hERG was less than 50%, the $IC_{50}$ of the compound disclosed herein to hERG channel was more than 30.0 μM. If the relative inhibition rate of 30.0 μM of the compound disclosed herein to hERG was more than 50%, the dose titration curve of the compoud of this invention is necessary, and the specific method is as follows:

The above-mentioned solution of the compound disclosed herein and E-4031 at the initial concentration of 120 μM were respectively diluted 5-fold in series to provide 8 concentration of 120.0 μM, 24.0 μM, 4.8 μM, 960.0 nM, 192.0 nM, 38.4 nM, 7.7 nM and 1.5 nM. Two duplicated wells per concentration were established. 2.5 μL of the compound disclosed herein or the positive control E-4031 (positive control group) or hERG FP Assay Buffer (negative control group) at the determinand concentration, 5 μL of hERG FP Membrane and 2.5 μL of hERG Tracer Red were added into a 384-well plate, and 5 μL of hERG FP Assay Buffer and 5 μL of hERG Membrane were added as a blank control group. After that, the 384-well plate was put in to an oscillator (PHMP-4, Grant-sio, 25° C., 250 rpm) to incubate for 4 hours, and the fluorescence polarization values were measured by multi-function microplate reader (PHERAStarFS, BMG LABTECH) and corrected with the minimum and maximum fluorescence polarization values of E-4031, and the $IC_{50}$ of the compound disclosed herein was calculated by GraphPad software.

The experimental results show that the compound of this invention has no or weak inhibitory activity against hERG channel, which prompts there is less risk to cause QT interval elongation.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or Formula (II) or a stereoisomer, a tautomer, an N-oxide, a solvate, or a pharmaceutically acceptable salt thereof,

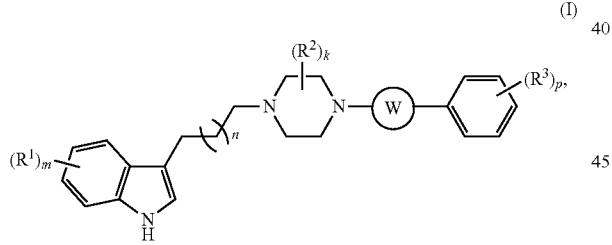

(I)

or

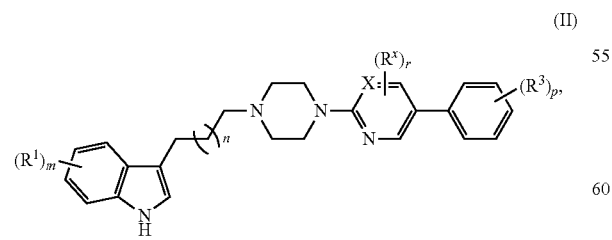

(II)

wherein:
X is CH or N;
r is 0, 1, 2 or 3;

W is one of the following heteroarylene rings:

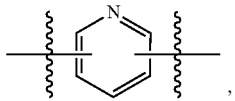

(W-1)

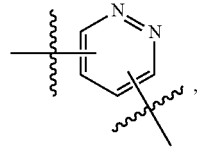

(W-2)

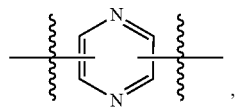

(W-3)

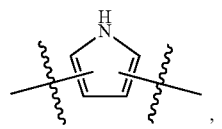

(W-5)

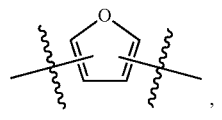

(W-6)

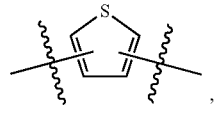

(W-7)

(W-8)

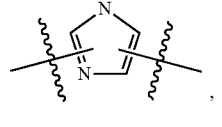

(W-9)

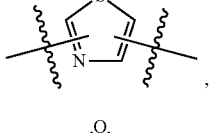

(W-10)

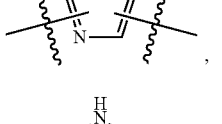

(W-11)

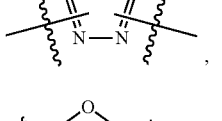

(W-12)

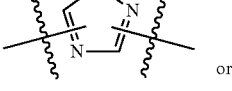

(W-13)

or

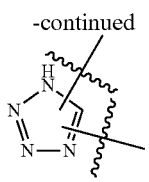

(W-14)

wherein each of Formula (W-1) to (W-3) and (W5) to (W-14) is optionally and independently substituted with one, two, three or four $R^x$ groups;

each $R^x$ is independently H, D, F, Cl, Br, I, —$NO_2$, —CN, —$NR^aR^b$, —$OR^c$, —$SR^c$, —C(=O)$R^d$, —C(=O)O$R^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, oxo (=O), $C_1$-$C_6$ alkyl, $C_2$-$C_6$ alkenyl, $C_2$-$C_6$ alkynyl or $C_1$-$C_6$ haloalkyl;

each $R^1$ is independently H, D, F, Cl, Br, I, —$NO_2$, —CN, —$NH_2$, —OH, —SH, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxy, ($C_1$-$C_6$ alkoxyl)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-;

each $R^2$ is independently H, D, F, Cl, $C_1$-$C_6$ alkyl, $C_1$-$C_6$ haloalkyl, —$NR^aR^b$, —$OR^c$, —C(=O)$R^d$, —C(=O)O$R^c$, —C(=O)$NR^aR^b$ or ($C_6$-$C_{10}$ aryl)-($C_1$-$C_6$ alkylene)-, or two adjacent $R^2$, together with the carbon atoms to which they are attached, form a $C_3$-$C_6$ carbocyclic ring, a benzene ring, a 3- to 7-membered heterocyclic ring or a 5- to 6-membered heteroaromatic ring, or two $R^2$ attached to one carbon atom, together with the carbon atom form a $C_3$-$C_6$ carbocyclic ring or a 3- to 7-membered heterocyclic ring;

each $R^3$ is independently H, D, F, Cl, Br, I, —$NO_2$, —CN, —$NR^aR^b$, —$OR^c$, —$SR^c$, —C(=O)$R^d$, —C(=O)O$R^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)O$R^c$, —N($R^a$)C(=O)$NR^aR^b$, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, or two adjacent $R^3$, together with the carbon atoms to which they are attached, form a methylenedioxy or ethylenedioxy group, wherein each —$NR^aR^b$, —$OR^c$, —$SR^c$, —C(=O)$R^d$, —C(=O)O$R^c$, —C(=O)$NR^aR^b$, —OC(=O)$R^d$, —N($R^a$)C(=O)$R^d$, —S(=O)$R^d$, —S(=O)$_2R^d$, —S(=O)$_2OR^c$, —S(=O)$_2NR^aR^b$, —N($R^a$)S(=O)$_2R^d$, —N($R^a$)C(=O)O$R^c$, —N($R^a$)C(=O)$NR^aR^b$, alkyl, alkenyl, alkynyl, haloalkyl, cycloalkyl, cycloalkylalkylene, heterocyclyl, heterocyclylalkylene, aryl, arylalkylene, heteroaryl, heteroarylalkylene, methylenedioxy and ethylenedioxy is optionally and independently substituted with one or more $R^4$ groups;

each $R^4$ is independently F, Cl, Br, I, —$NO_2$, —CN, —$N_3$, —$NH_2$, —OH, —SH, $C_1$-$C_4$ alkyl, $C_2$-$C_6$ alkenyl, $C_2$-$C_6$ alkynyl, $C_1$-$C_4$ haloalkyl, $C_1$-$C_4$ alkoxyl, $C_1$-$C_4$ haloalkoxy, $C_1$-$C_4$ alkylamino, $C_1$-$C_4$ alkylthio, $NH_2$—($C_1$-$C_4$ alkylene)-, HO—($C_1$-$C_4$ alkylene)-, HS—($C_1$-$C_4$ alkylene)-, ($C_1$-$C_4$ alkylamino)-($C_1$-$C_4$ alkylene)-, ($C_1$-$C_4$ alkoxyl)-($C_1$-$C_4$ alkylene)-, ($C_1$-$C_4$ alkylthio)-($C_1$-$C_4$ alkylene)-, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-;

each $R^a$ and $R^b$ is independently H, $C_1$-$C_6$ alkyl, $C_3$-$C_6$ alkenyl, $C_3$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-, or $R^a$ and $R^b$ together with the nitrogen atom to which they are attached, form a 3- to 7-membered heterocyclic ring;

each $R^c$ and $R^d$ is independently H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3- to 7-membered heterocyclyl, (3- to 7-membered heterocyclyl)-($C_1$-$C_4$ alkylene)-, phenyl, phenyl-($C_1$-$C_4$ alkylene)-, 5- to 6-membered heteroaryl or (5- to 6-membered heteroaryl)-($C_1$-$C_4$ alkylene)-;

each m and n is independently 0, 1, 2, 3, or 4;

k is 0, 1, 2, 3, 4, 5 or 6; and p is 0, 1, 2, 3, 4, or 5.

2. The compound according to claim 1 having Formula (III), or a stereoisomer, a tautomer, an N-oxide, a solvate, or a pharmaceutically acceptable salt thereof,

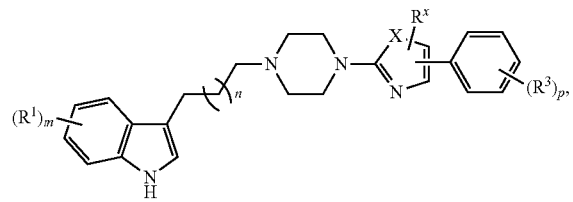

(III)

wherein Y is O, S or NH.

3. The compound according to claim 1 having Formula (V) or (VI) or a stereoisomer, a tautomer, an N-oxide, a solvate, or a pharmaceutically acceptable salt thereof,

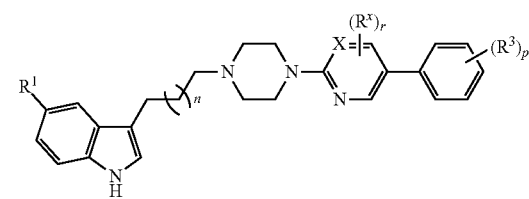

(V)

or

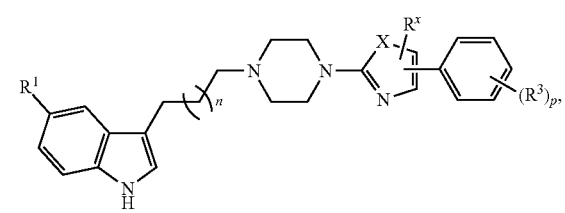

(VI)

wherein X is CH or N;
Y is O, S or NH; and
r is 0, 1, 2 or 3.

4. The compound according to claim 1, wherein each $R^x$ is independently H, D, F, Cl, —NO$_2$, —CN, —NH$_2$, —OH, -Me, -Et, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, —OMe, —OEt, —O(i-Pr), —O(t-Bu), —NMe$_2$, —C(=O)H, —C(=O)OH, —C(=O)OMe, —C(=O)OEt, —C(=O)NH$_2$, —C(=O)NMe$_2$ or oxo (=O).

5. The compound according to claim 1, wherein each $R^1$ is independently H, D, F, Cl, Br, —CN, —NO$_2$, —NH$_2$, —NMe$_2$, —OH, —OMe, —OEt, —O(i-Pr), —O(t-Bu), -Me, -Et, -(n-Pr), -(i-Pr), -(t-Bu) or —CF$_3$.

6. The compound according to claim 1, wherein each $R^2$ is independently H, D, F, Cl, —NH$_2$, —OH, -Me, -Et, -(n-Pr), -(i-Pr), -(t-Bu), —CF$_3$, —OMe, —O(i-Pr) or —O(t-Bu).

7. The compound according to claim 1, wherein each $R^3$ is independently H, D, F, Cl, Br, I, —NO$_2$, —CN, —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, C$_1$-C$_6$ alkyl, C$_2$-C$_6$ alkenyl, C$_2$-C$_6$ alkynyl, C$_1$-C$_6$ haloalkyl, C$_3$-C$_{10}$ cycloalkyl, (C$_3$-C$_{10}$ cycloalkyl)-(C$_1$-C$_6$ alkylene)-, 3- to 10-membered heterocyclyl, (3- to 10-membered heterocyclyl)-(C$_1$-C$_6$ alkylene)-, C$_6$-C$_{10}$ aryl, (C$_6$-C$_{10}$ aryl)-(C$_1$-C$_6$ alkylene)-, 5- to 10-membered heteroaryl or (5- to 10-membered heteroaryl)-(C$_1$-C$_6$ alkylene)-, or two adjacent $R^3$, together with the carbon atoms to which they are attached, form a methylenedioxy or ethylenedioxy group, wherein the —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —C(=O)OR$^c$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, C$_1$-C$_6$ alkyl, C$_2$-C$_6$ alkenyl, C$_2$-C$_6$ alkynyl, C$_1$-C$_6$ haloalkyl, C$_3$-C$_{10}$ cycloalkyl, (C$_3$-C$_{10}$ cycloalkyl)-(C$_1$-C$_6$ alkylene)-, 3- to 10-membered heterocyclyl, (3- to 10-membered heterocyclyl)-(C$_1$-C$_6$ alkylene)-, C$_6$-C$_{10}$ aryl, (C$_6$-C$_{10}$ aryl)-(C$_1$-C$_6$ alkylene)-, 5- to 10-membered heteroaryl, (5- to 10-membered heteroaryl)-(C$_1$-C$_6$ alkylene)-, methylenedioxy and ethylenedioxy are each optionally and independently substituted with one or more $R^4$ groups.

8. The compound according to claim 1, wherein each $R^3$ is independently H, D, F, Cl, Br, —CN, —NO$_2$, —NH$_2$, —NMe$_2$, —NHEt, —NEt$_2$, —OH, —OMe, —OEt, —O(n-Pr), —O(i-Pr), —O(t-Bu), -Me, -Et, -(n-Pr), -(i-Pr), -(t-Bu), —CF$_3$, —CH$_2$CH$_2$Cl, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$, —OCH$_2$CF$_2$CHF$_2$, —CONH$_2$, —CONHMe, —CONMe$_2$, —C(=O)OMe, —C(=O)OEt, —NHC(=O)H, —NHC(=O)CH$_3$, —NHC(=O)OMe or phenyl.

9. The compound according to claim 1, wherein each $R^a$ and $R^b$ is independently H, C$_1$-C$_4$ alkyl, C$_3$-C$_4$ alkenyl, C$_3$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5- to 7-membered heterocyclyl, (5- to 7-membered heterocyclyl)-(C$_1$-C$_4$ alkylene)-, phenyl, phenyl-(C$_1$-C$_4$ alkylene)-, 5- to 6-membered heteroaryl or (5- to 6-membered heteroaryl)-(C$_1$-C$_4$ alkylene)-, or $R^a$ and $R^b$ together with the nitrogen atom to which they are attached, form a 5- to 7-membered heterocyclic ring; and each $R^c$ and $R^d$ is independently H, C$_1$-C$_4$ alkyl, C$_2$-C$_4$ alkenyl, C$_2$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5- to 7-membered heterocyclyl, (5- to 7-membered heterocyclyl)-(C$_1$-C$_4$ alkylene)-, phenyl, phenyl-(C$_1$-C$_4$ alkylene)-, 5- to 6-membered heteroaryl or (5- to 6-membered heteroaryl)-(C$_1$-C$_4$ alkylene)-.

10. The compound according to claim 1, wherein each $R^a$ and $R^b$ is independently H, -Me, -Et, -(n-Pr), -(i-Pr), -(t-Bu), —CF$_3$, —CH$_2$CH$_2$Cl, cyclopentyl, pyrrolidinyl, piperidinyl, morpholinyl or piperazinyl, or $R^a$ and $R^b$ together with the nitrogen atom to which they are attached, form a 5- to 6-membered heterocyclic ring; and each $R^c$ and $R^d$ is independently H, -Me, -Et, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl.

11. The compound according to claim 1 having one of the following structures or a stereoisomer, a tautomer, an N-oxide, a solvate, or a pharmaceutically acceptable salt thereof:

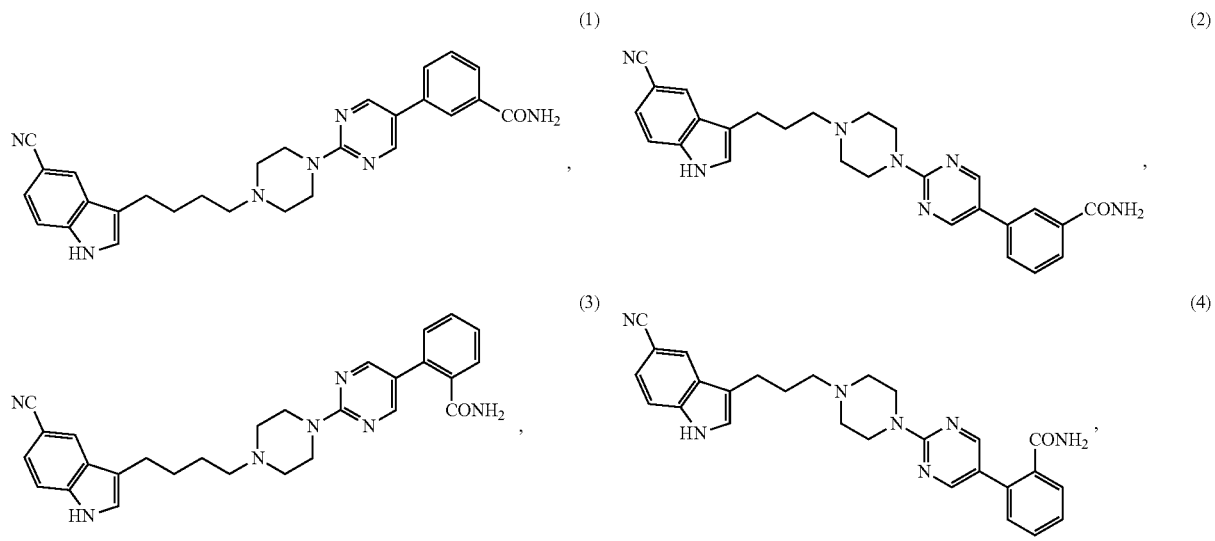

-continued
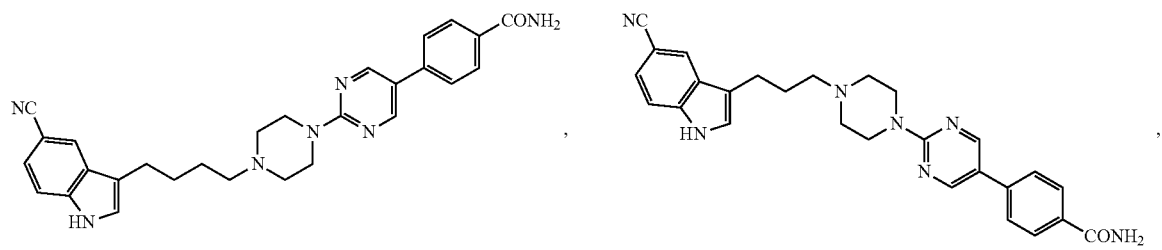
(5) (6)
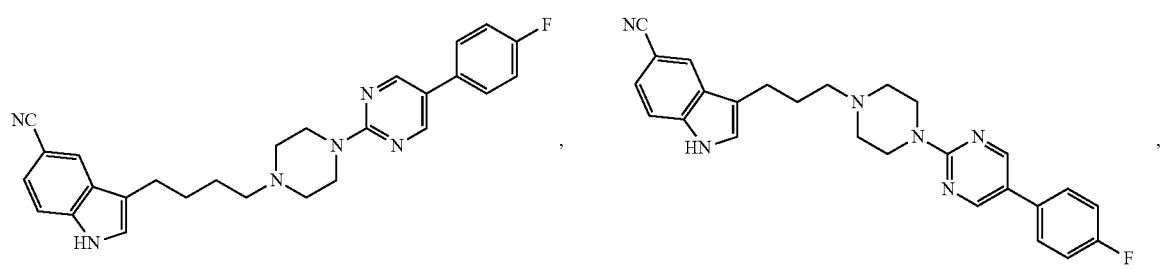
(7) (8)
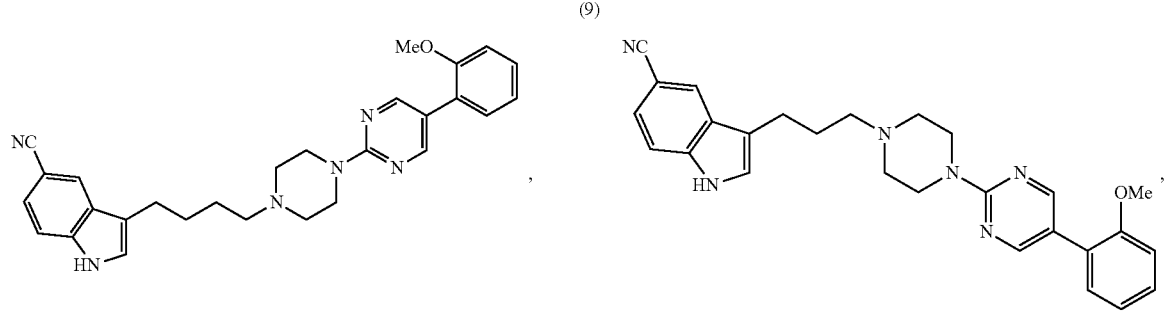
(9) (10)
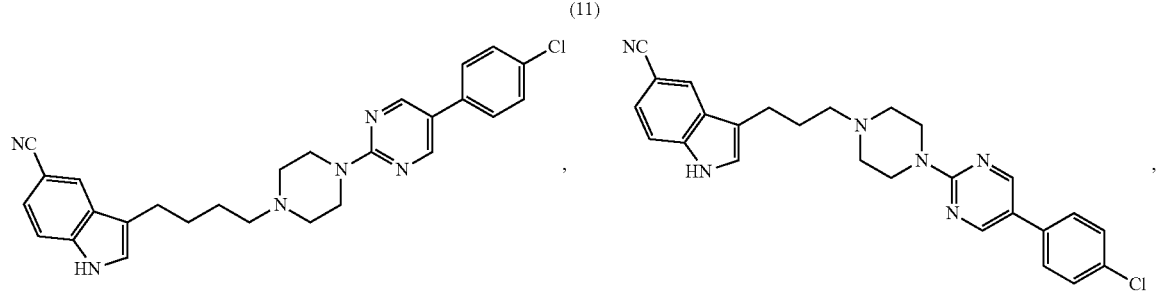
(11) (12)
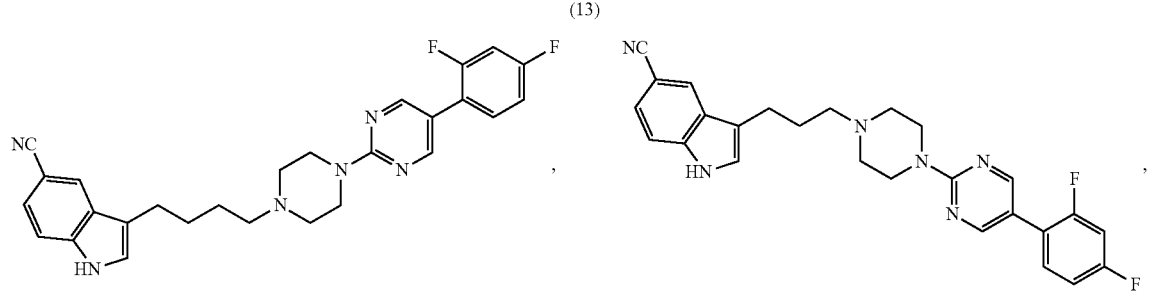
(13) (14)

(15)
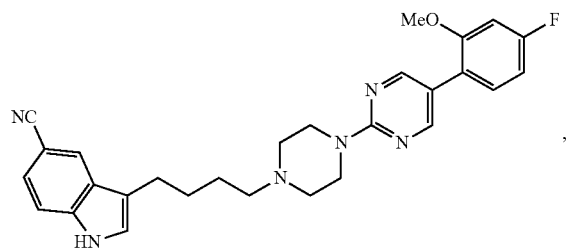
(16)
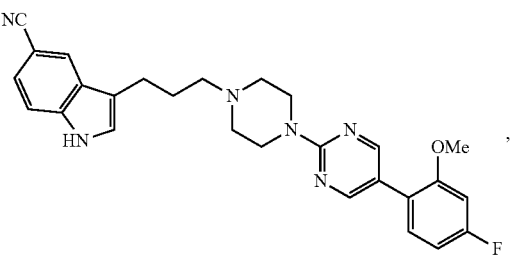
(17)
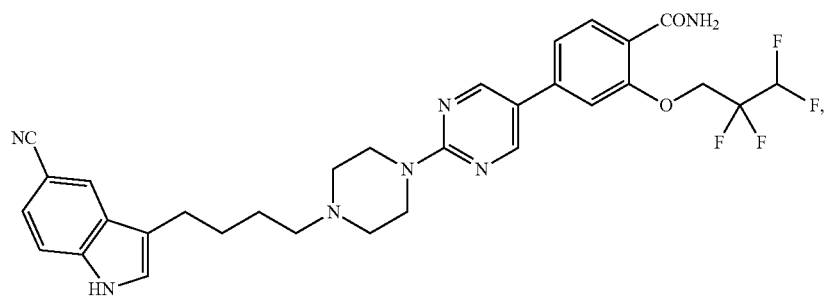
(18)
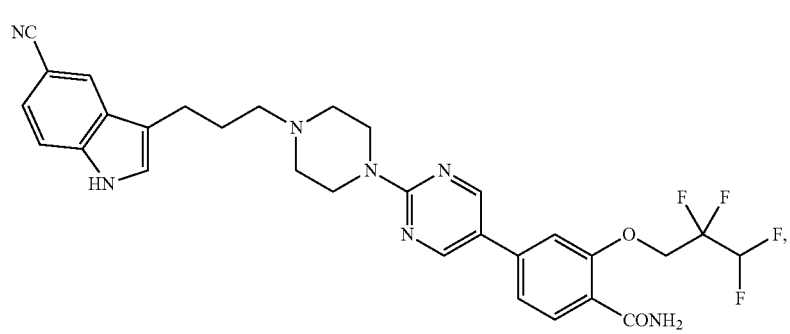
(19)
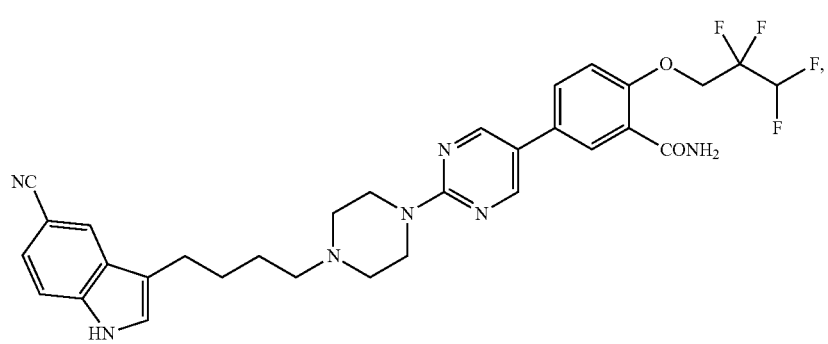
(20)
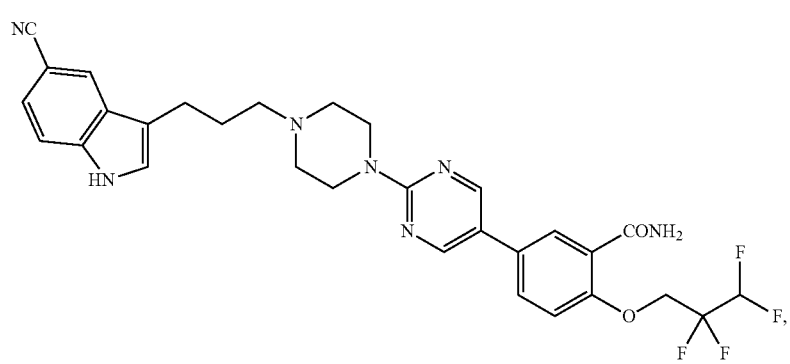

-continued
(21) 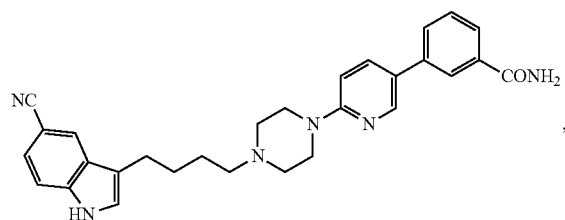
(22) 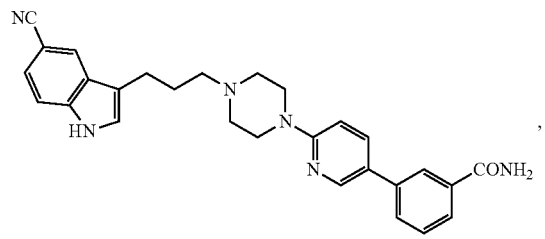
(23) 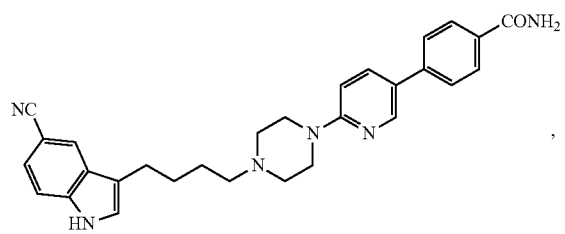
(24) 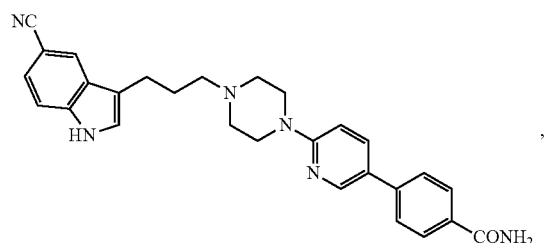
(25) 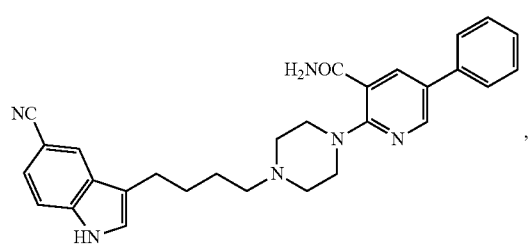
(26) 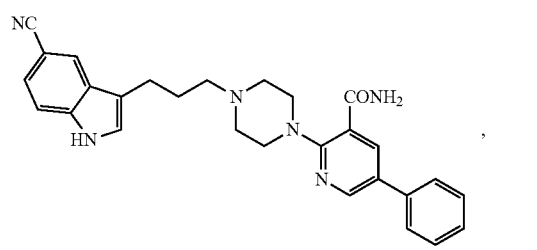
(27) 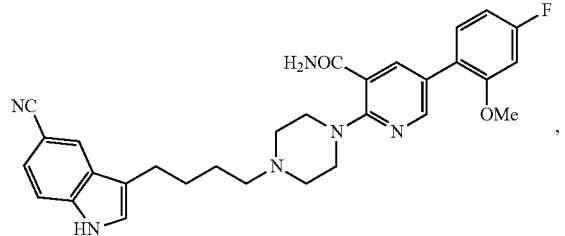
(28) 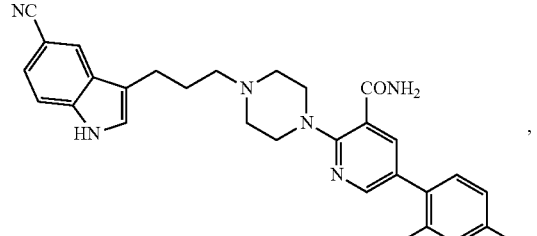
(29) 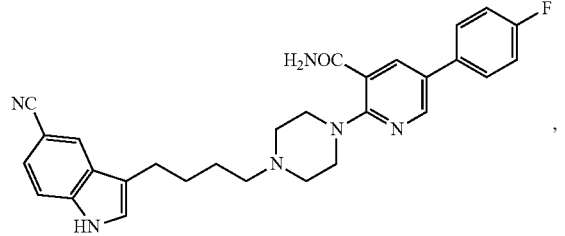
(30) 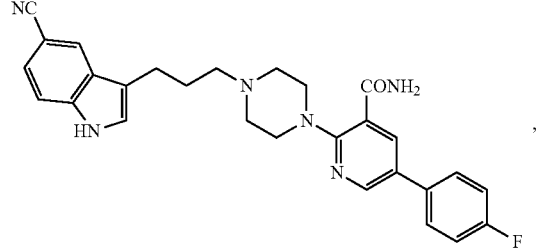
(31) 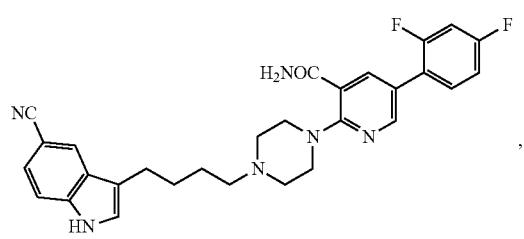
(32) 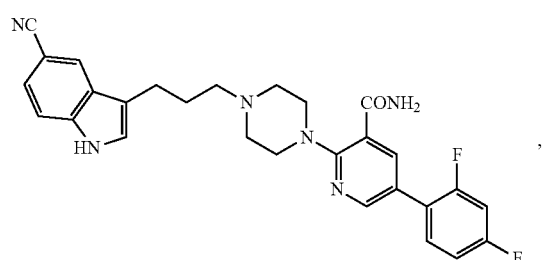

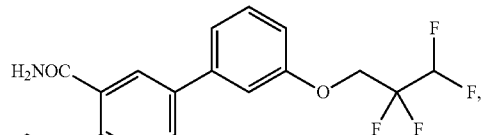
(33)
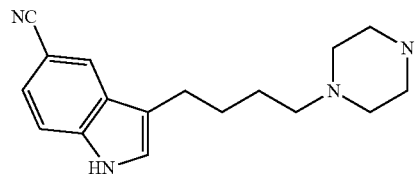
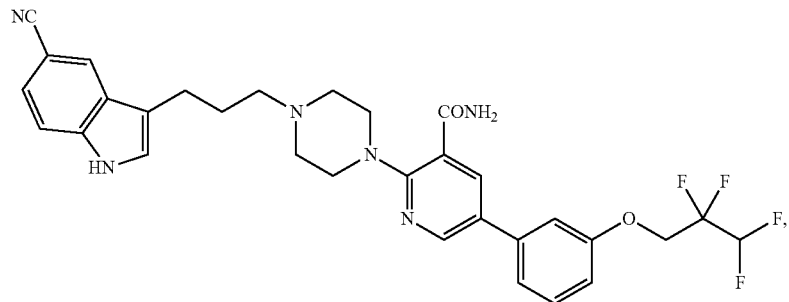
(34)
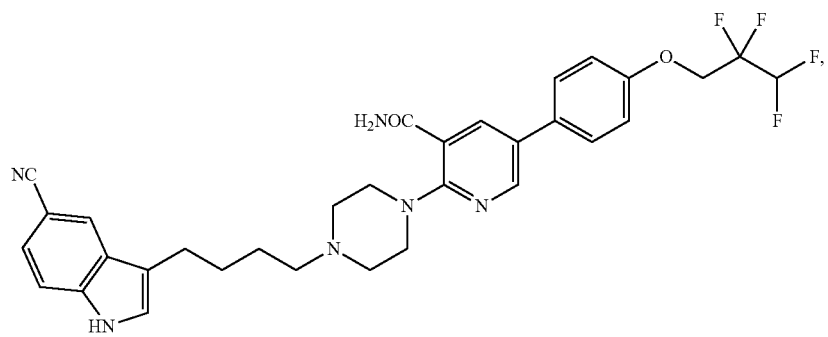
(35)
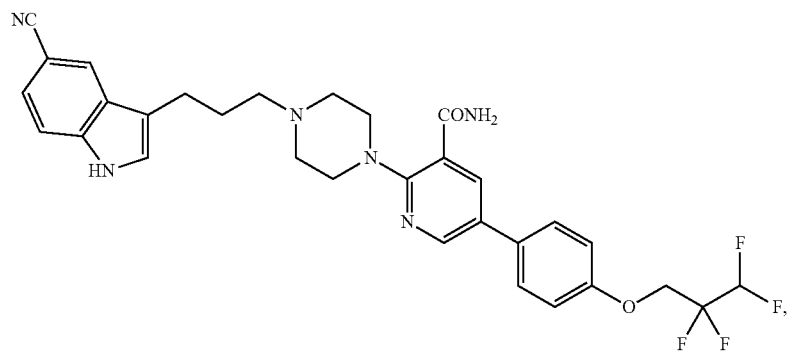
(36)

(37)
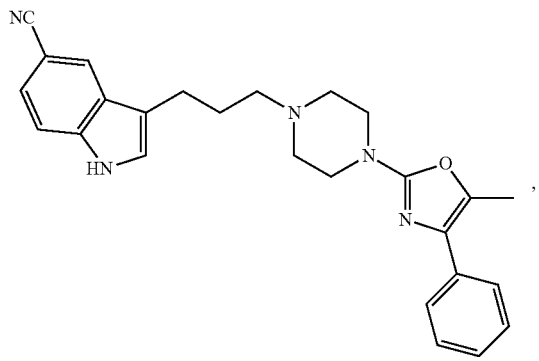 [SMILES: N#Cc1ccc2[nH]cc(CCCN3CCN(c4nc(-c5ccccc5)c(C(F)(F)F)s4)CC3)c2c1]
,
(38)
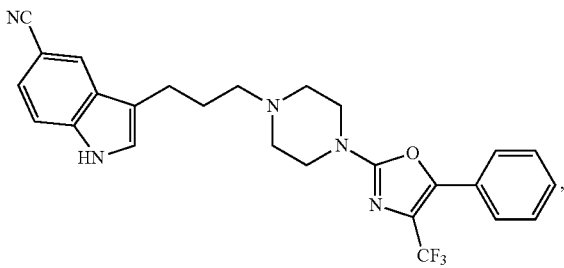
,
(39)
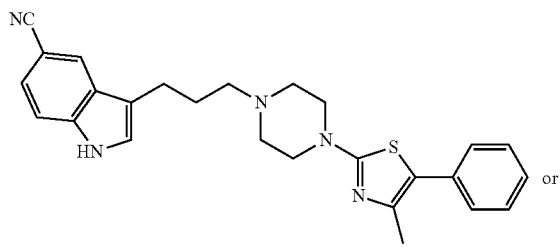
or
(40)
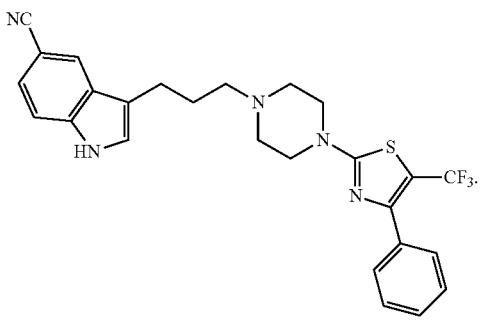
.
12. A pharmaceutical composition comprising the compound of claim 1; and a pharmaceutically acceptable excipient, carrier, adjuvant or a combination thereof.
* * * * *